(12) United States Patent
Fremont et al.

(10) Patent No.: US 11,351,227 B2
(45) Date of Patent: Jun. 7, 2022

(54) CHEMOKINE DECOY RECEPTORS OF RODENT GAMMAHERPESVIRUSES AND USES THEREOF

(71) Applicant: Washington University, St. Louis, MO (US)

(72) Inventors: Daved Fremont, St. Louis, MO (US); Olga Lubman, St. Louis, MO (US); Andrew E. Gelman, St. Louis, MO (US); Yun Hsuan Lu, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/608,672

(22) PCT Filed: Apr. 27, 2018

(86) PCT No.: PCT/US2018/030022
§ 371 (c)(1),
(2) Date: Oct. 25, 2019

(87) PCT Pub. No.: WO2018/201091
PCT Pub. Date: Nov. 1, 2018

(65) Prior Publication Data
US 2020/0164032 A1 May 28, 2020

Related U.S. Application Data

(60) Provisional application No. 62/491,083, filed on Apr. 27, 2017.

(51) Int. Cl.
*A61K 38/17* (2006.01)

(52) U.S. Cl.
CPC ............................... *A61K 38/1793* (2013.01)

(58) Field of Classification Search
CPC .................................................. A61K 38/1793
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,264,618 A | 11/1993 | Felgner et al. |
| 6,303,573 B1 | 10/2001 | Ruoslahti et al. |
| 6,843,991 B1 | 1/2005 | Efstathiou et al. |
| 2005/0054668 A1* | 3/2005 | Laborde ............... C07D 401/12 514/300 |
| 2006/0183161 A1 | 8/2006 | Nicklin et al. |
| 2009/0035318 A1* | 2/2009 | Eaves ................... A61K 31/00 424/158.1 |
| 2014/0308252 A1 | 10/2014 | Lafrancesca et al. |

FOREIGN PATENT DOCUMENTS

| | | |
|---|---|---|
| WO | 2001021204 A1 | 3/2001 |
| WO | 2014201308 A1 | 12/2014 |
| WO | 2016090404 A1 | 6/2016 |
| WO | 2018201091 A1 | 11/2018 |

OTHER PUBLICATIONS

Li et al., 2017 (epub Mar. 17, 2017), Decoy receptor 3 analogous supplement protects steatotic rat liver from ischemia-reperfusion injury, Journal of the Chinese Medical Association, 80: 391-400.*
Cochain et al., 2012, The Chemokine Decoy Receptor D6 Prevents Excessive Inflammation and Adverse Ventricular Remodeling After Myocardial Infarction, Arterioscler Thromb Vasc Biol, 32: 2206-2213.*
Frangogiannis, 2012, Regulation of the inflammatory response in cardiac repair, Circ Res, 110(1): 159-173.*
Lubman et al., Jan. 5, 2016, Parallel evolution of chemokine binding by structurally related herpesvirus decoy receptors, Structure, 24(1): 57-69.*
Alexander-Brett et al., 2007, Dual GPCRand GAG mimicry by the M3 chemokine decoy receptor, JEM, 204(13): 3157-3172.*
Fischereder, 2007, Chemokines and chemokine receptors in renal transplantation—from bench to bedside, Acta Physiologica Hungarica, 94(1-2): 67-81.*
Melve et al., 2011, The chemokine system in allogeneic stem-cell transplantation: a possible therapeutic target?, Expert Rev Hematol, 4(5): 563-576.*
Barker et al., 2014, Transplantation and inflammation: implications for the modification of chemokine function, Immunology, 143: 138-145.*
O'Boyle et al., 2011, Chemokines in transplantation: what can atypical receptors teach us about anti-inflammatory therapy?, Transplantation Reviews, 25: 136-144.*
Schenk et al., 2008, Chemokine-Directed Strategies to Attenuate Allograft Rejection, Clin Lab Med, 28(3): 441 (12 pages).*
Tan et al., 2005, Chemokine Receptors and Transplantation, Cellular & Molecular Immunology, 2(5): 343-349.*
Choi et al., 2015, Chemokine decoy receptor D6 mimicking trap (D6MT) prevents allosensitization and immune rejection in murine corneal allograft model, JLB, 97: 413 (12 pages).*
Lucas, A. et al., "Secreted Immunomodulatory Viral Proteins as Novel Biotherapeutics," J. Immunol., 2004, pp. 4765-4774, vol. 173.
Mackett, M. et al., "Vaccinia virus: A selectable eukaryotic cloning and expression vector," PNAS, Dec. 1982, pp. 7415-7419, vol. 79.
Mackett, M. et al., "General Method for Production and Selection of Infectious Vaccinia Virus Recombinants Expressing Foreign Genes," J. Virol., Mar. 1984, pp. 857-864, vol. 49, No. 3.

(Continued)

*Primary Examiner* — Amber D Steele
(74) *Attorney, Agent, or Firm* — Polsinelli PC

(57) ABSTRACT

The present disclosure generally provides compositions and methods related to the field of immunology. Specifically, disclosed herein are chemokine binding proteins and methods of use thereof.

10 Claims, 27 Drawing Sheets
(22 of 27 Drawing Sheet(s) Filed in Color)
Specification includes a Sequence Listing.

(56) References Cited

OTHER PUBLICATIONS

Maghazachi, A., "Intracellular signaling events at the leading edge of migrating cells," Int. J. Biochem. Cell Biol., 2000, pp. 931-943, vol. 32.
Martin, A. et al., "The Chemokine Decoy Receptor M3 Blocks CC Chemokine Ligand 2 and CXC Chemokine Ligand 13 Function In Vivo," J. Immunol., 2006, pp. 7296-7302, vol. 177.
Miley, M. et al., "Biochemical Features of the MHC-Related Protein 1 Consistent with an Immunological Function," J. Immunol., 2003, pp. 6090-6098, vol. 170.
Moser, B. et al., "Lymphocyte traffic control by chemokines," Nat. Immunol., Feb. 2001, pp. 123-128, vol. 2, No. 2.
Mulligan, R. et al., "Selection for animal cells that express the *Escherichia coli* gene coding for xanthine-guanine phosphoribosyltransferase," PNAS, Apr. 1981, pp. 2072-2076, vol. 78, No. 4.
Murphy, P., "Viral exploitation and subversion of the immune system through chemokine mimicry," Nat. Immunol., Feb. 2001, pp. 116-122, vol. 2, No. 2.
NCBI accession No. NC_015049, Aug. 13, 2018; 57 pgs.
O'Hare, K. et al., "Transofrmation of mouse fibroblasts to methotrexate resistance by a recombinant plasmid expressing a prokaryotic dihydrofolate reductase," PNAS, Mar. 1981, pp. 1527-1531, vol. 78, No. 3.
Panicali, D. et al., "Construction of poxviruses as cloning vectors: Insertion of the thymidine kinase gene from herpes simplex virus into the DNA of infectious vaccinia virus," PNAS, Aug. 1982, pp. 4927-4931, vol. 79.
Proudfoot, A. et al., "Purification of Recombinant Chemokines from *E. coli*," Methods Mol. Biol., 2000, pp. 75-87, vol. 138.
Proudfoot, A. et al., "Glycosaminoglycan binding and oligomerization are essential for the in vivo activity of certain chemokines," PNAS, Feb. 18, 2003, pp. 1885-1890, vol. 100, No. 4.
Pyo, R. et al., "Inhibition of Intimal Hyperplasia in Transgenic Mice Conditionally Expressing the Chemokine-Binding Protein M3," Am. J. Pathol., Jun. 2004, pp. 2289-2297, vol. 164, No. 6.
Rice, J. et al., "A gamma-herpesvirus immune evasion gene allows tumor cells in vivo to escape attack by cytotoxic T cells specific for a tumor epitope," Eur. J. Immunol., 2002, pp. 3481-3487, vol. 32.
Rosenberg, A., et al., "Vectors for selective expression of cloned DNAs by T7 RNA polymerase," Gene, 1987, pp. 125-135, vol. 56.
Ruiz-Arguello, M. et al., "An Ectromelia Virus Protein That Interacts with Chemokines through Their Glycosaminoglycan Binding Domain," J. Virol., Jan. 2008, pp. 917-926, vol. 82, No. 2.
Russo, J. et al., "Nucleotide sequence of the Kaposi sarcoma-associated herpesvirus (HHV8)," PNAS, Dec. 1996, pp. 14862-14867, vol. 93.
Santerre, R. et al., "Expression of prokaryotic genes for hygromycin B and G418 resistance as dominant-selection markers in mouse L cells," Gene, 1984, pp. 147-156, vol. 30.
Sarver, N. et al., "Bovine Papilloma Virus Deoxyribonucleic Acid: a Novel Eucaryotic Cloning Vector," Mol. Cell. Biol., Jun. 1981, pp. 486-496, vol. 1, No. 6.
Seet, B. et al., "Glycosaminoglycan Binding Properties of the Myxoma Virus CC-chemokine Inhibitor, M-T1," J. Biol. Chem., Aug. 10, 2001, pp. 30504-30513, vol. 276, No. 32.
Seet, B. et al., "Poxviruses and Immune Evasion," Annu. Rev. Immunol., 2003, pp. 377-423, vol. 21.
Sheldrick, G., "A short history of SHELX," Acta Cryst., 2008, pp. 112-122, vol. A64.
Strockbine, L. et al., "The Epstein-Barr Virus BARF1 Gene Encodes a Novel, Soluble Colony-Stimulating Factor-1 Receptor," J. Virol., May 1998, pp. 4015-4021, vol. 72, No. 5.
Szybalska, E. et al., "Genetics of Human Cell Lines, IV. DNA-Mediated Heritable Transformation of a Biochemical Trait," PNAS, 1962, pp. 2026-2034, vol. 48.
Teng, G. et al., "MicroRNA-155 is a Negative Regulator of Activation-Induced Cytidine Deaminase," Immunity, May 2008, pp. 621-629, vol. 28.

Van Berkel, V. et al., "Identification of a Gammaherpesvirus Selective Chemokine Binding Protein That Inhibits Chemokine Action," J. Virol., Aug. 2000, pp. 6741-6747, vol. 74, No. 15.
Van Berkel, V. et al., "Critical role for a high-affinity chemokine-binding protein in gamma-herpesvirus-induced lethal meningitis," J. Clin. Invest., 2002, pp. 905-914, vol. 109, No. 7.
Viejo-Borbolla, A. et al., "Enhancement of Chemokine Function as an Immunomodulatory Strategy Employed by Human Herpesviruses," PLoS Pathog., Feb. 2012, pp. 1-14, vol. 8, No. 2, e1002497.
Virgin, H. et al., "Complete Sequence and Genomic Analysis of Murine Gammaherpesvirus 68," J. Virol., Aug. 1997, pp. 5894-5904, vol. 71, No. 8.
Wang, D. et al., "Human cytomegalovirus encodes a highly specific RANTES decoy receptor," PNAS, Nov. 23, 2004, pp. 16642-16647, vol. 101, No. 47.
Wigler, M. et al., "Transfer of Purified Herpes Virus Thymidine Kinase Gene to Cultured Mouse Cells," Cell, May 1977, pp. 223-232, vol. 11.
Wigler, M. et al., "Transformation of mammalian cells with an amplifiable dominant-acting gene," PNAS, Jun. 1980, pp. 3567-3570, vol. 77, No. 6.
Alcami, A. et al., "Vaccinia, Cowpox, and Camelpox Viruses Encode Soluble Gamma Interferon Receptors with Novel Broad Species Specificity," J. Virol., Aug. 1995, pp. 4633-4639, vol. 69, No. 8.
Alcami, A. et al., "Blockade of Chemokine Activity by a Soluble Chemokine Binding Protein from Vaccinia Virus," J. Immunol., 1998, pp. 624-633, vol. 160.
Alcami, A. et al., "Viral mechanisms of immune evasion," Immunol. Today, Sep. 2000, pp. 447-455, vol. 21, No. 9.
Alcami, A. et al., "The vaccinia virus soluble interferon-gamma receptor is a homodimer," J. Gen. Virol., 2002, pp. 545-549, vol. 83.
Alcami, A. et al., "Modulation of chemokine activity by viruses," HHS Public Access Author Manuscript, Feb. 13, 2019, pp. 1-11, published in final edited form as: Curr. Opin. Immunol., Aug. 2010, pp. 482-487, vol. 22, No. 4.
Alejo, A. et al., "A chemokine-binding domain in the tumor necrosis factor receptor from variola (smallpox) virus," PNAS, Apr. 2006, pp. 5995-6000, vol. 103, No. 15.
Alexander, J. et al., "Structural Basis of Chemokine Sequestration by a Herpesvirus Decoy Receptor," Cell, Nov. 2002, pp. 343-356, vol. 111.
Alexander-Brett, J. et al., "Dual GPCR and GAG mimicry by the M3 chemokine decoy receptor," J. Exp. Med., Dec. 24, 2007, pp. 3157-3172, vol. 204, No. 13.
Arnold, P. et al., "Structural Determinants of Chemokine Binding by an Ectromelia Virus-Encoded Decoy Receptor," J. Virol., Aug. 2006, pp. 7439-7449, vol. 80, No. 15.
Bahar, M. et al., "Structure and Function of A41, a Vaccinia Virus Chemokine Binding Protein," PLoS Pathog., Jan. 2008, pp. 0055-0068, vol. 4, No. 1, e5.
Birdsall, H. et al., "Complement C5a, TGF-β1, and MCP-1, in Sequence, Induce Migration of Monocytes Into Ischemic Canine Myocardium Within the First One to Five Hours After Reperfusion," Circulation, Feb. 4, 1997, pp. 684-692, vol. 95, No. 3.
Bitter, G. et al., "Expression and Secretion Vectors for Yeast," Methods in Enzymology, 1987, pp. 516-544, vol. 153.
Bursill, C. et al., "Adenoviral-mediated delivery of a viral chemokine binding protein blocks CC-chemokine activity in vitro and in vivo," Immunobiol., 2003, pp. 187-196, vol. 207.
Cardin, A. et al., "Molecular Modeling of Protein-Glycosaminoglycan Interactions," Arteriosclerosis, Jan./Feb. 1989, pp. 21-32, vol. 9.
Colbere-Garapin, F. et al., "A New Dominant Hybrid Selective Marker for Higher Eukaryotic Cells," J. Mol. Biol., 1981, pp. 1-14, vol. 150.
Cone, R. et al., "High-efficiency gene transfer into mammalian cells: Generation of helper-free recombinant retrovirus with broad mammalian host range," PNAS, Oct. 1984, pp. 6349-6353, vol. 81.
Cyster, J., "Chemokines and Cell Migration in Secondary Lymphoid Organs," Science, Dec. 10, 1999, pp. 2098-2102, vol. 286, No. 5447.
Czaplewski, L. et al., "Identification of Amino Acid Residues Critical for Aggregation of Human CC Chemokines Macrophage

(56) References Cited

OTHER PUBLICATIONS

Inflammatory Protein (MIP)-1alpha, MIP-1beta, and Rantes," J. Biol. Chem., Jun. 4, 1999, pp. 16077-16084, vol. 274, No. 23.
Dabbagh, K. et al., "Local Blockade of Allergic Airway Hyperreactivity and Inflammation by the Poxvirus-Derived Pan-CC-Chemokine Inhibitor vCCI," J. Immunol., 2000, pp. 3418-3422, vol. 165.
Elbein, A. et al., Glycosidase inhibitors as antiviral and/or antitumor agents, Seminars in Cell Biology, Sep. 30, 1991, pp. 309-317, vol. 2, No. 5, abstract only.
Emsley, P. et al., "Coot: model-building tools for molecular graphics," Acta Crystallogr. D Biol. Crystallogr., 2004, pp. 2126-2132, vol. D60, International Union of Crystallography, Denmark.
Entman, M. et al., "Postreperfusion inflammation: a model for reaction to injury in cardiovascular disease," Cardiovascular Res., 1994, pp. 1301-1311, vol. 28.
Epperson, M. et al., "Subversion of cytokine networks by virally encoded decoy receptors," NIH Public Access Author Manuscript, Nov. 1, 2013, pp. 1-26, published in final edited form as: Immunol. Rev., Nov. 2012, pp. 199-215, vol. 250, No. 1.
Esko, J. et al., "Inhibition of Chondroitin and Heparan Sulfate Biosynthesis in Chinese Hamster Ovary Cell Mutants Defective in Galactosyltransferase I," J. Biol. Chem., Sep. 1987, pp. 12189-12195, vol. 262, No. 25.
Graham, K. et al., "The T1/35kDa Family of Poxvirus-Secreted Proteins Bind Chemokines and Modulate Leukocyte Influx into Virus-Infected Tissues," Virology, 1997, pp. 12-24, vol. 229, No. VY968423.
Hartman, S. et al., "Two dominant-acting selectable markers for gene transfer studies in mammalian cells," PNAS, Nov. 1988, pp. 8047-8051, vol. 85.
Heidarieh, H. et al., "Immune modulation by virus-encoded secreted chemokine binding proteins," Virus Res., 2015, pp. 67-75, vol. 209, Elsevier B.V.
Herr, R. et al., "Newly Discovered Viral E3 Ligase pK3 Induces Endoplasmic Reticulum-associated Degradation of Class I Major Histocompatibility Proteins and Their Membrane-bound Chaperones," J. Biol. Chem., Apr. 27, 2012, pp. 14467-14479, vol. 287, No. 18.
Hileman, R. et al., "Glycosaminoglycan-protein interactions: definition of consensus sites in glycosaminoglycan binding proteins," BioEssays, 1998, pp. 156-167, vol. 20.
Houser, B., "Bio-Rad's Bio-Plex(R) suspension array system, xMAP technology overview," Arch. Physiol. Biochem., 2012, pp. 192-196, vol. 118, No. 4.
Hughes, D. et al., "Pathogenesis of a Model Gammaherpesvirus in a Natural Host," J. Virol., Apr. 2010, pp. 3949-3961, vol. 84, No. 8.
Hughes, D. et al., "Chemokine Binding Protein M3 of Murine Gammaherpesvirus 68 Modulates the Host Response to Infection in a Natural Host," PLoS Pathog., Mar. 2011, pp. 1-15, vol. 7, No. 3, Article e1001321.
International Search Report and Written Opinion dated Jul. 26, 2018 from related Patent Application No. PCT/US2018/030022; 13 pgs.
Jensen, K. et al., "Disruption of CCL21-Induced Chemotaxis In Vitro and In Vivo by M3, a Chemokine-Binding Protein Encoded by Murine Gammaherpesvirus 68," J. Virol., Jan. 2003, pp. 624-630, vol. 77, No. 1.
Kelley, L. et al., "Protein structure prediction on the Web: a case study using the Phyre server," Nat. Protoc., 2009, pp. 363-371, vol. 4, No. 3.
Kim, K. et al., "Mechanism of Human Group V Phospholipase A2 (PLA2)-induced Leukotriene Biosynthesis in Human Neutrophils," J. Biol. Chem., Apr. 6, 2001, pp. 11126-11134, vol. 276, No. 14.
Koopmann, W. et al., "Structure and Function of the Glycosaminoglycan Binding Site of Chemokine Macrophage-Inflammatory Protein-1beta," J. Immunol., 1999, pp. 2120-2127, vol. 163.
Lalani, A. et al., The Purified Myxoma Virus Gamma Interferon Receptor Homolog M-T7 Interacts with the Heparin-Binding Domains of Chemokines, J. Virol., Jun. 1997, pp. 4356-4363, vol. 71, No. 6.
Lalani, A. et al., "Role of the Myxoma Virus Soluble CC-Chemokine Inhibitor Glycoprotein, M-T1, during Myxoma Virus Pathogenesis," Virology, 1999, pp. 233-245, vol. 256.
Lateef, Z. et al., "Orf virus-encoded chemokine-binding protein is a potent inhibitor of inflammatory monocyte recruitment in a mouse skin model," J. Gen. Virol., 2009, pp. 1477-1482, vol. 90.
Lateef, Z. et al., "The chemokine-binding protein encoded by the poxvirus orf virus inhibits recruitment of dendritic sells to sites of skin inflammation and migration to peripheral lymph nodes," Cell. Microbiol., 2010, pp. 665-676, vol. 12, No. 5.
Lau, E. et al., "Chemokine-Receptor Interactions: GPCRS, Glycosaminoglycans and Viral Chemokine Binding Proteins," Adv. Protein Chem., 2004, pp. 351-391, vol. 68.
Lau, E. et al., "Identification of the Glycosaminoglycan Binding Site of the CC Chemokine, MCP-1," J. Biol. Chem., May 21, 2004, pp. 22294-22305, vol. 279, No. 21.
Lawrence, M. et al., "Shape Complementarity at Protein/Protein Interfaces," J. Mol. Biol., Dec. 20, 1993, pp. 946-950, vol. 234, No. 4.
Lee, S.-J. et al., "Proliferin Secreted by Cultured Cells Bind to Mannose 6-Phosphate Receptors," J. Biol. Chem., Mar. 5, 1988, pp. 3521-3527, vol. 263, No. 7.
Liu, L. et al., "Viral Chemokine-Binding Proteins Inhibit Inflammatory Responses and Aortic Allograft Transplant Vasculopathy in Rat Models," Transplantation, Jun. 15, 2004, pp. 1652-1660, vol. 77, No. 11.
Logan, J. et al., "Adenovirus tripartite leader sequence enhances translation of mRNAs late after infection," PNAS, Jun. 1984, pp. 3655-3659, vol. 81.
Loh, J. et al., "Identification and Sequencing of a Novel Rodent Gammaherpesvirus That Establishes Acute and Latent Infection in Laboratory Mice," J. Virol., Mar. 2011, pp. 2642-2656, vol. 85, No. 6.
Lowy, I. et al., "Isolation of Transforming DNA: Cloning the Hamster aprt Gene," Cell, Dec. 1980, pp. 817-823, vol. 22.
Lubman, O. et al., "Rodent Herpesvirus Peru Encodes a Secreted Chemokine Decoy Receptor," J. Virol., Jan. 2014, pp. 538-546, vol. 88, No. 1.

\* cited by examiner

| Chemokine | $k_a (10^6) M^{-1}s^{-1}$ | $k_d (10^{-3}) s^{-1}$ | $K_{D,kin}$ (nM) | $t_{1/2}$ (s) | $K_{D,eq}$ (nM) |
|---|---|---|---|---|---|
| CCL2(mMCP-1) | 2.0 ±0.03 | 20±0.02 | 6.7±0.02 | 34.6 | 10±0.4 |
| CCL2(hMCP-1) | 1.0±0.32 | 12±0.05 | 7.5±1.2 | 2.1 | 12±0.2 |
| CCL8(mMCP-2) | 1.3±0.07 | 100±0.02 | 76±3.1 | 6.9 | 80±0.8 |
| CCL9(mMIP-1γ) | 3.6±0.63 | 10±0.01 | 4.5±1.03 | 6.8 | 1.3±0.1 |
| CCL12(mMCP-5) | 8.9±0.31 | 10±0.02 | 1.1±0.84 | 6.9 | 1.3±0.3 |
| CCL20(mMIP-3α) | 6.5±0.92 | 31±0.03 | 4.7±0.31 | 32.2 | 3.4±0.8 |
| CCL3(hMIP-1α) | n/a | n/a | n/a | >1000 | 1.4±0.8 |
| CCL3(mMIP-1α) | n/a | n/a | n/a | >1000 | 0.4±0.3 |
| CCL4(mMIP-1α) | n/a | n/a | n/a | >1000 | 0.8±0.9 |
| CCL5(mRANTES) | n/a | n/a | n/a | >1000 | 0.1±0.1 |
| CCL5(hRANTES) | n/a | n/a | n/a | >1000 | 0.9±0.9 |
| CCL24(mEotaxin-2) | n/a | n/a | n/a | >1000 | 2.2±0.1 |
| XCL1(Lymphotactin) | n/a | n/a | n/a | >1000 | 4.2±0.4 |

FIG. 2E

| Complex | $K_{D}$ (nM) | $k_{a} \times 10^{6}$ $M^{-1}s^{-1}$ | $k_{d} \times 10^{-3}$ $s^{-1}$ | $K_{D}$ (nM) |
|---|---|---|---|---|
| bioR17wt/MCP-1 | 10±0.4 | 2±0.003 | 20±0.02 | 6.7±0.02 |
| bioR17xxx/MCP-1 | 31±1.3 | 1.2±0.9 | 13.7±0.3 | 10±2.1 |
| bioR17xxx/MCP1 | 40±1.6 | 1.2±0.5 | 12±0.4 | 9.5±0.1 |
| bioR17wt/MIP-1α | 0.4±0.3 | n/a | n/a | n/a |
| bioR17xxx/MIP-1α | 0.8±0.2 | n/a | n/a | n/a |
| bioR17xxx/MIP-1α | 0.31±0.7 | n/a | n/a | n/a |

FIG. 4C

GPVGEPVASEINEASKVSSRLLTQDILFRKDRQATISLPIKLPVEDIITQTCDKITYGPLKFLDLLEKETAVLPL STDITCPACLGRAVLVGKWECPAHVAVNESDLTVFGPNKEEHVPQFVTVQQPSDGKMQRLFFAKFLGTEE SLAVLRVPGPDGHLQIQEALIHFKELSGAGVCSLWKANDSREEGLEMKQVDCLETTVLENQTCIATTLSK KIYHRLYCGERLMTGGQVSTRVLLTALGFYKROPYTFHRVPKGMVYVHLIDSGSEDYMEYSECEEVTPGRY EDKQISYTFYTDLFQTADGEPVLASVWGTSGLKDSAYESCAFVIPTKGRRKLVPRRIMSKCYPFRLTYHPST MTVRLDV RVEKHHGATDQGFVLKMES GTYSEGREYYLDRVLWGEDSSTNNVLQ

FIG. 4D

| Chemokine | $k_a$ ($M^{-1}s^{-1}$) | $k_d$ ($s^{-1}$) | $K_{D,kin}$ (nM) | $t_{1/2}$ (s) | $K_{D,eq}$ (nM) |
|---|---|---|---|---|---|
| XCL1 (lymphotactin) | $1.23 \times 10^6$ | 0.0127 | 10.4 | 54.58 | 19.16 |
| CXCL12 (hSDF-1b) | $4.36 \times 10^5$ | 0.0173 | 39.6 | 40.07 | 44.25 |
| CXCL12 (hSDF-1a) | $2.55 \times 10^7$ | 0.0343 | - | 20.24 | 39.78 |
| CXCL10 (rat IP10) | $8.12 \times 10^5$ | 0.0174 | 21.4 | 39.84 | 24.45 |
| CCL3 (mMIP-1a) | $2.35 \times 10^6$ | 0.0076 | 3.25 | 90.69 | 6.76 |
| CCL5 (mRANTES) | $2.41 \times 10^6$ | 0.0035 | 1.47 | 196.41 | 4.15 |
| CCL2 (mMCP-1) | $4.31 \times 10^5$ | $3.08 \times 10^{-3}$ | 7.15 | 224.90 | 38.86 |
| CCL8 (mMCP-2) | $1.66 \times 10^7$ | 0.0205 | 1.23 | 33.88 | 3.79 |
| CCL4 (mMIP-1b) | $8.12 \times 10^7$ | $2.12 \times 10^{-2}$ | 0.16 | 32.70 | 4.74 |
| CCL9 (mMIP-1γ) | $1.65 \times 10^6$ | 0.0298 | 18.0 | 23.26 | 39.1 |
| CCL21 (mExodus-2) | $8.51 \times 10^5$ | 0.0132 | 15.5 | 52.51 | 22.3 |
| CCL24 (mEotaxin-2) | $5.06 \times 10^5$ | $5.30 \times 10^{-3}$ | 10.5 | 130.78 | 11.9 |
| CCL11 (mEotaxin) | $1.73 \times 10^7$ | $6.37 \times 10^{-3}$ | 0.37 | 108.88 | 33.5 |
| CCL20 (mMIP-3a) | $3.42 \times 10^6$ | 0.0192 | 5.62 | 36.10 | 23.4 |
| CCL12 (mMCP-5) | $1.56 \times 10^7$ | 0.0396 | 2.54 | 17.50 | 12.3 |
| hCCL2 (hMCP-1) | $1.51 \times 10^7$ | 0.0265 | 1.76 | 26.19 | 14.9 |

CHEMOKINE DECOY RECEPTORS OF RODENT GAMMAHERPESVIRUSES AND USES THEREOF

CROSS REFERENCE TO RELATED APPLICATIONS

This application claims the benefit of International Patent Application number PCT/US2018/030022, filed Apr. 27, 2018, which claims the benefit of U.S. Provisional Application No. 62/491,083, filed Apr. 27, 2017, the disclosures of which are hereby incorporated by reference in their entirety.

GOVERNMENTAL RIGHTS

This invention was made with government support under AI019687 awarded by the National Institutes of Health. The government has certain rights in the invention.

REFERENCE TO SEQUENCE LISTING

This application contains a Sequence Listing that has been submitted in ASCII format via EFS-Web and is hereby incorporated by reference in its entirety. The ASCII copy, created on Nov. 22, 2021, is named 639591_ST25.txt, and is 11,455 bytes in size.

FIELD OF THE INVENTION

The invention generally relates to the field of immunology and specifically to chemokine binding proteins and methods of use thereof.

BACKGROUND OF THE INVENTION

The chemokine family is believed to be critically important in the infiltration of lymphocytes and monocytes into sites of inflammation. Leukocyte allograft infiltration is also required for allograft rejection. To initiate leukocyte migration, chemokines localize to allograft epithelium through specific interactions with glycosaminoglycans (GAGs), while simultaneously activating signaling cascade through specific interaction with chemokine receptors (G protein coupled receptors). Although still under examination, CCL2, CCL3 and CCL5 are considered primary inflammatory mediators that initially recruit monocytes/macrophages to the lung, leading to neutrophil infiltration into the allograft, early graft dysfunction and the overall poor graft outcome.

Solid organ, tissue, stem cell and embryonic stem cell transplantation are life-saving therapies that generally require the use of immunosuppressive medications. Chemokines recruit leukocytes to the allograft, thereby reinforcing the stress responses induced by ischemia reperfusion injury (IRI) following transplantation that may lead to transplant organ rejection. Ischemic heart diseases are one of the leading causes of death in humans in the industrialized countries. Although ischemic injury of heart tissues can be greatly recovered by rapid reperfusion, severe side effects such as cardiac over-contractile function, arrhythmia, endothelial dysfunction, and myocardial infarction often occur due to reperfusion. Moreover, endothelial dysfunction in ischemic heart tissues may lead a decrease of blood perfusion in the tissues, myocytes apoptosis, non-infectious inflammation and other complicated cardiac pathological status. Therefore, ischemia reperfusion injury represents one of the most pivotal pathological factors for organ, tissue, and cell transplantations, as well as human ischemic heart diseases.

Currently there is a need in the art for treatments ischemia reperfusion injury, chronic rejection, ischemic heart diseases, and related disorders.

SUMMARY OF THE INVENTION

Disclosed herein is a therapeutic composition containing a polypeptide that is a chemokine decoy receptor and methods of use thereof, including treating a variety of inflammatory conditions with the polypeptide.

The disclosure provides a method of preventing IRI in an organ transplanted into a subject comprising perfusing the organ with an effective amount of chemokine decoy receptor before transplanting the organ into the subject, so that IRI after organ transplant is prevented. In certain embodiments, the chemokine decoy receptor may be proteins R17, T17, or M3. The donor organ may be treated with a single decoy receptor or a combination of receptors. The treatment may prevent accumulation of at least one subset of leukocytes, wherein the subset is selected from the group consisting of neutrophils, macrophages, dendritic cells, T cells, and NK cells.

In another aspect the disclosure provides a method of treating inflammatory disorders in a subject, wherein the inflammatory disorder is characterized by accumulation of inflammatory cells, the method comprising administering a composition comprising a chemokine decoy receptor to the subject. The chemokine decoy receptor may sequester chemokines that are involved in recruitment and migration of inflammatory cells, so that the inflammatory condition is relieved.

BRIEF DESCRIPTION OF THE FIGURES

The application file contains at least one drawing executed in color. Copies of this patent application publication with color drawing(s) will be provided by the Office upon request and payment of the necessary fee.

FIG. 1A shows general chemokine binding to chemokine receptors. FIG. 1B illustrates that viral chemokines can function as agonist and antagonists as described in EBV, KSHV, HHV-6, HCMV. FIG. 1C illustrates viral chemokine receptors that can function as agonist and antagonists described in EBV, KSHV, HHV-6, HCMV. FIG. 1D illustrates viral chemokine binding protein binding to chemokines. HSV-1 protein gG (virion bound or secreted form) function as agonist HCMV-pUL21.5-CCL5 specific antagonist M3-gHV68.

FIG. 2 A, FIG. 2B, FIG. 2C, FIG. 2D and FIG. 2E show R17 binds CC and C chemokines with high affinity. (FIG. 2A and FIG. 2B) SPR sensograms of mCCL12 and hCCL2 binding to CM5 chip immobilized R17. The experimental curves (gray lines) are globally fit using a 1:1 mass transport model (black lines) to determine kinetic parameters. (FIG. 2C) Shown is a representative response curve for the saturation binding analysis of mCCL3, which cannot be accurately globally fit Saturation curve and Scatchard plot for the binding of mCCL3. FIG. 2E Tabulation of the interaction parameters for human and murine chemokines binding to R17. Reported values for ka, kd and KD,kin=kd/ka are derived from globally fit binding analysis as means±standard deviations. Reported values for KD,eq are derived from Scatchard analysis of the saturation binding analysis as means±standard deviations. The following cytokines were tested and no binding was observed under the same experimental conditions: mCCL21, mCXCL8, mCXCL10, mCXCL9, mCXCL2, mCXCL12, mCXCL1, CX3C, mIL-13, mIL-12, mIL-6, mIL-17, and mTNF-alpha.

FIG. 3C. Shown are the changes in relative fluorescence of Fura-2 loaded cells (ratio of λ340 to λ380), which monitors the intracellular $Ca^{2+}$ concentrations. Thp-1 cells were stimulated for 30 s with hCCL2 (160 nM) either alone or in complex with the following proteins: negative control MR1 (2 mM), positive control M3 (1 mM) and R17 (2 μM). $Ca^{2+}$ flux from ER was measured for 400 s followed by the addition of 1 mM $Ca^{2+}$ to measure influx. Data are representative of at least three separate experiments.

FIG. 4A, FIG. 4B, FIG. 4C and FIG. 4D show R17 interacts with cell surface GAGs at a site distinct from chemokine binding. (FIG. 4A and FIG. 4B) Flow cytometry analysis of CHO-K1 and CHO-745 cells stained by biotinylated R17 and the BBxB mutants $R17^{GAG1}$ and $R17^{GAG2}$. (FIG. 4C) SPR binding analysis of the interaction of CCL2 and CCL3 with $R17^{GAG1}$ and $R17^{GAG2}$. (FIG. 4D) Amino acid sequence of R17, the two BBXB motifs that are important for GAG binding are in blue (SEQ ID NO: 1).

(FIG. 5A) Ribbon diagram of apo R17. The N terminal domain (NTD), bridging sheet (BS) and C-terminal domain (CTD) are colored based on secondary structure: b-strands are depicted in green, α helices in cyan and connecting loops in brown. β-strands of the NTD are labeled 1-10, BS is labeled B1-B4 and β-strands of the CTD are labeled A-I. During purification, R17 was treated with EndoH to remove complex carbohydrates. Of the three predicted N-linked glycosylation sites, electron density was visible for the N-glycan linked to Asn 205. N-acetyl glucosamine (NAG) followed by a mannose ring is shown in stick representation. Disulfide bonds are shown in stick and colored yellow. (FIG. 5B) Crystal structure of the $R17^{GAG2}$ complex with murine CCL3 (D27A) at 3.0 A resolution. R17 is colored as in (A) while the chemokine is colored magenta and labeled according to accepted chemokine convention. Two NAGs linked to Asn 103 and Asn 205 are in ball and stick representation. (FIG. 5C) Displayed in white cartoon are superimposed free and ligated R17 structures. Conformational changes in the loops around chemokine binding cleft are colored green (free R17) and magenta (chemokine bound R17). Two GAG binding sites on R17 are located on the opposite surface from chemokine binding and are circled with dashed lines. (FIG. 5D) Electrostatic complementarity between R17 and CCL3. The molecular surface is colored as calculated by APBS (<−1 kT in red, 0 kt in white and >+1 kT in blue).

(FIG. 12A) T17 was first purified through a nickel column; the column was washed with 10 mM imidazole to remove unbound proteins and T17 was eluted with 250 mM imidazole. (FIG. 12B) Following nickel column purification, the eluted T17 was further purified using size exclusion chromatography. The peak corresponding to T17 runs much larger than expected (43 kDa) due to protein glycosylation. (FIG. 12C) SDS-PAGE of the size exclusion chromatography fractions of the peak confirms that T17 has been successfully purified. The purity of T17 is greater than 90% as it is the predominant protein present on the gel; the bands at higher molecular weights are aggregates of T17.

FIG. 13 lists the interaction parameters for rat, murine, and human chemokines that bind to T17. The Ka, 1Cd, and KA/an, and KD, Eq values are derived from globally fit binding analysis and averaged. We have also tested the following chemokines but observed no binding: rat CXCL4, hCX3CL1, mCXCL6, hCXCL8, mCXCL16, and rat CXCL2.

(FIG. 14A) Representative binding curves of T17 to refolded hCCL2. (FIG. 14B) Binding curves obtained from BLI of T17 to mCXCL12 shows that binding to mCXCL12 reaches saturation at 250 nM. (FIG. 14C) Representative binding curves obtained from BLI of T17 to XCL1.

(FIG. 16A) Transmigration experiments with Jurkat T cells were conducted with a constant concentration of 50 nM hCXCL12 with increasing concentrations of T17 and R17 (negative control). Error bars are based on two biological repeats. (FIG. 16B) THP-1 transmigration experiments with a constant concentration of hCCL2 (2.5 nM) and increasing concentrations of T17, R17 (positive control), and M3 (positive control) suggest that T17 is a more potent inhibitor of cell migration than M3, but weaker than R17. Error bars are generated based on at least two biological and three technical repeats

DETAILED DESCRIPTION OF THE INVENTION

Figure 1A:
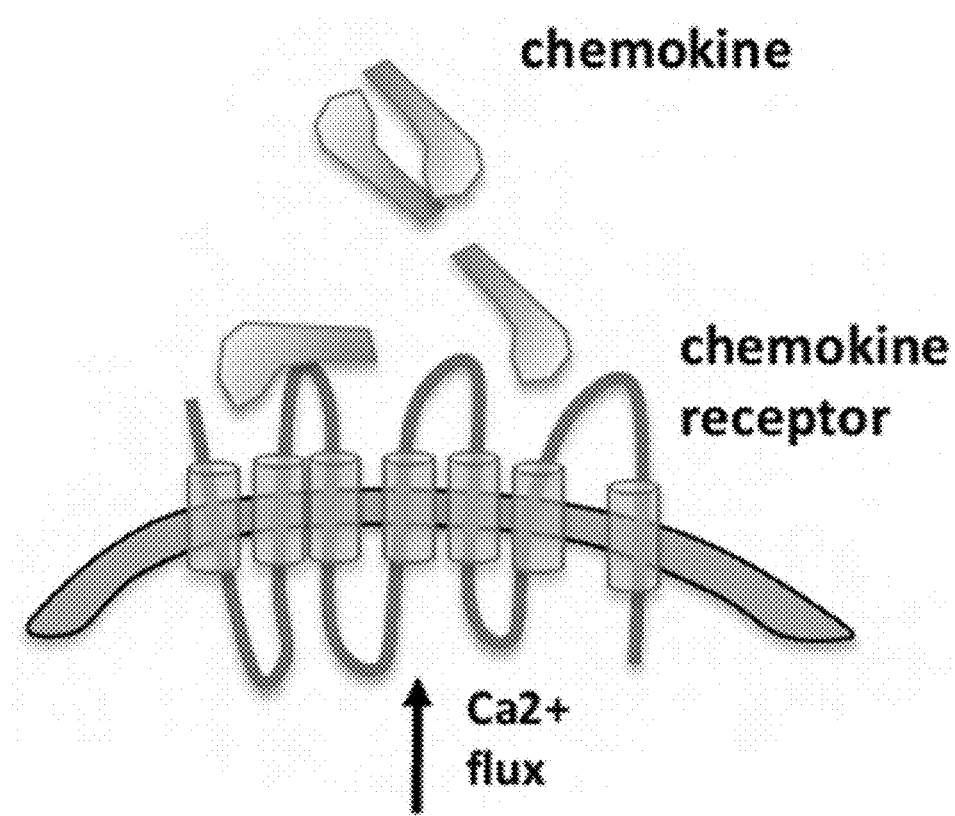
FIG. 1A, FIG. 1B, FIG. 1C and FIG. 1D illustrate the various strategies used by viruses to subvert chemokine signaling.

The present disclosure provides unique chemokine decoy receptors capable of binding an array of chemokines as well as cell surface glycosaminoglycans (GAGs). The chemokine decoy receptors may be used to treat or prevent conditions and disorders resulting from chemokine mediated infiltration of lymphocytes and monocytes into sites of inflammation. In particular, the present disclosure provides compositions and methods for improving organ, tissue, stem cell or embryonic stem cell transplantation outcome, treating and preventing ischemia reperfusion injury, ischemic heart disease and reducing immune response in a subject in need thereof. Advantageously, the binding of the chemokine decoy receptors to cell surface GAGs allows the chemokine decoy receptors to be administered and retained in specific organs, tissues or cells rather than spreading systemically. In an exemplary embodiment, the chemokine decoy receptors can be used to bind C chemokines, CC chemokines, CXC chemokines or CX3C chemokines. For instance, the chemokine decoy receptors of the disclosure may bind to, in non-limiting examples, IL-6, IL-1, IL-10, IL-12p70, IL-13, Interferons, CCL2, CCL3, CCL4, CCL5, CCL24, CXCL1, CCL21, CXCL10, CXCL12 and TNFalpha. Specifically, the chemokine decoy receptors of the disclosure bind to chemokines thereby reducing an immune response in a subject.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular.

The use of "or" means "and/or" unless stated otherwise. Furthermore, the use of the term "including," as well as other forms, such as "includes" and "included," is not limiting.

Generally, nomenclatures used in connection with, and techniques of, cell and tissue culture, molecular biology, immunology, microbiology, genetics and protein and nucleic acid chemistry and hybridization described herein are those well known and commonly used in the art. Enzymatic and staining reactions and purification techniques are performed according to manufacturer's specifications and protocols, as commonly accomplished in the art or as described herein. The nomenclatures used in connection with, and the laboratory procedures and techniques of, analytical chemistry, synthetic organic chemistry, and medicinal and pharmaceutical chemistry described herein are also those well-known and commonly used in the art.

The chemokine decoy receptors and methods of their use are described in further detail below.

(I) Chemokine Decoy Receptor Compositions

In an aspect, the present disclosure encompasses a composition comprising at least one chemokine decoy receptor. More specifically, the chemokine decoy receptors include polypeptides which bind to chemokines and cell surface GAGs. As used herein, the term "chemokine decoy receptor," refers to a receptor that binds to a chemokine ligand but that does not activate the downstream pathway activation that would be the result of the chemokine binding to the native receptor. Binding of the chemokine to the decoy receptor sequesters the chemokine, thereby preventing the chemokine from binding to the actual chemokine receptor. A decoy receptor may correspond to soluble versions of their native cellular counterparts. In some embodiments, the present disclosure provides a Rodent Herpesvirus chemokine decoy receptor polypeptide, which encodes high-affinity chemokine binding protein. In another aspect, the disclosure provides gammaherpesvirus encoded chemokine decoys with different chemokine specificity, which may be used alone or in combination with other chemokine decoy receptors. In some embodiments, the chemokine decoy receptor polypeptide disclosed herein binds to chemokines and inhibits chemokine driven functions. Unless otherwise indicated, "polypeptide" shall include a protein, protein domain, or peptide, and any fragment thereof.

According to an aspect of the present invention, the chemokine decoy receptor may be encoded by the Rodent Herpesvirus Peru (RHVP), wherein the chemokine decoy receptor is the R17 polypeptide and its functional homologues, including derivatives and fragments. In some embodiments, the chemokine decoy receptor may be encoded by the Rodent Herpesvirus Texas (RHVT), wherein the chemokine decoy receptor is the T17 polypeptide and its functional homologues, including derivatives and fragments. In still other embodiments, the chemokine decoy receptor may be encoded by MHV68, wherein the chemokine decoy receptor is the M3 polypeptide and its functional homologues, including derivatives and fragments.

Homologues of R17, T17 and M3 polypeptides can be obtained, for example, by mutation of an R17, T17 or M3-encoding nucleotide sequence, respectively, and expression from the mutated sequence and/or by use or derivation from related gene sequences. Alternatively, homologues can be obtained, for example by identifying gene sequences homologous to R17, T17 or M3 by screening databases containing either protein sequences or nucleotide sequences encoding proteins, for example using homology-based search algorithms such as those commonly known and referred to as BLAST, FASTA, and Smith-Waterman. A local sequence alignment program, e.g., BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal query is used in the present invention to filter hit sequences with significant E-values for ortholog identification. The reciprocal query entails search of the significant hits against a database of amino acid sequences from the base organism that are similar to the sequence of the query protein. A hit is a likely ortholog, when the reciprocal query's best hit is the query protein itself or a protein encoded by a duplicated gene after speciation. An acceptable level of homology over the whole sequence is at least about 20%, for example 30% homology, 40% homology, 50% homology, 60% homology, 70% homology, 80% homology, 90% homology or greater. The homology of a functional fragment of R17, T17, or M3 may be at least 10% homology. A "homologous" amino acid sequence, as used herein, refers to an amino acid sequence that differs from a reference amino acid sequence, only by one or more (e.g., 1, 2, 3, 4 or 5) conservative amino acid substitutions, or by one or more (e.g., 1, 2, 3, 4 or 5) non-conservative amino acid substitutions, deletions, or additions located at positions at which they do not adversely affect the activity of the polypeptide. For example, chemokine or GAG binding of the chemokine decoy receptors may be an activity measured. In some embodiments, such a sequence is at least 75%, 80%, 85%, 90%, or 95% or greater identical to a reference amino acid sequence.

Homologous amino acid sequences include peptide sequences that are identical or substantially identical to a reference amino acid sequence. By "amino acid sequence substantially identical" is meant a sequence that is at least 90%, preferably 95%, more preferably 97%, and most preferably 99% identical to an amino acid sequence of reference and that preferably differs from the sequence of reference, if at all, by a majority of conservative amino acid substitutions.

Conservative amino acid substitutions typically include substitutions among amino acids of the same class. These classes include, for example, (a) amino acids having uncharged polar side chains, such as asparagine, glutamine, serine, threonine, and tyrosine; (b) amino acids having basic side chains, such as lysine, arginine, and histidine; (c) amino acids having acidic side chains, such as aspartic acid and glutamic acid; and (d) amino acids having nonpolar side chains, such as glycine, alanine, valine, leucine, isoleucine, proline, phenylalanine, methionine, tryptophan, and cysteine.

According to another aspect of the invention, the chemokine decoy receptors may be mutated to modulate their chemokine or GAG binding properties. As disclosed herein, specific regions of R17 and T17 are essential for binding to chemokines. In some embodiments, when these chemokine binding regions are mutated, the binding of one or more chemokines to the chemokine decoy receptor may be reduced. In alternative embodiments, mutation of the R17 or T17 chemokine binding regions may increase the binding of one or more chemokines to the decoy receptor. In non-limiting examples, residues that may modulate chemokine binding properties of R17 include Cys 81, Pro82, Ala83, Cys84, Glu145, Val195, Asp196, Cys197, Leu198, Glu199, Thr200, Thr201, Val 202, Leu203, Ser 214, Leu221, Met228, Leu 239, Tyr245, Val262, His263, Leu264, Ile265, Asp266, Ser267, Gly268, Ser269, Glu270, Asp271, Tyr272, Glu274, Tyr275, Glu280, Trp313, Thr315, Gly317, Leu318, Lys319, Asp320, Thr374, Gln376, Phe378, Phe380, Glu393, and Tyr395. In some embodiments, the structurally equivalent chemokine binding residues that may modulate chemokine binding properties of T17 include: Cys61, Tyr62, Ser63, Cys64, Glu123, Leu173, Ala174, Cys175, Pro176, Gly177, Ala178, Gly179, Gly180, Leu181, Ser192, Phe199, Ile206, Thr217, Val233, His234, Leu235, Ile236, Asp237, Ser238, Gly239, Ser240, Tyr240, Glu241, Pro242, Asp244, Asp245, Glu250, Tyr282, Thr284, Asp286, Ser287, Ser288, Ser344, Gln346, Tyr348, Phe350, Asp364, and Tyr363

The chemokine binding properties of a chemokine decoy receptor may be measured using assays described herein, for example those discussed in the examples.

In an aspect, a R17 chemokine decoy receptor of the disclosure may comprise the amino acid sequence set forth in SEQ ID NO: 1 (GPVGEPVASEINEAS-KVSSRLLTQDILFRKDRQATISLPIKLPVEDIITQTCD-KITYGPLK FLDLLEKETAVLPLSTDITCPACL-GRAVLVGKWECPAHVAVNESDLTVFGPNKEEHVP QFVTVQQPSDGKMQRLFFAKFLGTEE-SLAVLRVPGPDGHLCIQEALIHFKELSGAGVC SLW-KANDSREEGLEMKQVDCLETTVLENQTCIATTLSK-KIYHRLYCGERLMTGGQVST RVLLTALGFYKRQPY-TFHRVPKGMVYVHLIDSGSEDYMEYSE-CEEVTPGRYEDKQISY TFYTDLFQTADGEPV-LASVWGTSGLKDSAYESCAFVIPTKGRRKLVPRRI-MSKCYPFR LTYHPSTMTVRLDVRVEKHH-GATDQGFVFLKMESGTYSEGREYYLDRVLWGED-SSTN NVLQ). In another aspect, a R17 chemokine decoy receptor of the disclosure may comprise an amino acid sequence with 80% identity, 81% identity, 82% identity, 83% identity, 84% identity, 85% identity, 86% identity, 87% identity, 88% identity, 89% identity, 90% identity, 91% identity, 92% identity, 93% identity, 94% identity, 95% identity, 96% identity, 97% identity, 98% identity, 99% identity to SEQ ID NO:1.

In still another aspect, a T17 chemokine decoy receptor of the disclosure may comprise the amino acid sequence set forth in SEQ ID NO: 2 (AEKEVTNSKLDTLDG-KYLTQTIESKRRKPGVPLPVNGTVEDLLKRSCD-KITHGPLKSIL LHEKYVYVLPVKHDPTCYSCK-SSGVLVAQWSCPPDVSVNEQEVSMIVPEHEEFTPYF KTVTGAAGEERVFYVGYQALENSALVIKVPAP-DGPKCLQKIMVWYNDKTGAGMCGKF SQGIDHQDGFNVSELACPGAGGLLD-VACVNVQGKTKLNQQFFCGTKPIGASSILFTSL TVAIGKTCVNGKDVLVDLIDSADYEPMDDEECEE-ITSGTWTKNVISYEFETSIFQETKQP VLVTVY). In another aspect, a T17 chemokine decoy receptor of the disclosure may comprise an amino acid sequence with 80% identity, 81% identity, 82% identity, 83% identity, 84% identity, 85% identity, 86% identity, 87% identity, 88% identity, 89% identity, 90% identity, 91% identity, 92% identity, 93% identity, 94% identity, 95% identity, 96% identity, 97% identity, 98% identity, 99% identity to SEQ ID NO:2.

In still yet another aspect, a M3 chemokine decoy receptor of the disclosure may comprise the amino acid sequence set forth in SEQ ID NO: 3 (LTLGLAPAL-STHSSGVSTQSVDLSQIKRGDEIQAHCLTPAETE-VTECAGILKDVLSKNL HELQGLCNVKNKMGVPWVSVEELGQEIIT-GRLPFPSVGGTPVNDLVRVLVVAESNTPE ETPEEEFYAYVELQTE-LYTFGLSDDNWFTSDYMTVWMIDIPKSYVDVGML- TRATFLE QWPGAKVTVMIPYSSTFTWCGELGAISEE-
SAPQPSLSARSPVCKNSARYSTSKFCEV
DGCTAETGME-
KMSLLTPFGGPPQQAKMNTCPCYYKYSVSPL-
PAMDHLILADLAGLDS LTSPVYVMAAYFDSTHEN-
PVRPSSKLYHCALQMTSHDGVWTSTSSEQCPIRL-
VEGQS QNVLQVRVAPTSMPNLVGVSLMLEGQQYR-
LEYFGDH).

In another aspect, a M3 chemokine decoy receptor of the disclosure may comprise an amino acid sequence with 80% identity, 81% identity, 82% identity, 83% identity, 84% identity, 85% identity, 86% identity, 87% identity, 88% identity, 89% identity, 90% identity, 91% identity, 92% identity, 93% identity, 94% identity, 95% identity, 96% identity, 97% identity, 98% identity, 99% identity to SEQ ID NO:3.

Another aspect of the present disclosure provides nucleic acids encoding the chemokine decoy receptors described herein. The nucleic acid can be DNA or RNA. In one embodiment the DNA can be present in a vector. The nucleic acid sequences which encode the reporter molecule of the invention can be operatively linked to expression control sequences. "Operatively linked" refers to a juxtaposition wherein the components so described are in a relationship permitting them to function in their intended manner. An expression control sequence operatively linked to a coding sequence is achieved under conditions compatible with the expression control sequences. As used herein, the phrase "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, and maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific expression, tissue-specific expression, or expression inducible by external signals or agents; such elements may be located in the 5' or 3' regions of the gene. Both constitutive and inducible promoters, are included in the invention (see e.g., Bitter et al., Methods in Enzymology 153:516-544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In some embodiments, the nucleic acid sequences encoding a chemokine receptor of the invention may be inserted into a recombinant expression vector. The term "recombinant expression vector" refers to a plasmid, virus or other vehicle known in the art that has been manipulated by insertion or incorporation of the nucleic acid sequences encoding the fusion peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 263:3521, 1988), baculovirus-derived vectors for expression in insect cells, cauliflower mosaic virus, CaMV; or tobacco mosaic virus, TMV. The nucleic acid sequences encoding a chemokine decoy receptor as described herein can also include a localization sequence to direct the indicator to particular cellular sites by fusion to appropriate organellar targeting signals or localized host proteins. A polynucleotide encoding a localization sequence, or signal sequence, can be used as a repressor and thus can be ligated or fused at the 5' terminus of a polynucleotide encoding the reporter polypeptide such that the signal peptide is located at the amino terminal end of the resulting fusion polynucleotide/polypeptide. The construction of expression vectors and the expression of genes in transfected cells involve the use of molecular cloning techniques also well known in the art. Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989).

Depending on the vector utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516-544, 1987). These elements are well known to one of skill in the art.

By "transformation" is meant a permanent genetic change induce in a cell following incorporation of new DNA (i.e., DNA exogenous to the cell). Where the cell is a mammalian cell, the permanent genetic change is generally achieved by introduction of the DNA into the genome of the cell.

Transformation of a host cell with recombinant DNA may be carried out by conventional techniques well known to those skilled in the art. Where the host is prokaryotic, such as E. coli, competent cells which are capable of DNA uptake can be prepared from cells harvested after exponential growth phase and subsequently treated by the $CaCl_2$) method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transfected with DNA sequences encoding the reporter molecules of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*), or may be a mammalian cell. In one embodiment, the mammalian cell is a human cell.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to CHO, VERO, BHK, HeLa, COS, MDCK, Jurkat, HEK-293, and W138. In one embodiment, the eukaryotic cell is a human cell.

Mammalian cell systems which utilize recombinant viruses or viral elements to direct expression may be engineered. For example, when using adenovirus expression vectors, the nucleic acid sequences encoding a chemokine decoy receptor of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fluorescent indicator in infected hosts (e.g., see Logan & Shenk, Proc. Natl. Acad. Sci. USA, 81:3655-3659, 1984). Alternatively, the vaccinia virus 7.5K promoter may be used. (e.g., see, Mackett, et al., Proc. Natl. Acad. Sci. USA, 79:7415-7419, 1982; Mackett, et al., J. Virol. 49:857-864, 1984; Panicali, et al., Proc. Natl. Acad. Sci. USA 79:4927-4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone & Mulligan, Proc. Natl. Acad. Sci. USA, 81:6349-6353, 1984). High level expression may also be achieved using inducible promoters, including, but not limited to, the metallothionine IIA promoter and heat shock promoters.

For long-term, high-yield production of recombinant proteins, stable expression may be preferred. Rather than using expression vectors which contain viral origins of replication, host cells can be transformed with the cDNA encoding a chemokine decoy receptor of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk-, hgprt- or aprt-cells respectively. Also, antimetabolite resistance can be used as the basis of selection for dhfr, which confers resistance to methotrexate (Wigler, et al., Proc. Natl. Acad. Sci. USA, 77:3567, 1980; O'Hare, et al., Proc. Natl. Acad Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al, J. Mol. Biol 150:1, 1981); and hygro, which confers resistance to hygromycin (Santerre, et al., Gene 30: 147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

A chemokine decoy receptor as described herein can be produced by expression of nucleic acid encoding the chemokine decoy receptor protein in prokaryotes. These include but are not limited to microorganisms such as bacteria transformed with recombinant bacteriophage DNA, plasmid DNA or cosmid DNA expression vectors encoding a chemokine decoy receptor. The constructs can also be expressed in *E. coli* in large scale. Purification from bacteria is simplified when the sequences include tags for one-step purification by nickel-chelate chromatography. The construct can also contain a tag to simplify isolation of the fluorescent indicator. For example, a polyhistidine tag of, e.g., six histidine residues, can be incorporated at the amino terminal end of the fluorescent protein. The polyhistidine tag allows convenient isolation of the protein in a single step by nickel-chelate chromatography. The chemokine decoy receptor of the invention can also be engineered to contain a cleavage site to aid in protein recovery.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

A composition of the present disclosure may optionally comprise one or more additional drug(s) or therapeutically active agent(s) in addition to the chemokine decoy receptor. A composition of the invention may further comprise a pharmaceutically acceptable excipient, carrier, or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents, or antioxidants.

(II) Pharmaceutical Compositions

Another aspect of the present disclosure provides pharmaceutical compositions. The pharmaceutical compositions comprise at least one chemokine decoy receptor and at least one pharmaceutical acceptable excipient.

The pharmaceutically acceptable excipient may be a perfusion solution, a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

(i) Perfusion Solution

In some embodiments, the excipient may be a perfusion solution. Perfusion solutions generally consist of saline solutions of varying osmolality, with certain solutions being better for specific organs. The skilled artisan can readily determine desired components of a perfusion solution which are selected in an organ specific manner. Non-limiting examples of suitable perfusion solutions include EuroCollins, UW (Viaspan, Celsior, Custodiol, IGL-1 and Belzer UW.

(ii) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(iii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

(iv) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(v) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(vi) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vii) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(viii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(ix) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(x) Lubricant

In a further embodiment, the excipient may be a lubricant. Non-limiting examples of suitable lubricants include minerals such as talc or silica; and fats such as vegetable stearin, magnesium stearate, or stearic acid.

(xi) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xii) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xiii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(a) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration may include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising at least one chemokine decoy receptor is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of at least one chemokine decoy receptor in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, at least one chemokine decoy receptor may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying at least one chemokine decoy receptor may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of the chemokine decoy receptor, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatters of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. At least one chemokine decoy receptor may be encapsulated in a microemulsion by any method generally known in the art.

In yet another embodiment, at least one chemokine decoy receptor may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(ii) Dosage

Dosages of the pharmaceutical compositions can vary between wide limits, depending upon the disease or disorder to be treated, the age of the subject, and the condition of the subject to be treated. In an embodiment, the amount of the chemokine decoy receptor in the pharmaceutical composition is an amount to effectively reduce chemokine mediated leukocyte infiltration.

(iii) Subject

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas, and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

(III) Methods

In an aspect, the present disclosure provides chemokine decoy receptors for use in inhibiting the binding of such chemokines to their receptors, whether in vitro, in vivo, or ex vivo. In another aspect, the present disclosure provides methods of reducing immunopathological disorders in a subject. In some embodiments, the chemokine related immunopathological disorders are those having an etiology associated with an influx of leukocytes, wherein the chemokine belongs to CC or CXC or C family and may be treated by administering a chemokine decoy receptor. In some embodiments the chemokine decoy receptor may be used to treat autoimmune diseases, treat or prevent ischemia reperfusion injury, or treat or prevent post myocardial infarction ischemic heart disease. Suitable chemokine decoy receptors are disclosed herein, for instance those described in Section I.

In some embodiments, polypeptides suspected of being members of a chemokine family can be screened using the chemokine decoy receptors as described herein. In one embodiment, the invention provides a method of screening and identifying novel chemokines comprising contacting at least one free or matrix-bound chemokine decoy receptor of the invention with a composition suspected of containing one or more chemokines and detecting binding of the chemokine decoy receptor to the composition. Methods for detecting binding of the chemokine decoy receptor to the composition (chemokine) will be known to those of skill in the art and include those described in the examples herein. In some embodiments, various labels maybe used as means for detecting binding of a chemokine decoy receptor to a chemokine. Chemokines may be directly or indirectly labeled, in non-limiting examples, with a radioisotope, a fluorescent compound, a bioluminescent compound, a chemiluminescent compound, a metal chelator or an enzyme. Those of ordinary skill in the art will know of other suitable labels or will be able to ascertain such, using routine experimentation.

The term "chemokine" as used herein, refers to a molecule with chemo attraction properties. Chemokines are a group of small cytokines that orchestrate host defense against microorganisms in vertebrates. The role of chemokines in orchestrating host defenses is well established, with one hallmark being the establishment of concentration gradients that guide immune responder cells toward sites of infection or tissue damage. Pro-inflammatory chemokines play an essential role in the clearance of a broad array of pathogens through the recruitment of effector leukocytes. Chemokines establish gradients through specific interactions with glycosaminoglycans (GAGs), and direct target cell migration and activation by binding to G-protein-coupled chemokine receptors. Non-limiting examples of chemokines may include IL-6, IL-1, IL-10, IL-12p70, IL-13, Interferons, CCL2, CCL3, CCL4, CCL5, CCL24, CXCL1, CXCL21, CXCL10, CXCL12 and TNF alpha.

According to another aspect of the invention a pharmaceutical composition comprising at least one chemokine decoy receptor described herein, as mentioned above, can be used as an anti-inflammatory agent. Thus, the chemokine decoy receptors as described herein may be used in a method to treat or prevent an inflammatory disorder. An "inflammatory disorder", as used herein, is a condition that is characterized by inflammation. The injury may be caused by physical, chemical, or biological agents. The response may involve secretion of cytokines, including chemokines, and migration of leukocytes to the site of injury. The method generally comprises administering to a subject a pharmaceutical composition comprising a therapeutically effective amount of at least one chemokine decoy receptor. In some embodiments, the inflammatory disorder is characterized by accumulation of inflammatory cells. In some embodiments, the method comprises administering a composition comprising at least one chemokine decoy receptor to the subject, wherein the chemokine decoy receptor sequesters chemokines that are involved in recruitment and migration of inflammatory cells, so that the inflammatory condition is relieved. In some embodiments, the chemokine decoy receptor includes at least one GAG binding site and at least one chemokine binding site. In some embodiments, the chemokine decoy receptor is selected from the group consisting of R17, M3, T17 and combinations thereof. In some embodiments the chemokine decoy receptor is mutated to modulate the chemokine binding properties.

In some embodiments, the methods of the invention provide a chemokine decoy receptor of the present invention used in combination with one or more of a nonsteroidal anti-inflammatory agent, a steroidal anti-inflammatory agent, an immune suppressant, an antihistamine, an antirheumatic drug and a biological preparation such as infliximab, adalimumab, tocilizumab, etc. Non-limiting examples of suitable nonsteroidal anti-inflammatory agents may include indomethacin, ibuprofen, diclofenac, and aspirin. Non-limiting examples of suitable steroidal anti-inflammatory agents may include dexamethasone, betamethasone, prednisolone, and triamcinolone. Non-limiting examples of suitable immunosuppressants may include tacrolimus, cyclosporine, and sirolimus. Non-limiting examples of suitable antihistamines may include diphenhydramine, chlorpheniramine, triprolidine, promethazine, alimemazine, hydroxyzine, cyproheptadine, fexofenadine, olopatadine, epinastine, loratadine, cetirizine, bepotastine, and mequitazine. Non-limiting examples of suitable antirheumatic drugs may include bucillamine, salazosulfapyridine, and methotrexate.

In another aspect, the disclosure provides a method to prevent or treat an inflammatory condition associated with an organ transplant, tissue transplant, stem cell transplant or embryonic stem cell transplant. The method generally comprises contacting the transplant organ, tissue, or cells with at least one chemokine decoy receptor. In some embodiments, contacting occurs before, during or after transplantation. In some embodiments, chemokine decoy receptor sequesters chemokines that are involved in recruitment and migration of inflammatory cells, so that the inflammatory condition associated with the transplantation is relieved. In some embodiments, at least one chemokine decoy receptor is added to a perfusion solution which is used to contact the transplant organ, tissue, or cell. In some embodiments, the inflammatory condition associated with transplantation is ischemia-reperfusion injury (IRI). The phrase "ischemic reperfusion injury," as used herein, refers to the injury that results when a tissue is deprived of oxygen, and after a period, reoxygenated by returning the blood supply to the tissue. The deprivation of oxygen may cause injury to the vasculature of the tissue that may release inflammatory molecules, including chemokines that attract inflammatory cells to the site resulting in inflammation and further damage to the reoxygenated site. Ischemia reperfusion injury may be "prevented" by intervening before the injury occurs, such that no damage to the tissue occurs, or by mitigating the damage by treating the tissue before, during, or after IRI.

"Organ," as used herein, refers to a human or animal organ that is supplied by blood and is oxygenated by the blood supply. The organ may be capable of being transplanted from a donor human or animal to a recipient human or animal. Suitable organs may include lung, heart, liver, kidney, pancreases, intestines, thymus, and skin. Generally speaking, the organ will have a circulatory system, through which it may be perfused.

"Perfusion," as described herein, refers to passing a fluid through the circulatory system of an organ. The perfusion may deliver nutrients including oxygen to the organ or flush out elements from the organ.

"Reperfusion," as used herein, refers to the process whereby blood flow (or other oxygenated fluid) is returned to an oxygen deprived organ, thus reoxygenating the organ. Reperfusion may be performed with reperfusion solutions. Generally speaking, reperfusion may be performed for at least about 10 minutes to about 24 hours.

As used herein, the term "transplantation" refers to the process of taking a cell, tissue, or organ, called a "transplant" or "graft" from one individual and placing it or them into a (usually) different individual. The individual who provides the transplant is called the "donor" and the individual who received the transplant is called the "host" (or "recipient"). If the transplant occurs within the same individual, then there is a donor site (site that provides the transplant) and recipient, or graft, site (site that receives the transplant). An organ, or graft, transplanted between two genetically different individuals of the same species is called an "allograft". A graft transplanted between individuals of different species is called a "xenograft". The organ transplant tissue itself is typically human in origin, but may also be from another species such as the rhesus monkey. The organ that has been deprived of oxygen may be a donor organ. The loss of blood flow through the organ may trigger vascular changes that induce release of chemokines in the deprived donor organ.

The donor organ, tissue or cells may be reperfused with a reperfusion solution before, during or after transplantation. The reperfusion solution may include a chemokine decoy receptor composition. The reperfusion with a solution including a chemokine decoy receptor composition may be performed from about 5 minutes to up to about 24 hours before transplanting the organ into a recipient. In some embodiments, the reperfusion with a solution including a chemokine decoy receptor composition may be performed from about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes before transplanting the organ, tissue or cells into a recipient. In some embodiments, the reperfusion with a solution including a chemokine decoy receptor composition may be performed from about 1, 2, 3, 4, 5, 6, 7, 8, 9, 10, 11, 12, 13, 14, 15, 16, 17, 18, 19, 20, 21, 22, 23, or 24 hours before transplanting the organ, tissue or cells into a recipient.

The donor may be human or animal. The donor may be a live donor or a cadaver. The recipient may be a human or animal.

The term "wild type" or "WT," as used herein, refers to an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

Ischemia/reperfusion injury (IRI) occurs as an inevitable consequence of the transplant process, beginning with organ procurement and preservation and followed by reperfusion of the donor organ with recipient blood during transplant. IRI leads not only to early graft dysfunction and acute rejection, but also contributes to poor long-term graft outcome. Currently, there is no FDA approved treatment that prevents or effectively resolves IRI or chronic rejection. After reperfusion, activated monocytes/macrophages and parenchymal cells secrete chemokines and other inflammatory mediators inducing neutrophil infiltration.

In an aspect, the chemokine decoy receptors described herein may act locally by binding to extracellular matrix proteoglycans to sequester a broad spectrum of proinflammatory chemokines involved in leukocyte recruitment. The decoy receptors described herein may bind a diverse set of human chemokines with affinities 10-1000 fold higher than any endogenous chemokine-GPCR pair, making them naturally affinity matured biotherapeutics.

In an aspect, potential immunogenicity issues associated with non-human proteins may be minimized. A single regiment, reperfusion of a donor lung with chemokine decoy receptor prior to transplant may endow immune privilege to the allograft. This, regiment may not be significantly immunogenic.

For IRI blood oxygenation a $PaO_2$ of greater than 300 mm Hg may be used. For transplant tolerance standard of care biopsies may be analyzed for histological signs of rejection and the maintenance of 90% peak lung function.

In an aspect, the importance of chemokines for immune cell infiltration into an organ or tissue may be identified. For example, in lungs, as in many other organs, it remains unclear if measuring chemokine levels without characterizing and quantifying what is directly bound to the extracellular matrix has any functional relevance as inflammatory cells traffic towards local chemokine gradients attached to GAGs.

In an aspect, peptides that are mutants of R17, T17 or M3 may be administered to the subject. The mutation may be a direct mutation. The mutation may enhance the binding properties of the chemokine decoy receptor. In some embodiments, the mutation may reduce the binding properties of the chemokine decoy receptor.

In another aspect, the disclosure provides a method to prevent or treat ischemic heart disease in a subject. The method generally comprises administering to the subject a composition comprising a therapeutically effect amount of at least one chemokine decoy receptor. "Ischemic" means that an organ (such as the heart or lung) is not getting enough blood and oxygen. Ischemic heart disease is a term that doctors use to describe patients who have congestive heart failure due to coronary artery disease. Ischemic heart disease results when the arteries that bring blood and oxygen to the heart are blocked. There may be a build-up of cholesterol and other substances, called plaque, in the arteries that bring oxygen to heart muscle tissue. Ischemic heart disease is a common cause of congestive heart failure. Patients with this condition may at one time have had a heart attack, angina, or unstable angina. A few patients may not have noticed any previous symptoms. Ischemic heart disease is a common type of cardiomyopathy in the United States and affects approximately 1 out of 100 people, most often middle-aged to elderly men.

Risks for ischemic heart disease include, but are not limited to, personal or family history of heart attack, angina, unstable angina, atherosclerosis, or other coronary artery diseases, high blood pressure, smoking, diabetes, high fat diet, high cholesterol, and obesity.

Symptoms of ischemic heart disease include, but are not limited to, chest pain that is localized under the chest bone but may move (radiate) to the neck, jaw, back, shoulder, arm accompanied by a tight, pressure, crushing, and/or squeezing feelings (the pain may or may not be relieved by rest or nitroglycerin), palpitations, irregular or rapid pulse, shortness of breath, cough, fatigue, weakness, faintness, decreased alertness or concentration, decreased daytime urine output, excessive urination at night, and overall swelling.

Tests measuring ejection fraction may be used to diagnose ischemic heart disease that includes, but are not limited to, echocardiogram, ventriculogram performed during a cardiac catheterization, gated SPECT, MRI of chest, ECG, or heart biopsy.

The goal of current treatments is to relieve symptoms and treat the cause of the condition. Several types of medications are currently prescribed, including, but not limited to, angiotensin converting enzyme inhibitors (e.g., captopril or lisinopril), beta-adrendergic blockers (e.g., metoprolol or carvedilol), or diuretics (e.g., furosemide (Lasix), spironolactone, or eplerenone. The methods described herein can include the use of such treatments in combination with a chemokine decoy receptor, administered separately or in a single composition.

The methods described herein include the treatment of ischemia-reperfusion associated diseases including myocardial ischemia, cerebral ischemia, and renal ischemia. For example, in subjects with or at risk of myocardial ischemia, the methods can be used to reduce myocardial damage during a cardiac procedure, e.g., cardiac transplant, percutaneous coronary intervention (PCI), or coronary artery bypass graft (CABG), and for acute protection against myocardial damage during periods of unstable angina. The methods can include administration of a composition comprising a therapeutically effective amount of at least one chemokine decoy receptor in subjects with established coronary artery disease. In subjects with or at risk of kidney ischemia, compositions comprising the chemokine decoy receptors of the invention can be used to reduce acute kidney injury (AM) during CABG, and to reduce transplant injury. When a subject is about to undergo a procedure that carries a risk of ischemia-reperfusion damage the chemokine decoy receptor composition can be administered prior to, during, or after the procedure.

Thus the compositions identified by a method described herein as comprising at least one chemokine decoy receptor, are suitable for treating ischemic disorders including, but not limited to, stroke, ischemic heart disease (e.g., heart attack or angina pectoris), reperfusion injury.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

INTRODUCTION FOR EXAMPLES

Rodent herpesvirus Peru (RHVP) was originally isolated from a lung homogenate of a pygmy rice rat (*Oligoryzomys microtis*) trapped in Peru (1). RHVP can establish latent infection in B6 and 129 mice, with lethal infections observed in mice lacking interferon responses and/or B and T cells. The genome of RHVP carries all of the conserved open reading frames (ORFs) found in other rhadinoviruses, such as murine gammaherpesvirus 68 (MHV68) and Kaposi's sarcoma-associated herpesvirus (KSHV), as well as at least 18 unique ORFs that are not broadly conserved among other gammaherpesviruses. To date, the only functionally characterized protein encoded by RHVP is R12 (pK3), a transmembrane ubiquitin ligase similar to those found in MHV68 and KSHV that downregulates major histocompatibility complex class I (MHC-I) surface expression in a unique manner. Sequence analysis of RHVP R5, R6, R7, R17, and R18 is consistent with them encoding secreted, extracellular proteins; all contain leader peptides and lack both transmembrane regions and intracellular localization motifs. Our key hypothesis was that these secreted proteins function to subvert host defense.

Most of the damage inflicted on virally infected cells is the result of activities initiated by proinflammatory cytokines, such as interleukin 1 (IL-1), tumor necrosis factor alpha (TNF-$\alpha$), and the interferons. Not surprisingly, these and related factors are favorite targets for viral sabotage. An immune evasion strategy commonly employed by large-DNA viruses is based on the secretion of high-affinity binding proteins that act as cytokine scavengers. Frequently, these decoy receptors correspond to soluble versions of their host cellular counterparts. For example, orthopoxviruses encode a secreted protein with ~25% sequence similarity to mammalian gamma interferon (IFN-$\gamma$) receptors that binds and functionally inhibits IFN-$\gamma$. The gammaherpesvirus Epstein-Barr virus (EBV) encodes a secreted decoy that binds colony-stimulating factor 1 (CSF-1), impairing macrophage differentiation, function, and survival.

The role of chemokines in orchestrating host defenses is well established, with one hallmark being the establishment of concentration gradients that guide immune responder cells toward sites of infection. A wide variety of secreted chemokine binding proteins with the ability to subvert chemokine signaling have been identified, including those encoded by schistosoma parasites, bloodsucking ticks, and herpes- and poxviruses. The M3 protein of MHV68 is abundantly secreted during infection and is capable of promiscuously sequestering members of all four chemokine classes with subnanomolar affinities. Functional and structural studies indicate that M3 potently blocks chemokine receptor interactions by competitive inhibition and disrupts chemokine gradients by electrostatically mimicking glycosaminoglycans (GAGs). Other reported herpesvirus proteins that bind chemokines include the human cytomegalovirus (HCMV)-encoded pUL21.5 decoy receptor that has exquisite specificity for human CCL5, binding with high affinity and effectively blocking chemokine receptor activation. In contrast to the chemokine decoy receptors encoded by MHV68 and HCMV, the herpes simplex virus 1 (HSV-1)- and HSV-2-encoded gG protein appears to bind chemokines via their GAG binding regions and has been reported to enhance chemotaxis, perhaps to recruit cells pertinent to viral infection or spread.

Poxviruses encode a number of distinct chemokine binding proteins. The first group characterized has been termed vCCI (also called M-T1/35k/vCKBP) and refers to abundantly secreted glycoproteins expressed early during viral infection that bind selectively to CC and some CXC chemokines with high affinity (0.03 to 100 nM), blocking their activity. The second group includes vaccinia A41 and ectromelia E163, which are structurally similar to vCCI but appear mechanistically distinct. Chemokine mutational analysis was used to demonstrate that A41 binds directly to the GAG recognition regions of chemokines; however, these proteins are ineffective in blocking chemotaxis. In addition to blocking chemokine-GAG interactions, E163 itself can tightly associate with GAGs. Thus, it appears that these poxvirus proteins may modulate chemokine networks through the disruption of chemokine gradients rather than the competitive inhibition of chemokine receptor binding. Although distinct from A41 and E163, myxoma virus encodes M-T7, a secreted glycoprotein that functions both as a species-specific inhibitor of rabbit IFN-γ and as a chemokine binding protein. Another group of poxvirus-encoded chemokine binding proteins that have been characterized are termed SECRET domains. Chemokine binding studies of the SECRET domains from variola, ectromelia, and cowpox suggest that all of these decoy receptors bind a similar set of chemokines with low nanomolar affinities, including both human and mouse CCL28, CCL25, CXCL12b, CXCL13, and CXCL14 and the mouse chemokines CCL27 and CXCL11. Further, the binding of SECRET domains to the murine chemokine CCL25 was shown to block chemotaxis, suggesting that the function of these proteins may be more similar to vCCI discussed above rather than A41 that blocks only chemokine-GAG interactions.

Poxvirus vCCIs are thought to be involved in regulating inflammation during acute infection. Myxoma viruses deficient in M-T1(vCCI) have a subtle phenotype, with an increase in leukocyte infiltration but no significant difference in disease progression or mortality (18, 25). In addition, mouse studies of ORF virus infection, a zoonotic parapoxvirus, shown to encode vCCI-like chemokine binding protein (26), demonstrated that ORF virus (ORFV) vCCI blocks the recruitment of immature and mature dendritic cells to the skin and lymph nodes and inhibits T cell responsiveness in lymph nodes (26, 27). The role of herpesvirus-encoded chemokine binding proteins in pathogenesis and immune modulation remains poorly understood, in part due to lack of the appropriate experimental host. For example, inactivation of M3 expression (by insertion of a translational stop codon) has no apparent consequence on MHV68 infection following intranasal inoculation of C57BL/6 mice (28). Intracerebral injection of the same M3 mutant virus does lead to an altered inflammatory response, with higher numbers of infiltrating lymphocytes and macrophages than observed following inoculation with the wild-type virus (28). However, M3 contributes significantly to MHV68 pathogenesis in a natural host, wood mice, where lack of M3 resulted in substantially reduced latency in the spleen and lung (29, 30).

Despite genetic similarity with MHV68, we have been unable to identify a protein with sequence similarity to the M3 chemokine decoy receptor in the RHVP genome. However, given the recurrence of chemokine binding proteins encoded by diverse large-DNA viruses, we hypothesized that RHVP acquired an alternative approach for disrupting chemokine-induced infiltration of inflammatory cells. Herein, we have examined five secreted proteins encoded by RHVP with the hypothesis that one or more would function as a cytokine decoy receptor. Using cytokine arrays as a screen, we identified R17 as a potential chemokine binding protein. Indeed, R17 binds members of two of the four chemokine families (CC and C), with ligand binding characterized by nanomolar affinities. We show that engagement of chemokines by R17 blocks their ability to signal through host chemokine receptors and thereby disrupts chemotaxis.

We also found that R17 can enhance the association of chemokines with cell surfaces, an observation that we demonstrate is due to the ability of R17 to bind GAGs.

Chemokine binding profile for T17 which interacts with CC, some CXC and C chemokines was determined. Flow cytometry experiments demonstrate that in addition to chemokine binding, T17 also binds cell surface GAGs. T17 acts as an antagonists blocking chemotaxis of human Jurkat T cells to CXCL12 and as well as human monocytes in response to CCL2.

METHODS FOR EXAMPLES

Cloning, Expression, and Purification of RHVP-Encoded Proteins

The SignalP 4.1 server predicted the following signal peptide cleavage sites for the secreted proteins of interest: R5 (UnitPro E9M5I4) between Ser 50 and Val 51, R6 (UnitPro E9M5I5) between Gly 22 and Phe 23, R7 (UnitPro E9M5I7) between Ala 18 and Arg 19, R17 (UnitPro E9M5R0) between Cys 27 and Gly 28, and R18 (UnitPro E9M5R1) between Gly 14 and Gln 15. Mature forms of R5, R6, R7, R17, and R18 ORFs without leader peptide were amplified from RHVP virus genomic DNA (accession number NC_015049) and cloned into mammalian expression vector pHLsec (Invitrogen) in frame with the CD33 leader peptide sequence MPLLLLLPLLWAG (SEQ ID NO: 5) as either C-terminal Fc fusion or C-terminal 8-His fusion proteins (SEQ ID NO: 6). Fc fusion proteins were used in the Bio-Plex cytokine arrays. All other assays were performed using R17-His. In this expression vector, the desired gene is under the control of a CMV promoter with a multiple cloning site and an SV40 poly(A) signal. This plasmid carries the origin of replication (oriP) and expresses the EBNA-1 protein from the Epstein-Barr virus that allows long-term episomal maintenance and translocation of the plasmid into the nucleus to enhance protein expression. All constructs were transiently expressed in HEK293F cells in suspension using 293fectin (Invitrogen) as a transfection reagent and grown in Invitrogen's serum-free FreeStyle medium. The culture medium was collected 10 days after transfection, and RHVP-carried ORFs were purified by standard protein A affinity chromatography in accordance with the manufacturer's protocol (GE Healthcare, Piscataway, N.J.) and were subsequently buffer exchanged into phosphate-buffered saline (PBS). The R17 C-terminal 8-His fusion construct was purified using Ni-agarose beads (Qiagen, Valencia, Calif.), followed by size exclusion chromatography (SEC) on a HiLoad 26/60 Superdex 200 column (GE Healthcare). SDS-PAGE and Western blot analysis confirmed protein purity. Two additional variants of R17 were used in this study: R17 mutant, where residues 29 to 32 of the mature sequence RKDR (BBXB) were mutated to EDDE and are referred to as R17GAG1 and residues 333 to 337 of the mature sequence KGRRK (SEQ ID NO: 7)(BXBBB) were mutated to DGEED (SEQ ID NO: 8) and are referred to as R17GAG2. Mutagenesis was performed using a multisite QuickChange mutagenesis kit (Agilent Technologies) on the background of the wild-type R17 C-terminal His construct and verified by DNA sequencing. The identity of R17 was confirmed by N-terminal sequencing (Midwest Analytical, Saint Louis, Mo.).

Bio-Plex Cytokine Arrays

Customized Bio-Plex pro arrays (Bio-Rad) were ordered to detect murine IL-6, IL-1β, IL-10, IL-12p70, IL-13, IFN-γ, CCL2, CCL3, CCL5, and TNF-α. The assay was run per the manufacturer's guidelines, with the exception that recombinant RHVP Fc fusion proteins were preincubated with the recombinant standards for 20 min prior to the addition to the assay plate. In brief, the antibody-coupled beads of the 10 analytes were prepared in assay buffer and then placed in each well of the assay plate. The recombinant standards were diluted as outlined in the manufacturer's guidelines, and the standard was then diluted 1:3 to generate a standard curve. After the standards were diluted, 150 µl of PBS, R17-Fc, or R6-Fc was added to each of the standards and incubated for 20 min at room temperature. The standards were then added to each well and incubated on a shaker at room temperature for 30 min. The plate was washed 3 times, and then detection antibody was added and incubated on a shaker for 30 min at room temperature. The plate was again washed 3 times, and then streptavidin-PE was added to each well and incubated on a shaker at room temperature for 10 min. After the plate was washed 3 times, 125 µl of assay buffer was added to each well, and the plate was read on a Bio-Plex plate reader system using Bio-Plex Manager software for analysis.

Recombinant Chemokines

Murine CCL2 and CCL3 chemokines were expressed in *Escherichia coli*, refolded from inclusion bodies, and purified as previously described (31). All chemokines except for murine CCL2 and CCL3 were purchased from Peprotech. Biotinylation of chemokines was performed using EZ-Link N-hydroxysuccinimide (NHS)-polyethylene glycol 4 (PEG4)-biotin (Thermo Scientific) using a 2:1 molar ratio of biotin to chemokines. Unbound biotin was removed using Thermo Scientific Zebra spin desalting columns per the manufacturer's instruction.

SPR Binding Analysis

Surface plasmon binding (SPR) was used to directly measure the affinity and kinetics of chemokine binding by R17 and its variants. R17, R17GAG1, and R17GAG2 were immobilized on a CM5 chip (GE Healthcare) using standard amine coupling chemistry (Biacore amine coupling kit) to a level of 200 to 500 response units (RU) for kinetic binding analysis and 1,000 RU for equilibrium binding analysis using a Biacore T-100 biosensor (GE Healthcare). A control flow cell was prepared by coupling non-chemokine binding protein R7 or NeutrAvidin to the chip at a similar level. Experiments were performed at 100 µl/min and 25° C. using HBS-EP (10 mM HEPES [pH 7.5], 150 mM NaCl, 3 mM EDTA, 0.005% Tween 20) as a running buffer. High flow rates and low levels of coupled proteins were used to minimize the effects of mass transport. For all kinetic experiments, 358 µl of chemokine was injected over experimental and control flow cells followed by a 500-s period to monitor dissociation before regeneration was achieved by injecting 100 µl of 0.1 M glycine (pH 2.0). Each experiment was performed at a minimum of three times with eight different chemokine concentrations followed by three buffer injections. The association (Ka) and the dissociation (Kd) values were determined simultaneously by globally fitting sensorgrams for an entire range of chemokine concentrations to a 1:1 mass transport model with BIAevaluation software. This global analysis was performed independently for each series of concentrations, the resulting values were averaged, and the standard deviation was calculated to reflect the experimental error. Apparent equilibrium dissociation constants were determined either from the kinetic values using the equation $K_{D,kin}=K_d/K_a$ or from saturation binding experiments, $K_{D,eq}=RU$ response/chemokine concentration.

Chemotaxis Assay

THP-1 cells were cultured in RPMI 1640 medium supplemented with 10% fetal bovine serum (FBS), 1 mM sodium pyruvate, 100 units/ml penicillin, 100 µg/ml streptomycin, and 2 mM l-glutamine. Cell culture was maintained between $2\times10^5$ and $9\times10^5$ cells/ml at 37° C. with 5% CO2. PBMCs were isolated from heparinized blood by Ficoll gradient centrifugation (GE Biosciences) and resuspended in RPMI 1640 medium supplemented with 1% bovine serum albumin (BSA). Ninety-six-well Transwell permeable support inserts (Corning Costar; Sigma-Aldrich) were used. Human CCL2 and CCL3 at concentrations of 10 nM were diluted in 1% BSA RPMI and placed in the lower compartment, and $6\times10^4$ of either human THP-1 monocytes or $1\times10^5$ human PBMCs were placed in the upper chamber, separated by a 5-µm-pore-size filter. After PBMCs were incubated for 3 h and the THP-1 cells for 4 h at 37° C., the cells in the lower chamber were spun, lysed, and counted using CyQuant dye (Life Technologies). For competition experiments, three proteins, R17, M3, and R7, were added to the lower chamber to a final concentration of 100 nM. The bacterially refolded purified M3 was used as a positive control for inhibition, while R7 was used as a negative control for inhibition.

Calcium Mobilization Assays

THP-1 cells were incubated at a density of $5\times10^6$ cells/ml in $Ca^{2+}$ buffer with 1 µM Fura-2AM loading dye and 0.02% pluronic at 37° C. for 30 min in the dark before being washed twice and resuspended at $5\times10^6$ cells/ml in $Ca^{2+}$-free buffer. Fura-2-loaded cells were transferred into a poly-1-lysine-treated 96-well assay plate at $5\times10^5$ cells/well for CCL2 stimulation. A total of 160 nM CCL2 was preincubated with buffer control, 2 µM R17, 2 µM MR1 (32), or 1 µM M3 for 5 min at 37° C. prior to cell stimulation. Ca2+ response was measured on a FlexStation system from Molecular Devices based on the spectrofluorimetry at 37° C.

Competition of Chemokine Binding to Cells

To evaluate CCL2, CCL3, and CCL5 binding to CHOK1 and CHO745 cells, chemokines and a negative-control protein (MR1) (32) were nonspecifically biotinylated using the EZ-biotin kit (Pierce) using a 2:1 biotin-to-protein molar ratio, followed by removal of unbound biotin (Thermo Scientific Zebra desalting columns). CHOK1 and CHO745 cells were maintained in F-12 medium supplemented with 10% fetal calf serum (FCS) and 100× Penn-Strep. On the day of the experiment, cells were washed once with PBS, detached using 0.2% EDTA, and resuspended in staining buffer containing PBS, 0.5% BSA, and 2 mM EDTA. Biotinylated chemokines were added to cells to a final concentration ranging from 50 to 250 nM, incubated for an hour on ice, washed twice, and detected with streptavidin PE (Life Technologies) using flow cytometry. To determine the effect of R17, R17GAG1, and R17GAG2 on CCL2-, CCL3-, and CCL5-GAG interaction, 0.1 to 0.5 µM of R17 or R17GAG1 or R17GAG2 was precomplexed with biotinylated chemokines and incubated with both CHOK1 and CHO745 cells. As a positive control for inhibition, bacterially refolded M3 was used. Flow cytometry was undertaken using a FACS array or FACSCalibur, and data were analyzed using FlowJo software.

R17 Binding to Cells

R17, R17GAG1, and R17GAG2 were nonspecifically biotinylated using the EZ-biotin kit (Pierce) using a 2:1 biotin-to-protein molar ratio, followed by removal of unbound biotin (Thermo Scientific Zebra desalting columns), and added to CHOK1 and CHO745 to a final concentration of 0.2 µM in the same manner as described in the section above.

Example 1: R17 Binds CC and C Chemokines with High Affinity

To assess the ability of R17 to directly interact with chemokines, a large panel of different chemokines and cytokines using surface plasmon resonance (SPR) were screened (FIG. 2A-FIG. 2E). In these experiments, R17 was covalently coupled to a BIAcore CM5 chip and examined for specific ligand binding. C-terminal Fc or His was not used for immobilization, because highly charged chemokines nonspecifically interact with antibodies necessary to capture proteins either by Fc or His tag. Of the 25 mouse and human chemokines tested, a concentration-dependent increase in the refractive index together with saturable binding was observed for mCCL2 and hCCL2, for mCCL3 and hCCL3, for mCCL4, mCCL5 and hCCL5, and for mCCL8, mCL11, mCCL20, mCCL24, mCCL19, mCCL12, and mXCL1. As negative controls for chemokine binding, either a NeutrAvidin-coupled chip or RHVP R7 were used; both of these proteins lack chemokine binding activity. From the SPR experiments, it was determined that R17 directly interacts with all of the CC chemokines tested except mCCL21, a chemokine expressed constitutively in secondary lymphoid tissues and thought to be essential for cell migration into lymphoid organs. It was also determined that R17 binds the C chemokine lymphotactin (XCL1). In contrast, R17 did not interact with any of the CXC chemokines examined (mCXCL8, mCXCL10, mCXCL9, mCXCL2, mCXCL12, mCXCL1) or the CX3C chemokine fractalkine. SPR binding studies with other murine cytokines (IL-13, IL-12, IL-6, IL-17, TNF-α) did not reveal any additional R17 ligand binding specificities. Among the chemokines that R17 binds, the apparent complex half-lives (t½) vary considerably. For example, mouse and human versions of CCL2, CCL9, CCL12, and CCL20 all form complexes with measurable off rates (t½ varying from 2 to 32 s), and reported in FIG. 2E equilibrium and kinetic binding parameters which generally are in agreement. In contrast, CCL3, CCL4, CCL5, and XCL1 form stable complexes with extremely slow dissociation rates that appear to be in excess of 10 min (FIG. 2A-E). Quantitative kinetic characterization of the latter chemokines could not be measured accurately due to mass transport limitations during the association phase and lack of an appropriate competitor to speed up the dissociation phase. We therefore report apparent $K_{D,eq}$ values determined from saturation binding analysis for these chemokines (0.1 to 4 nM), although the actual affinities may well be picomolar.

Example 2: R17 Blocks Chemokine-Mediated Cell Migration

Figure 3A:
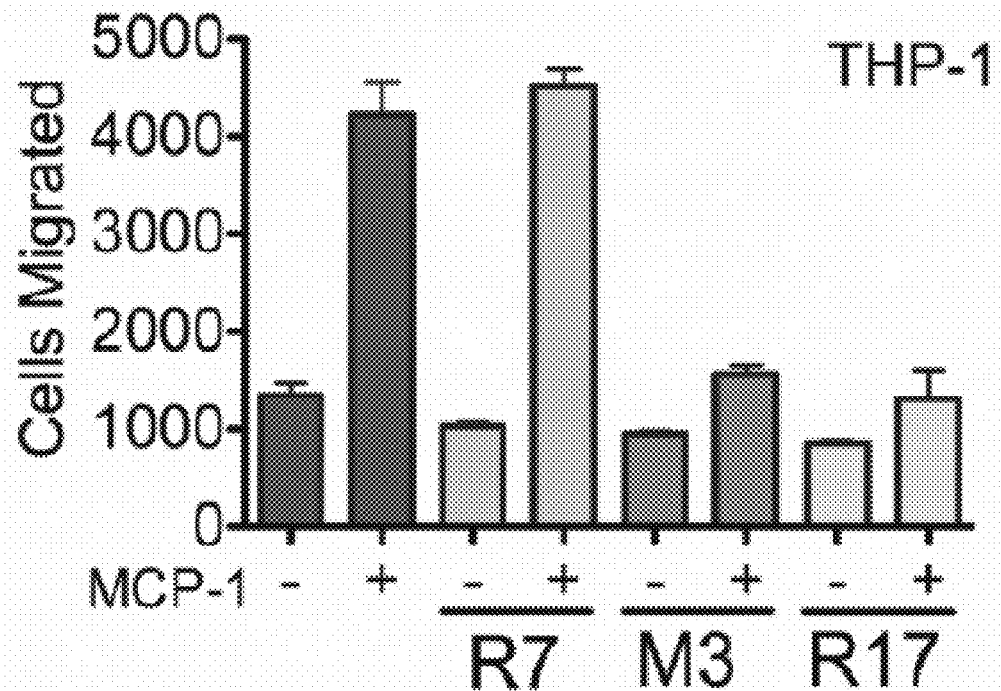
FIG. 3 A.
FIG. 3B and FIG. 3C show R17 blocks CC-chemokine mediated transmigration and receptor signaling. Transmigration of either Thp-1 cells stimulated with hCCL2 (FIG. 3A) or human PBMCs (FIG. 3B) stimulated with CCL3, M3 (positive control) and R7 (negative) control. Different complexes were formed by incubating 10 nM of hCCL2 with 100 nM of R7, M3 or R17 at room temperature for 30 min and added to the bottom of transmigration plate. $6 \times 10^4$ of Thp-1 cells or $1 \times 10^5$ of PBMCs were added to the top of trans-well inserts. The transmigration plates were incubated at 37° C. for 4 hours for Thp-1 chemotaxis and 3 hours for PBMC chemotaxis. The cells that migrated from the trans-well insert to the bottom of transmigration plates were pelleted and counted using CyQuant dye. Standard deviations represent an average of at least three independent experiments. **P<0.005.
Figure 3B:
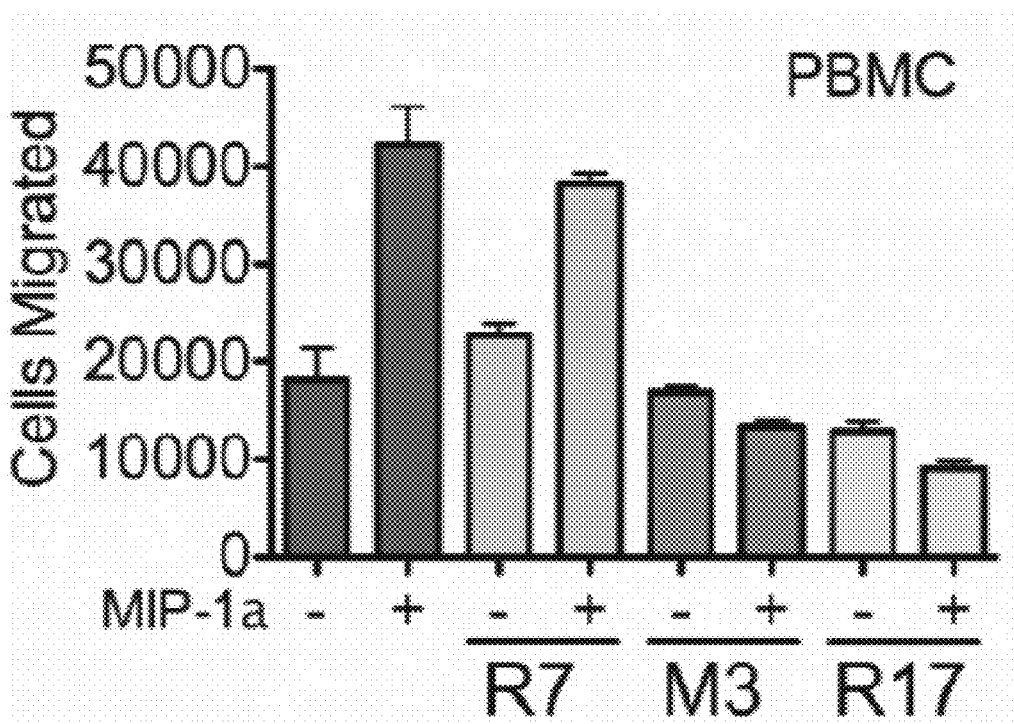

To address the functional consequences of R17-chemokine interactions, we performed experiments evaluating the migration of the human monocytic cell line THP-1 in response to hCCL2, a fast dissociating R17 ligand ($K_{D,eq}$=12 nM, t½=2.1 s), and human PBMCs in response to hCCL3, a slow off-rate R17 ligand ($K_{D,eq}$=1.4 nM, t½, app>1,000 s). We found that R17 potently blocked THP-1 cell transmigration when incubated in 10-fold molar excess of CCL2 (FIG. 3A). Similar disruption was observed when we incubated CCL2 with the M3 decoy receptor encoded by MHV68, which was previously shown to effectively block cell migration mediated by CCL19 and CCL21. As a negative control, we used RHVP R7 that lacks chemokine binding activity. Similar results were obtained when we examined the ability of R17 to disrupt CCL3-mediated transmigration of human PBMCs, where R17 and M3 proved inhibitory while R7 did not (FIG. 3B).

Example 3: R17 Blocks Chemokine-Mediated Calcium Release

Figure 3C:
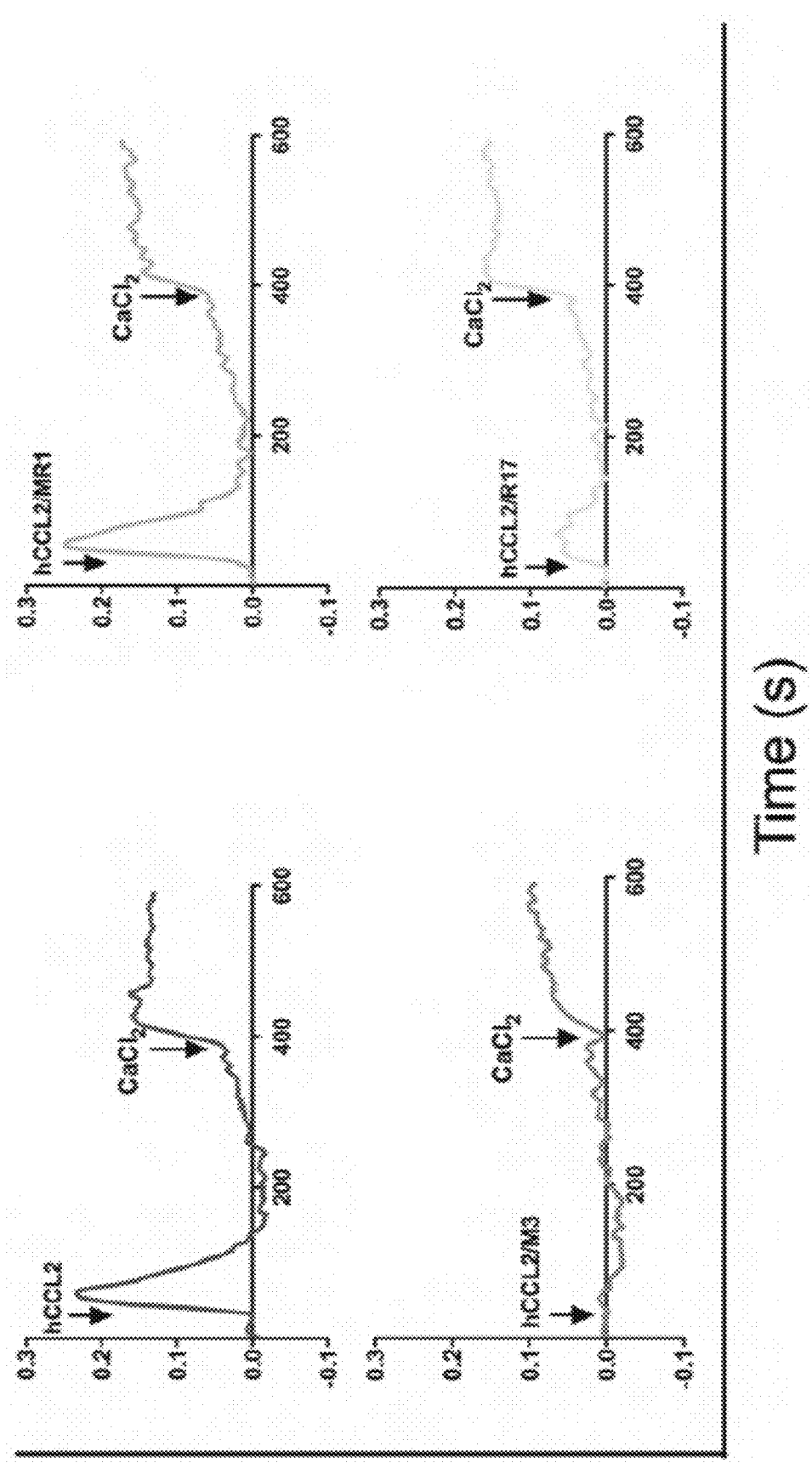
Figure 4A:
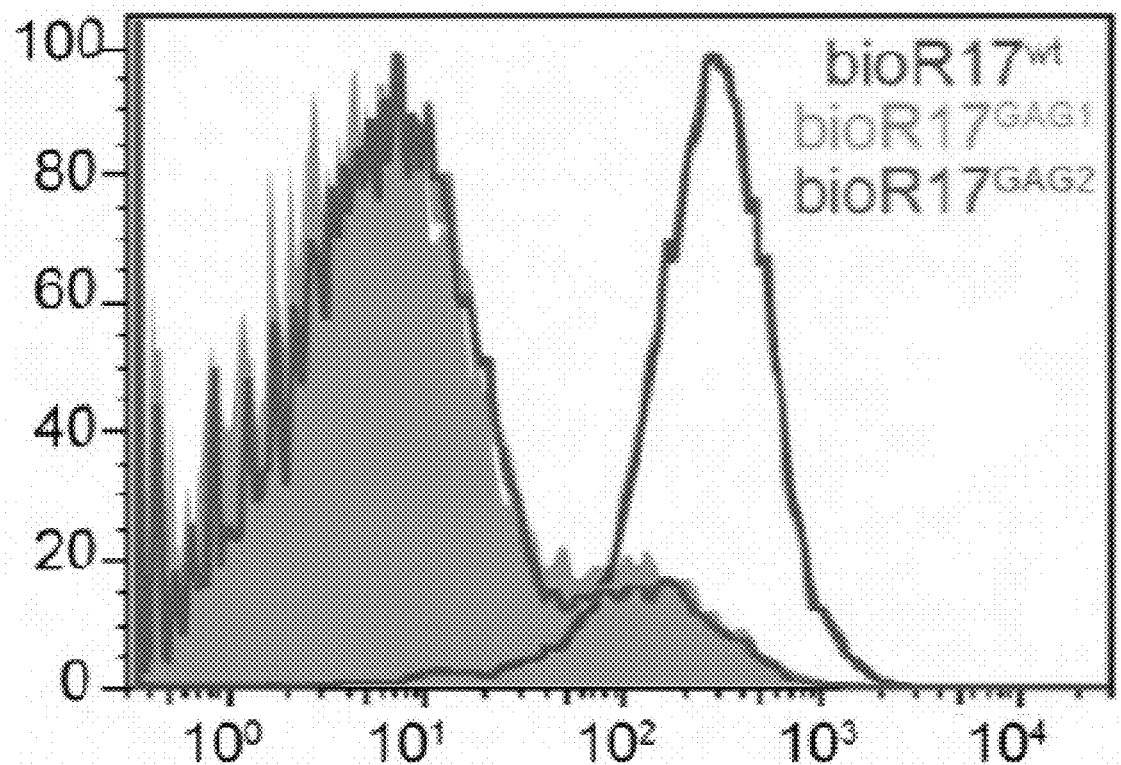
Figure 4B:
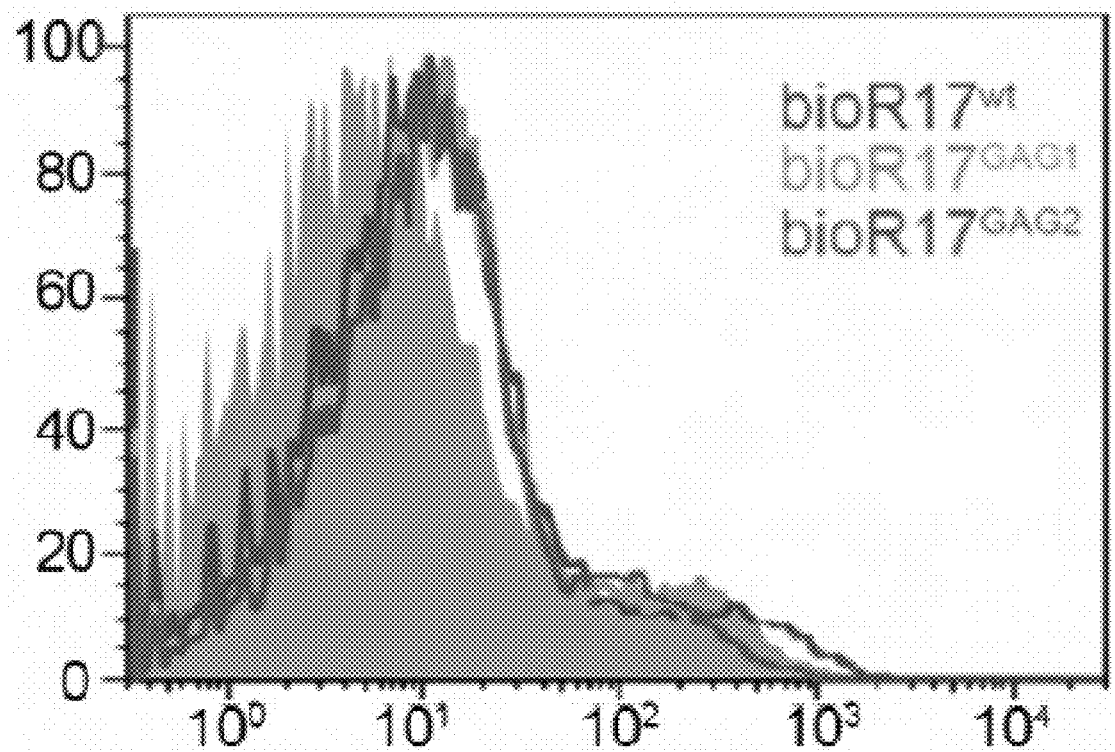

Activation of chemokine receptor signaling leads to calcium release from endoplasmic reticulum stores resulting in elevated levels of cytoplasmic calcium. Changes in calcium levels upon chemokine stimulation can be monitored in real time by Fura-2 dye-loaded cells. Previous experiments with MHV68 M3 revealed that it is an effective Ca2+ flux inhibitor for several distinct chemokines that it engages. We have tested the ability of R17 to inhibit transient increase in intracellular calcium induced by hCCL2 in THP-1 cells. When added in 10-fold molar excess, R17 effectively diminishes CCL2-mediated calcium flux, albeit not as effectively as M3, which forms significantly more stable complexes with CCL2 (FIG. 3C). The addition of a negative-control protein, MR-1, showed no changes in CCL2-mediated calcium mobilization. Together with the transmigration assays, these data suggest that R17 might function as an inhibitor of CC chemokine signaling.

Figure 5B:
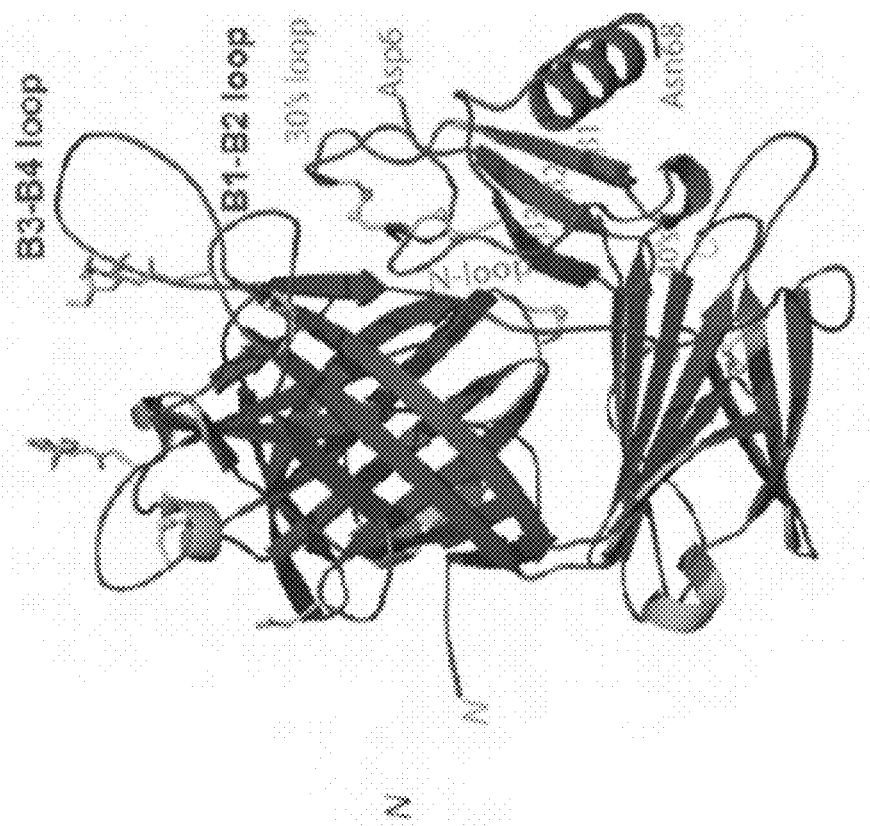
FIG. 5A, FIG. 5B, FIG. 5C and FIG. 5D show Crystal structure of RHVP R17 alone and in complex with murine CCL3.
Figure 5A:
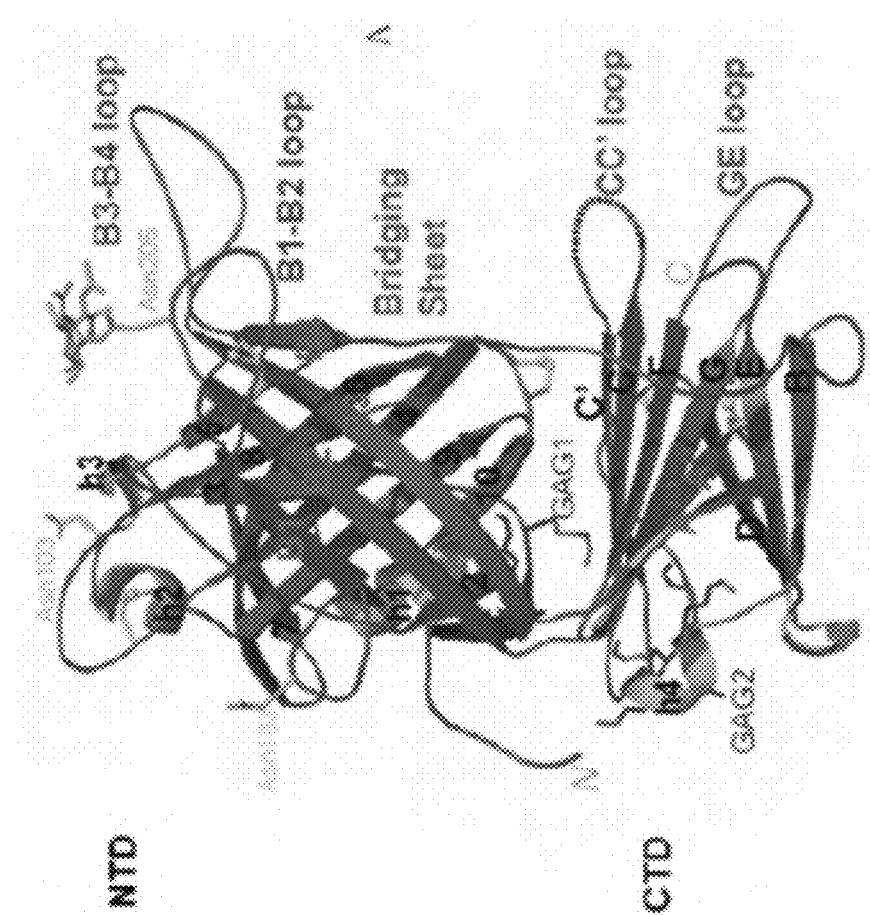
Figures 5C, 5D:
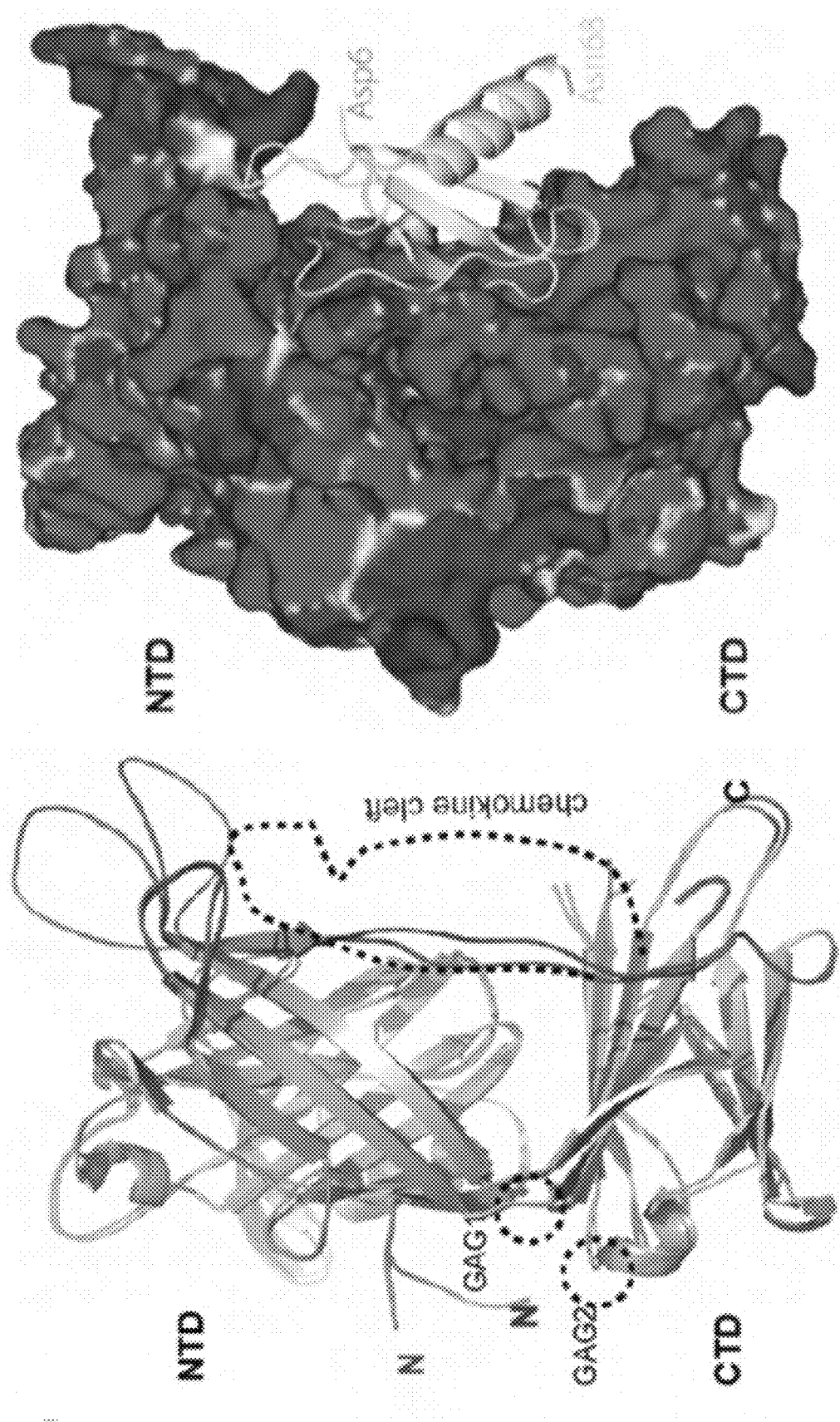

Example 4: R17 Interacts with GAGs Via Determinants Distinct from Chemokine Binding Our flow cytometry experiments suggest that R17 can simultaneously engage cell surface GAGs and chemokines. Examination of the amino acid sequence of R17 reveals the presence of two BBXB motifs known to be important for GAG binding in a number of different proteins. We therefore created two variants of R17 through site-directed mutagenesis, R17GAG1, in which residues 29 to 32 RKDR (BBXB) were mutated to EDDE, and R17GAG2, where residues 333 to 337 KGRRK (SEQ ID NO: 7)(BXBBB) were mutated to DGEED (SEQ ID NO: 8). When tested, neither biotinylated R17 variant was capable of staining CHOK1 cells, suggesting that both BBXB motifs are indeed critical for GAG binding (FIG. 5A). However, both R17GAG1 and R17GAG2 bound CCL2 and CCL3 with binding parameters comparable to those observed for wild-type R17 (FIG. 5B). Thus, the R17 determinants for cell surface GAG binding are distinct from those mediating the high-affinity binding of CC chemokines.

Discussion for Examples 1-4

The identification and characterization of a novel soluble chemokine binding protein, R17, encoded by RHVP is described. The mature secreted R17 protein is composed of 412 residues with six potential disulfide bridges and three Asn-linked glycosylation sites. R17 displays no appreciable amino acid sequence similarity to any other viral or cellular protein. In contrast to the highly promiscuous chemokine binding of MHV68 M3, R17 binds selectively to CC chemokines and XCL1. Our SPR studies indicate that R17 binds CCL2, CCL8, CCL9, and CCL20 with affinities ranging from 1 to 80 nM, rapid association kinetics, and half-lives of 2 to 35 s. R17 engages another group of chemokines (CCL3, CCL4, CCL5, CCL24, and XCL1) with extremely long half-lives that are difficult to quantitate but we estimate as greater than 10 min. As such, the chemokine binding properties of R17 closely resemble those of the vCCI decoy receptor encoded by ectromelia, EVM1, which forms moderately fast dissociating complexes with CCL2 and highly kinetically stable complexes with CCL3 and CCL5 (20). The difference in the off rates among two groups of R17-chemokine complexes is interesting and is likely to reflect variation in specific amino acids important for this interaction. For example, structural inspection of CCL2, CCL3, and CCL5 chemokines together with mutagenesis data indicate distinct positioning of basic residues thought to mediate GAG binding. While CCL3 and CCL5 have BBXB motifs localized to the 40's loop (loop connecting beta strands 2 and 3), GAG binding residues on CCL2 have been mapped to R18, K19, and R24 of the N-terminal loop (20's loop).

Similarly to MHV68 M3 and poxvirus vCCIs, RHVP R17 appears to operate as a true decoy receptor, blocking the ability of chemokines to activate their host receptors. The data indicates that R17 capably inhibits both CCL2- and CCL3-driven transmigration despite the fact that CCL3 is a much tighter binder. But our comparison of the abilities of R17 and M3 to block CCL2-mediated calcium release indicates a greater potency for M3, which binds this chemokine with a significantly longer half-life than R17.

Sabotage of chemokine function by R17 and M3. Schematic diagram illustrating R17- and M3-mediated disruption of chemokine binding to GPCRs, M3-mediated disruption of chemokine-GAG interactions, and R17 association with cell surface GAGs.

In addition to chemokine binding, R17 also tightly associates with cell surface GAGs. Indeed, our flow cytometry experiments indicate that R17 can dramatically increase the association of chemokines with cell surfaces. We inspected the primary sequence of R17, finding two basic BBXB motifs that are commonly found in GAG binding proteins, including many chemokines. R17 variants lacking either BBXB motif do not bind cell surface GAGs, and chemokine binding experiments with these variants indicate that the R17 chemokine and GAG binding sites are independently positioned. As such, the increased chemokine cell surface association we observed can be explained by the high-affinity binding of chemokines to GAG-associated R17. In this regard, R17 exhibits similarity with myxoma virus MT-1 (vCCI) that has been shown to interact with cell surface GAGs while simultaneously blocking receptor-mediated chemokine signaling (45). In contrast, ectromelia E163 binds both chemokines and GAGs, although unlike R17 and MT-1, disruption of chemokine signaling by this protein has not been observed.

The idea of using virally encoded decoy receptors to therapeutically block chemokine signaling was introduced a few years ago (46). For example, vCCI has been shown to diminish inflammation in allergen-induced asthma (47) and intraperitoneal injection mouse models. MT-1 treatment was shown to alleviate vascular pathology by inhibiting early monocyte and lymphocyte infiltration in vascular transplantation models. M3 has shown promise as an anti-inflammatory therapeutic in several models, including tumor rejection and vascular injury. Islet-specific M3 expression can also prevent inflammatory recruitment, islet destruction, and subsequent diabetes in mouse insulitis models. The discovery of R17 as a novel chemokine decoy receptor with unique chemokine and GAG binding properties sets the stage for future experiments evaluating its therapeutic potential in similar experimental models Example 5: Structure Determination of RHVP R17

To enable structural studies, recombinant R17 protein was purified from 293F cells cultured with kifunensine, an inhibitor of class I α-mannosidase (Elbein et al., 1991). Before crystallization, R17 was treated with Endoglycosidase H (EndoH) to trim carbohydrate. The structure of unligated R17 was determined by iodide single-wavelength anomalous dispersion (SAD) with sites located by SHELXD (Sheldrick, 2008), phases estimated using MLPHARE (Dodson et al., 1997), and density modification using PARROT (Cowtan, 2010). The initial model of R17 was built using ARP/wARP (Murshudov et al., 1997), and the final model was produced after numerous rounds of manual building using Coot (Emsley and Cowtan, 2004) and refinement in Phenix (Adams et al., 2011). The model spans residues 14-400 of the mature protein, with GlcNAc linkages to Asn103 and Asn205 along with 355 water molecules (FIG. 1A).

R17 adopts a two-lobed structure with an N-terminal domain (NTD) positioned perpendicular to a C-terminal domain (CTD) linked together by a bridging sheet (BS). The terminal domains consist of β-sandwich folds decorated by loops and helical segments, while the BS is composed of four strands packed with the NTD (residues 190-216 and 233-266) and two strands inserted into the CTD (residues 218-232) (FIG. 1A). The NTD spans residues 14-187 and is composed of a seven- and three-stranded sheet (FIG. 1A). Three disulfide bonds occur in the NTD; one pins the end of helix h1 to the end of strand s10, one bridges the turn at the start of s4, and another links the end of s4 to the start of s9. The CTD spans residues 285-400 and adopts an approximately I-type immunoglobulin fold composed of nine β strands and a disulfide linking the C' strand with the beginning of the D strand. A long flexible linker connects the BS and CTD, specifically residues 265-288, of which residues 267-270 are refined with high B factors. One disulfide is found within the BS B1-B2 loop while another joins the end of the flexible BS linker to the A" strand inserted into the CTD.

Example 6: Crystal Structure of the R17-CCL3 Complex

Figure 1B:
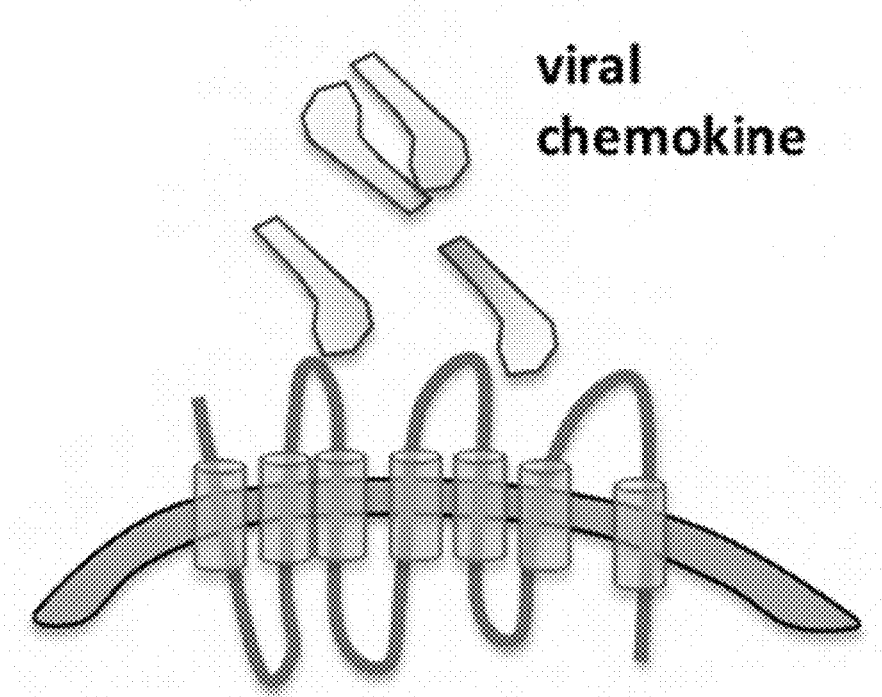

To address where chemokines bind R17 we initiated co-crystallization experiments with CCL3, a chemokine we previously had shown binds the decoy receptor with an exceptionally long kinetic half-life leading to the potent inhibition of PBMC transmigration (Lubman et al., 2014). Diffraction quality crystals were obtained using a CCL3 mutant (D26A) reported to reduce aggregation (Czaplewski et al., 1999) and an R17GAG2 variant that could no longer interact with cell surfaces due to the mutation of residues 333KGRRK337 (SEQ ID NO: 7) to 333DGEED337 (SEQ ID NO: 8). The structure of the complex was solved by molecular replacement with a final atomic model refined to 3.0 Å resolution (Table 1 and FIG. 1B). Each asymmetric unit contained two R17GAG2-CCL3 complexes, with two GlcNAc linkages to Asn103 and Asn205 of R17 in chain A and a single GlcNAc linkage to Asn205 built for chain B. Using multi-angle static light scattering we determined that R17 binds CCL3 with 1:1 stoichiometry, suggesting that additional lattice interactions observed in the crystal structure are not functionally relevant.

Figure 1C:
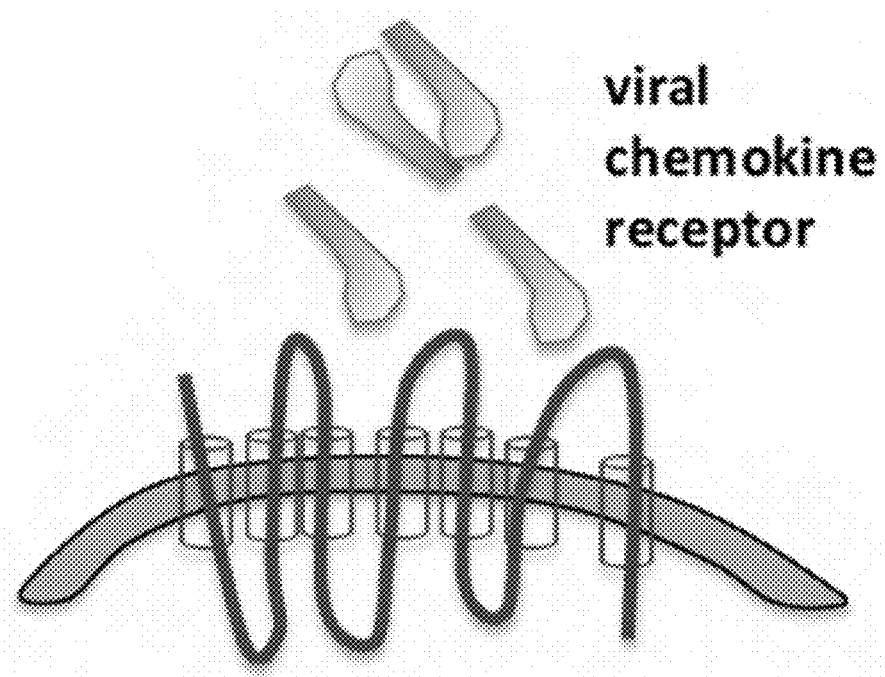

The primary structural element used by R17 to create a chemokine binding platform is the flexible linker that connects the BS of R17 with the CTD and forms a hydrophobic cavity between the two β sandwiches. While this region is not well ordered in the crystal structure of the unligated R17, it becomes partially ordered upon ligand binding (FIG. 1C). There are 31 residues from CCL3 and 46 residues from R17 at the R17-CCL3 interface, leading to 2,700 Å2 of buried solvent-accessible surface area (1,385 Å2 buried for CCL3 and 1,298 Å2 buried for R17). The shape complementarity at the R17-CCL3 interface is calculated to be Sc=0.70 (Lawrence and Colman, 1993). In addition to the linker that connects the two domains, CCL3 is "clamped" through multiple interactions with both the BS and CTD. A primary structural element of the BS used to bind chemokines is the B1-B2 loop. A notable hydrophobic pocket is formed by R17 residues Val195, Leu198, Leu239, and Leu264, which serves to sequester CCL3 Phe13, a critical residue for GPCR binding (Laurence et al., 2000). The hydrogen bonds observed between the main chain carbonyl oxygens of Glu199 and Thr200 in R17 with Ser35 of CCL3 serve as yet another anchor to the BS of R17. Another pocket buries Arg45 and Asn46 of the CCL3 40 s-loop BBXB motif, formed mainly by R17 residues Tyr272, Tyr275, Trp313, Phe378, and Tyr395. Within this acidic pocket a prominent salt bridge is formed between Glu393 of R17 and Arg45 of CCL3. Arg45 is the first B (basic residue) of the BBXB GAG binding motif on CCL3, and was shown to be critical for the ability of CCL3 to bind heparin sulfate and the CCR5 receptor (Kim et al., 2001, Koopmann et al., 1999, Teng et al., 2008).

Comparison of apo with chemokine bound R17 points to several conformational variations associated with ligand binding (FIG. 1C). Significant conformational differences are observed in the linker region connecting the BS and CTD that makes numerous chemokine contacts. Large conformational differences are also observed in the B1-B2 loop, B3-B4 loop, and CC' loop of the CTD, each of which flank the engaged chemokine (FIG. 1C). The fact that R17 uses structurally labile elements to engage chemokines suggests that structural plasticity may be associated with its broad ligand binding specificity.

Example 7: R17 Binds Chemokines and Cell-Surface GAGs at Two Distinct Sites

Figure 1D:
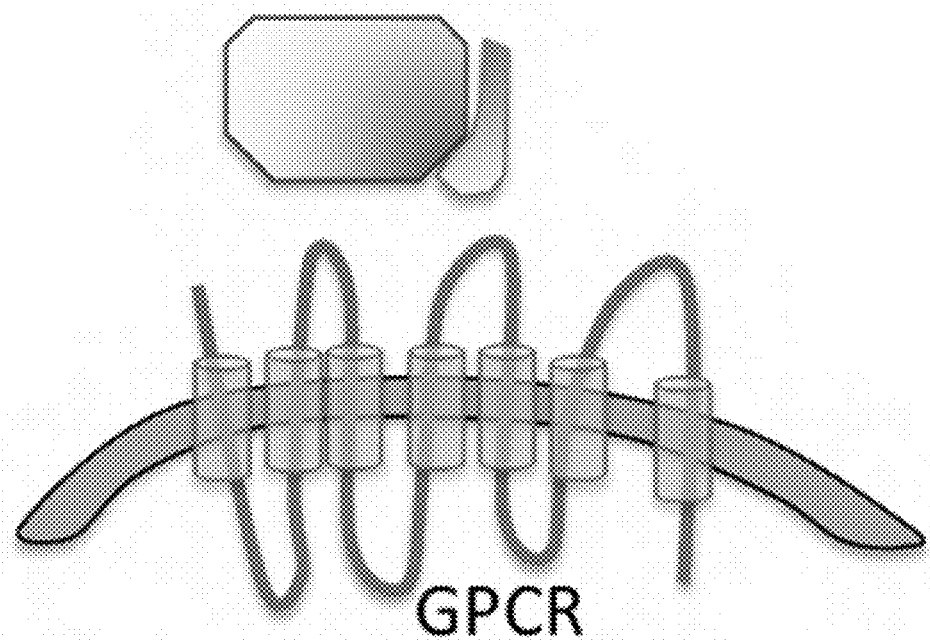
Figure 2A:
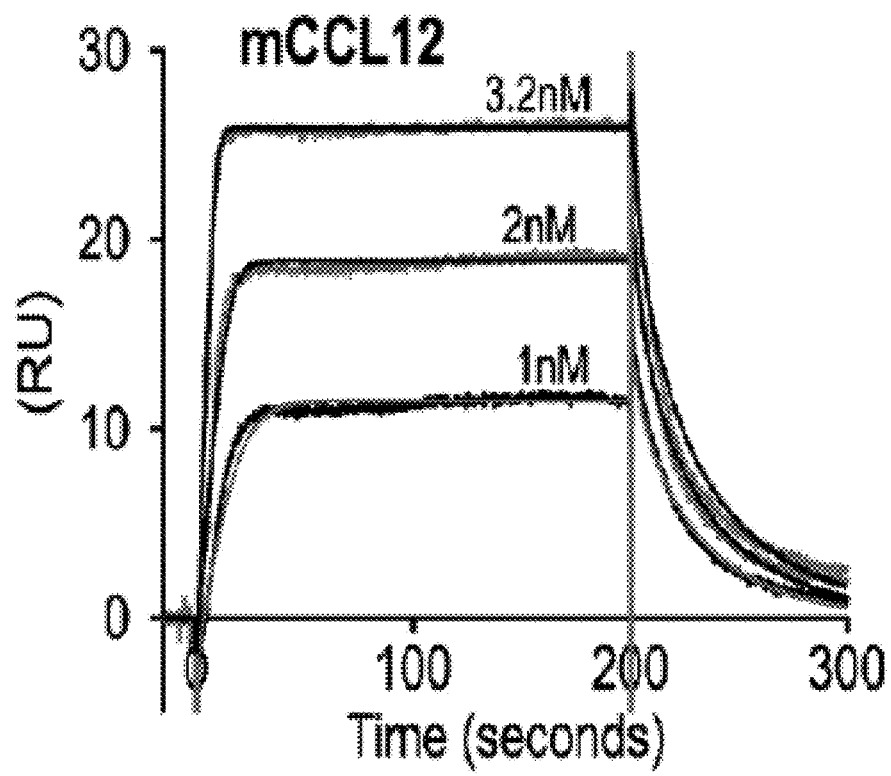
Figure 2B:
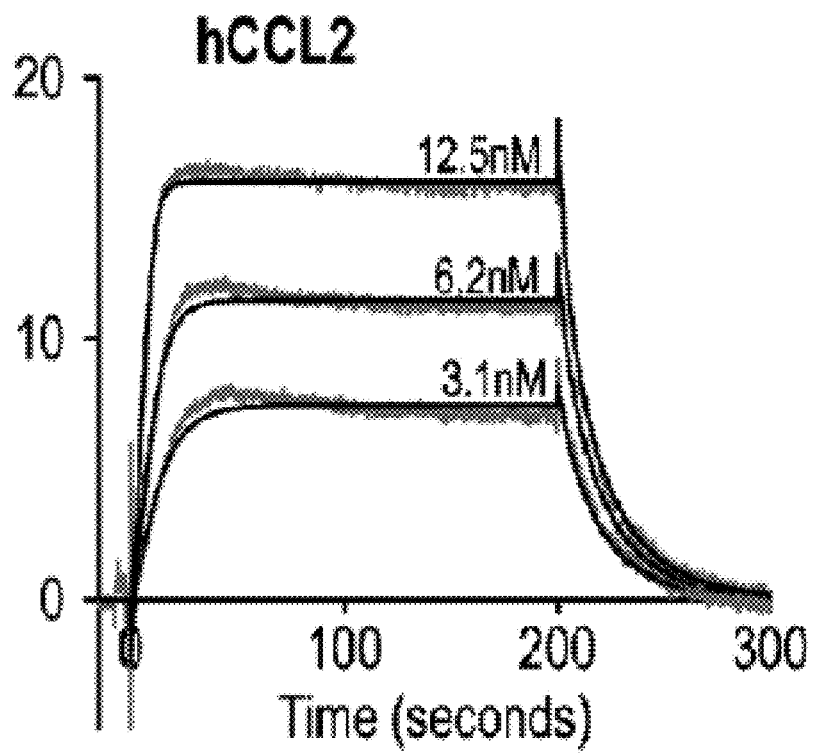
Figure 2C:
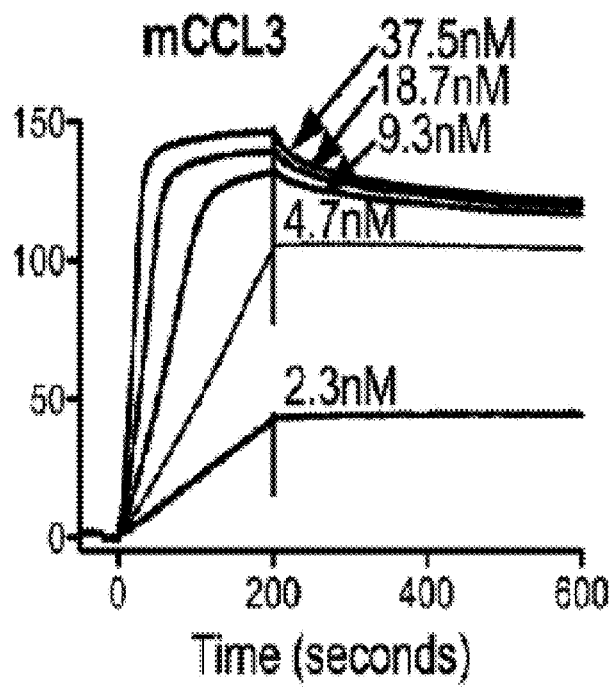
Figure 2D:
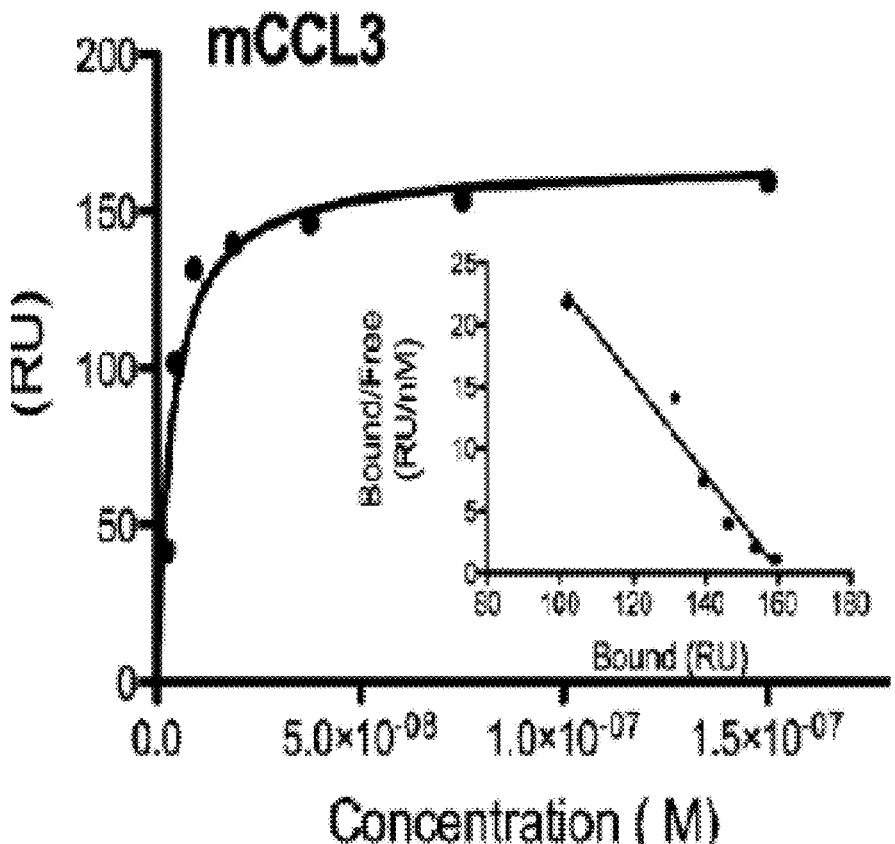

We previously reported that R17 contains two BBXB motifs located at distal ends of its linear sequence that allow it to interact with cell surfaces (Lubman et al., 2014). We hypothesized that cell-surface binding will permit R17 to sequester chemokines locally, perhaps at the site of infection. Charge reversal of either one of these motifs abrogated the ability of R17 to bind to the surface of Chinese hamster ovary (CHO) cells but did not compromise its ability to interact with chemokines (Lubman et al., 2014). The crystal structure of R17 supports our initial observations and provides insight as to how GAG binding by R17 is accomplished. Despite being far apart in the linear sequence, the two BBXB motifs found on R17 are in physical proximity to one another, coming together to create a large positively charged surface patch at the junction of the NTD and CTD (FIG. 1C). These GAG binding determinants are located more than 40 Å away from the chemokine binding site on the opposite face of R17 (FIG. 1D). Interestingly, no basic clusters are located on the surface of M3 (FIG. 2B). Mechanistically, these findings are in agreement that R17, but not M3, can bind cell surfaces while simultaneously interacting with chemokines (Lubman et al., 2014).

Figure 6A:
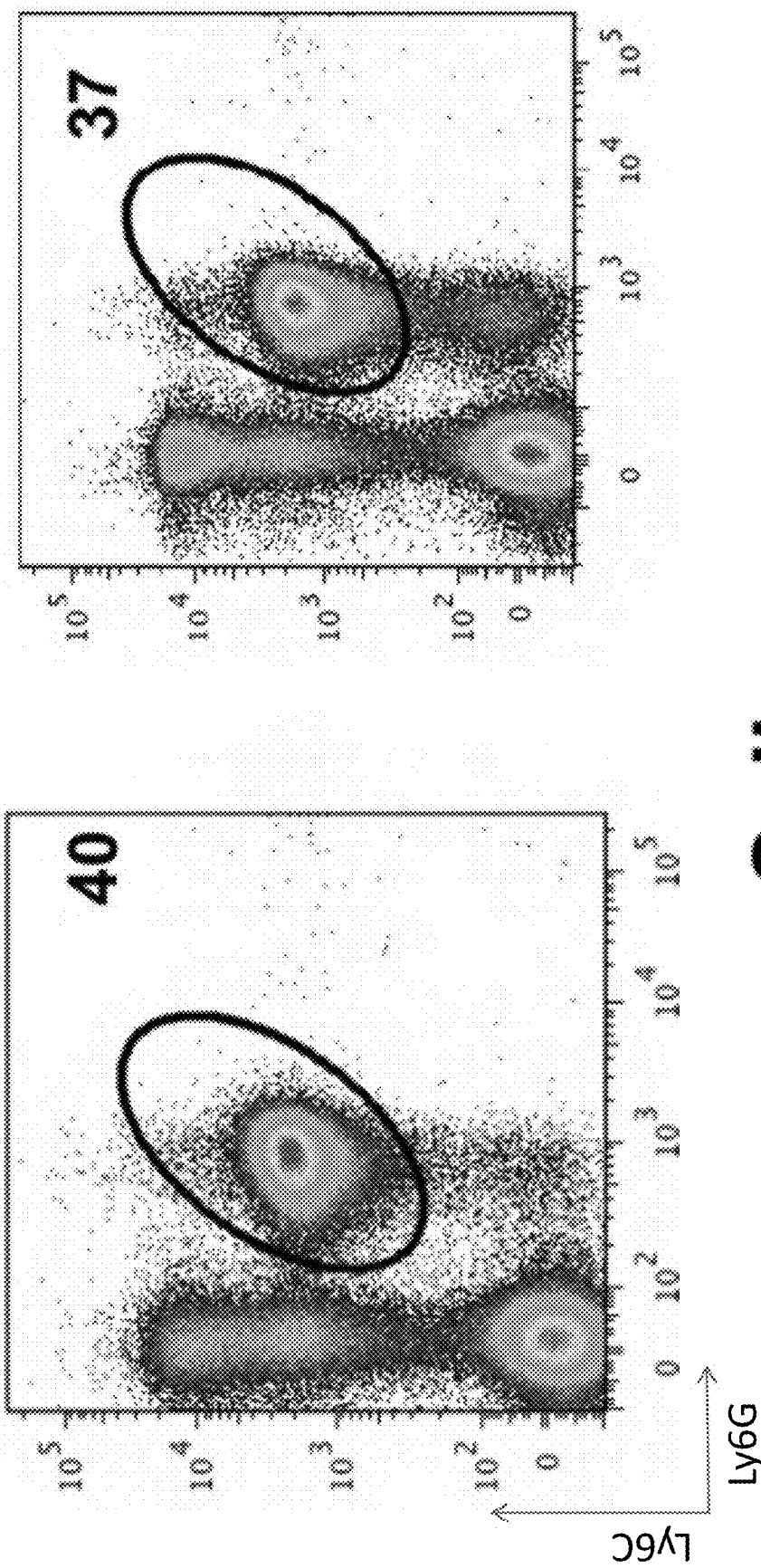
FIG. 6A, FIG. 6B, and FIG. 6C show infusion of R17 into donor mouse lungs sharply inhibits IRI-mediated intrapulmonary neutrophil accumulation following transplantation. Flow cytometry of cells taken from Brancheolar lavages 90 min post reperfusion following eight independent transplants. Ly6C is a marker for circulating monocytes. Ly6G is a marker for granulocytes and neutrophils. R17-GAG mutants has a mutation in the GAG binding and can no longer bind epithelium. R17His is a wild type protein.
Figure 6B:
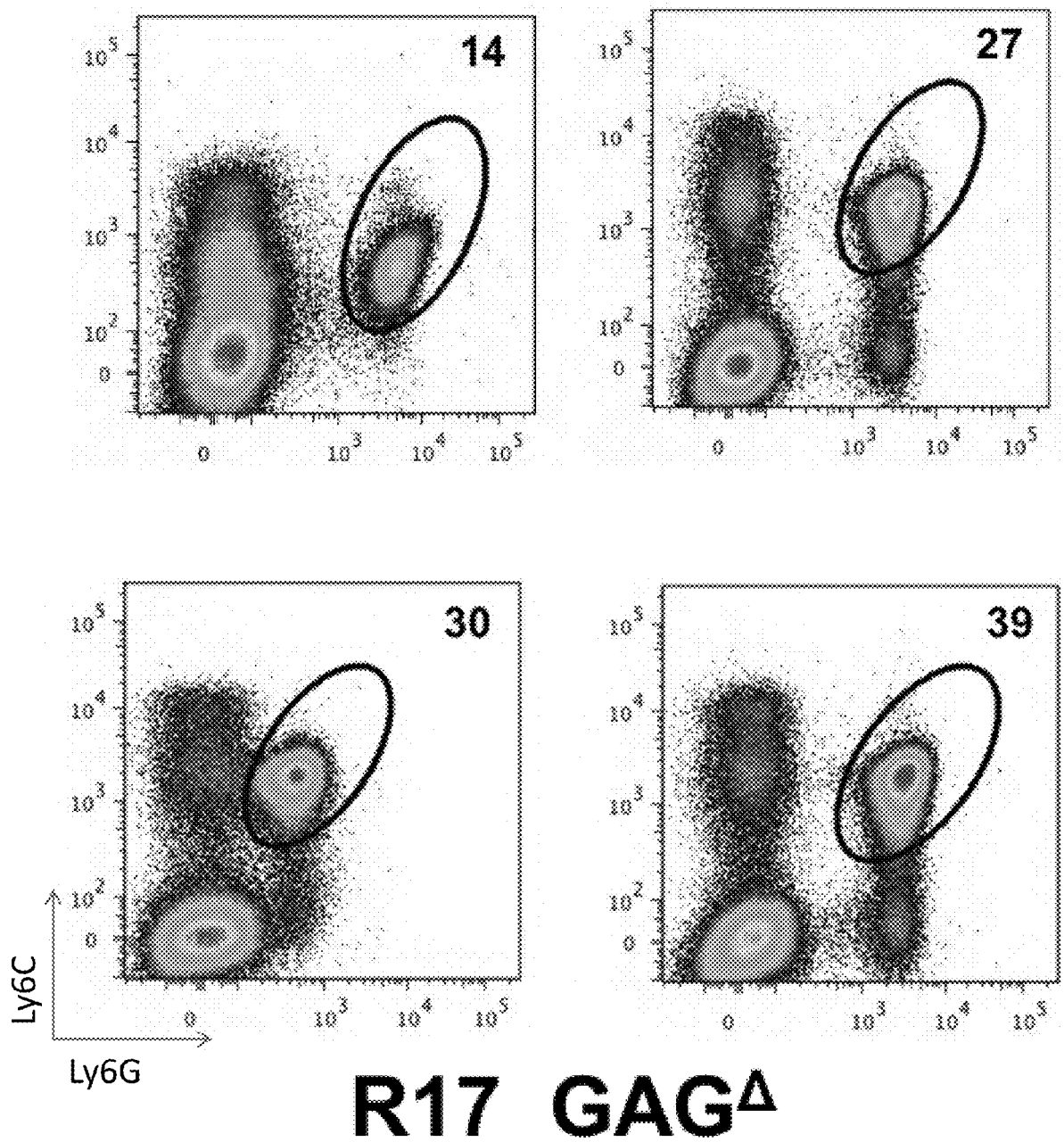
Figure 6C:
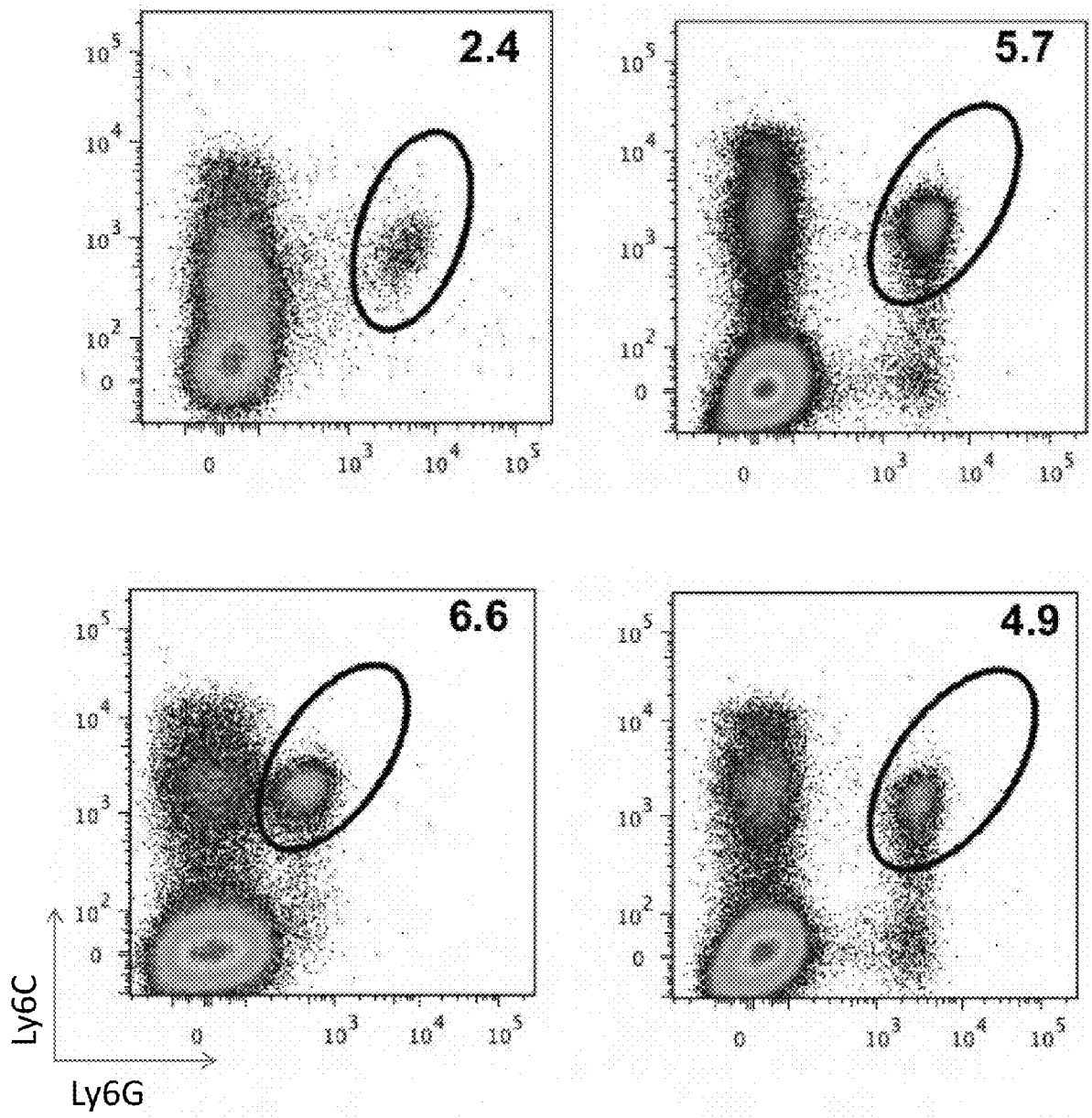
Figure 7:
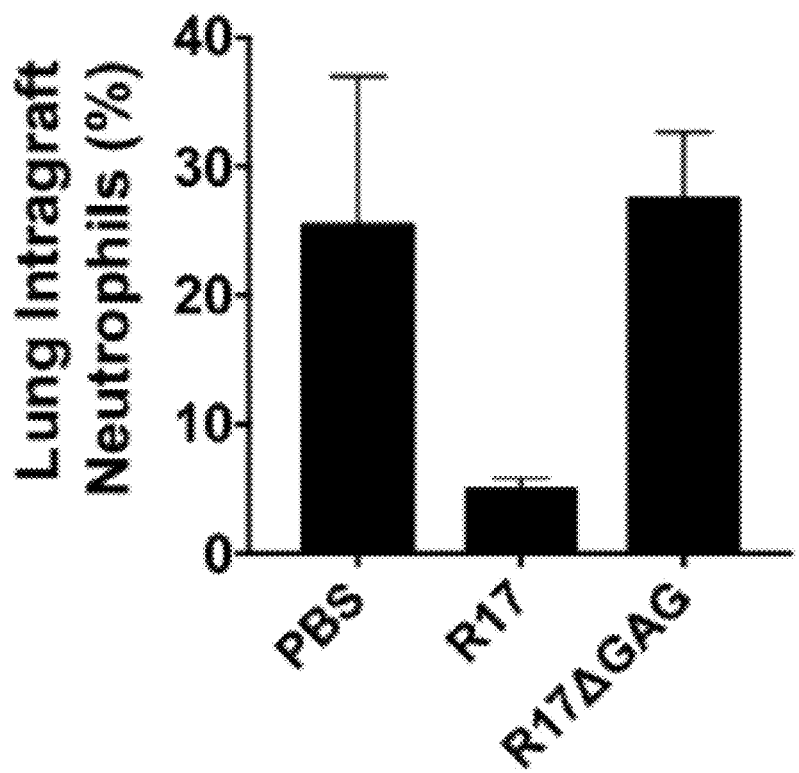
FIG. 7 shows a graphical representation of the percent lung intragraft neutrophils with PBS, R17 and R17ΔGAG.
Figure 8A:
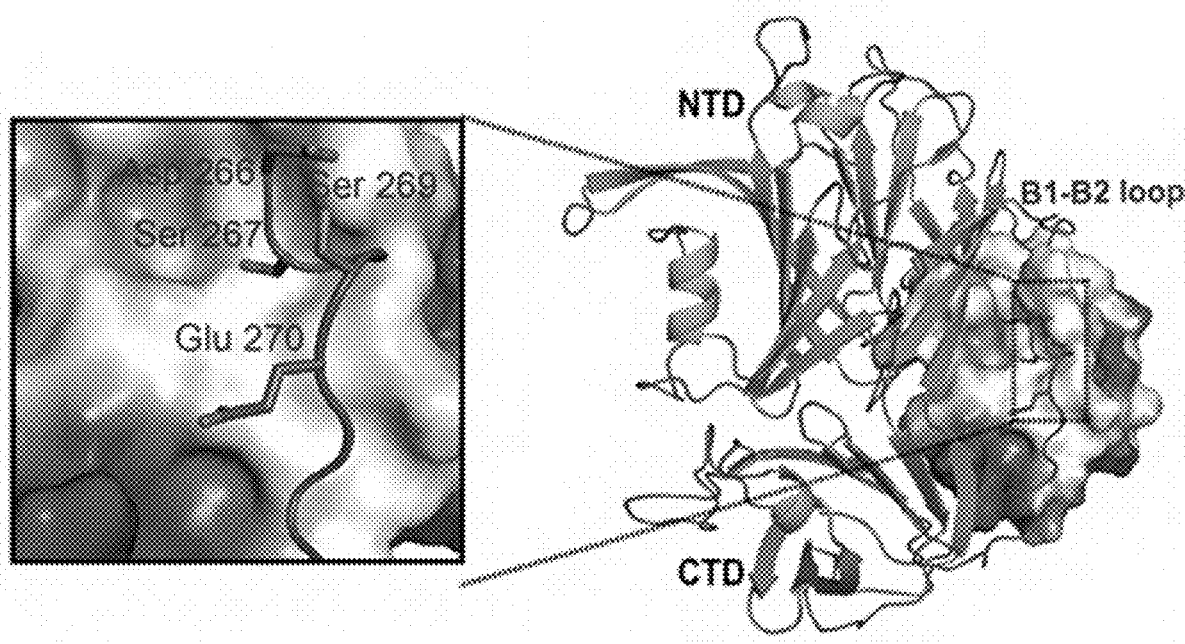
FIG. 8A, FIG. 8B, FIG. 8C, FIG. 8D, and FIG. 8E show structure based modifications of chemokine binding site. $R17^{266}DSGSE^{270}$ (aa 266 to 270 of SEQ ID NO:1) were mutated to $^{266}NAGAQ^{270}$ (SEQ ID NO: 4). Shown in (FIG. 8A) is the linker region being mutated and (FIG. 8B, FIG. 8C, FIG. 8D and FIG. 8E) SPR analysis of mCCL2 and mCCL3 binding to the R17 266NAGAQ270 (SEQ ID NO: 1) showing how this mutation abrogates binding of R17 to CCL2 and substantially decreases the half-life of R17-mCCL3 interactions.
Figure 8B:
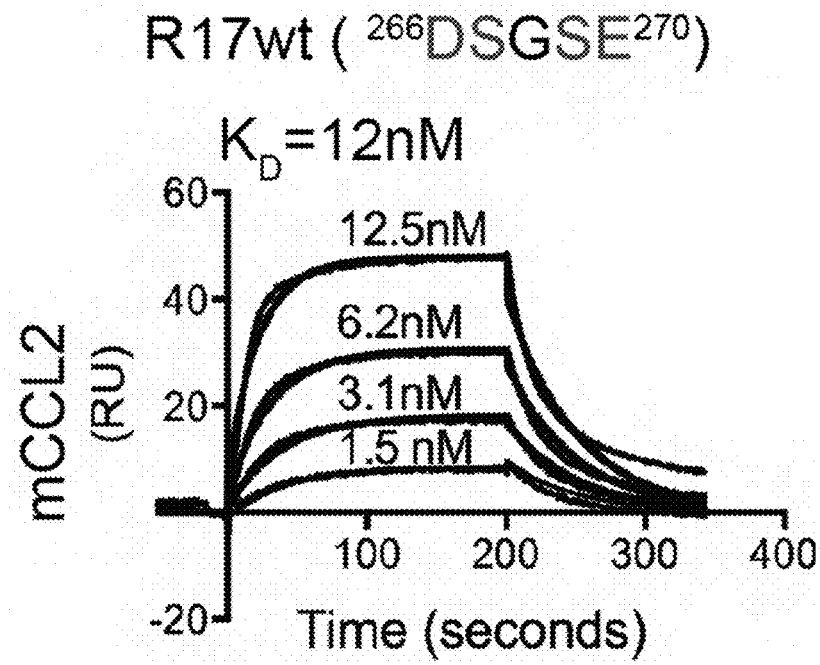
Figure 8C:
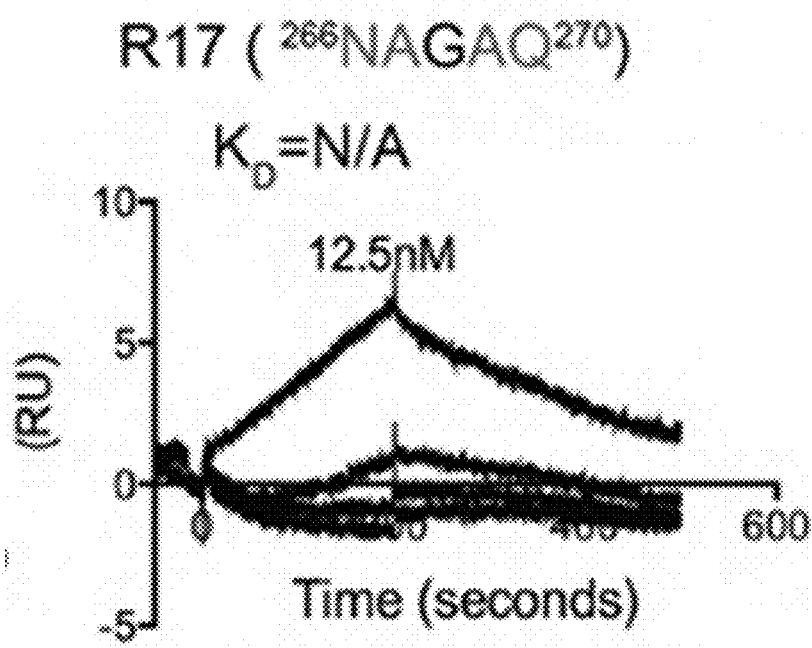
Figure 8D:
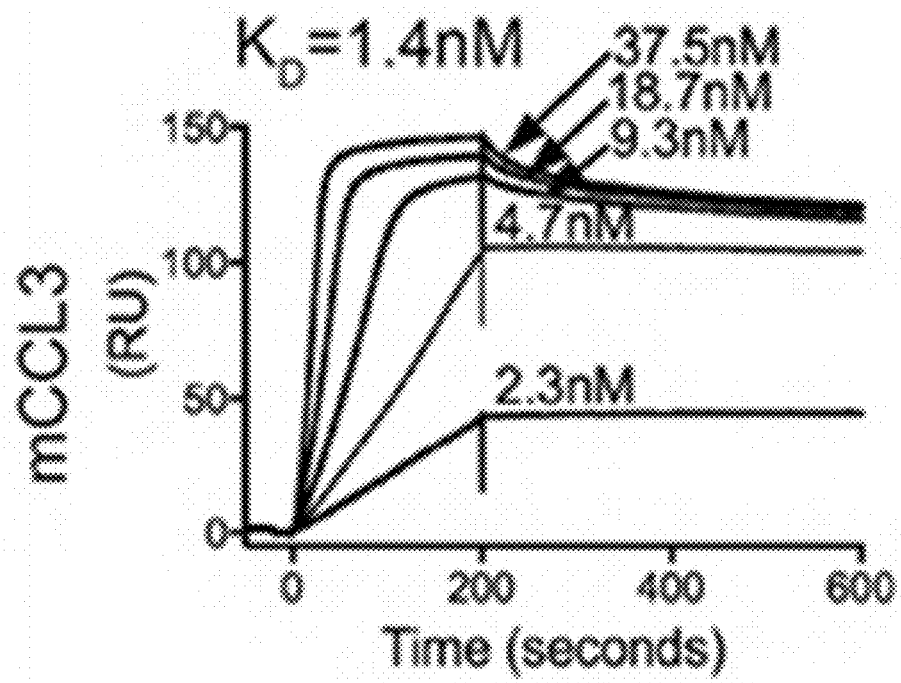
Figure 8E:
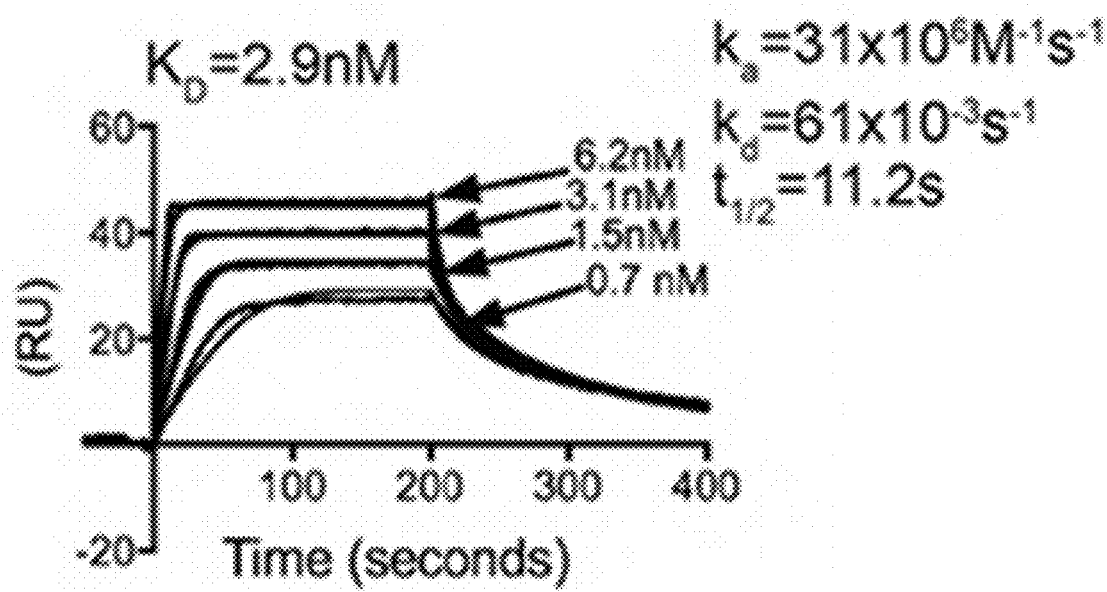
Figure 9A:
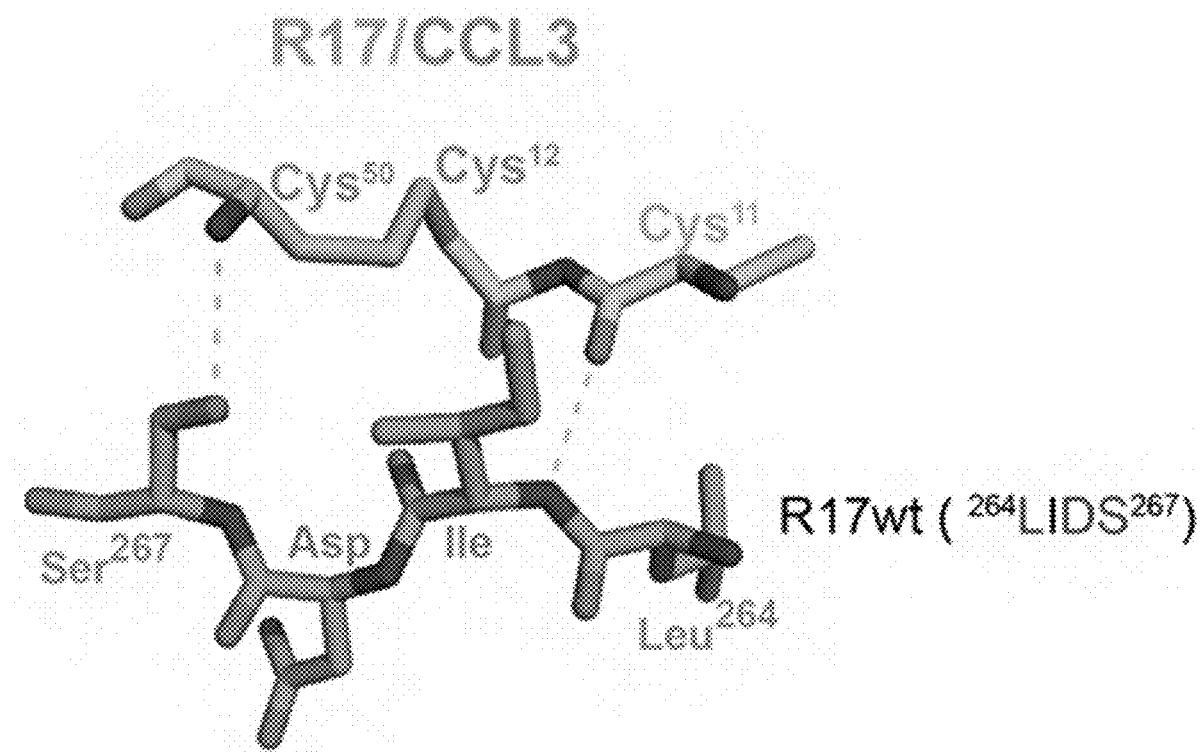
FIG. 9A and FIG. 9B show R17 chemokine null mutant. The invariant disulfide bond (Cys12-Cys51/52) of CCL3 and flanking Cys11 is packed against hydrophobic 264LIDS267 motif of R17 and is depicted in ball and stick representation. A mutant R17 created with $^{264}LIDS^{267}$ (SEQ ID NO:5) replaced with the residues $^{264}GG(G)DS^{267}$ (aa 264 to 267 of SEQ ID NO:1) abolishes the ability of R17 to bind hCCL3 as assessed by SPR.
Figure 9B:
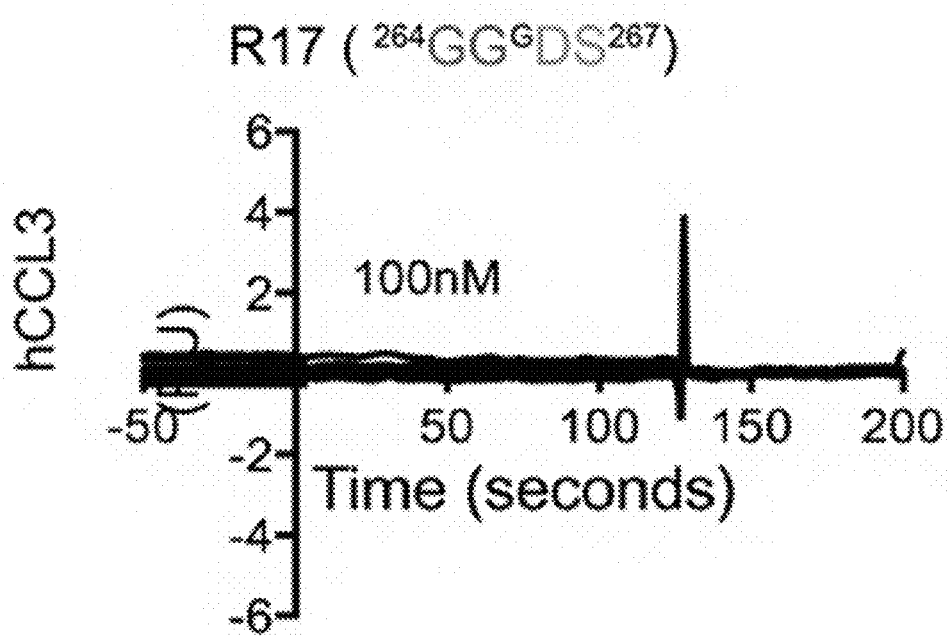

Example 8: Infusion of R17 into Donor Mouse Lungs Sharply Inhibits IRI-Mediated Intrapulmonary Neutrophil Accumulation Following Transplantation 10 independent lung transplant experiments using R17 proteins were performed using laboratory mice. A donor lungs was harvested, and before transplantation the donor lungs were infused with a perfusion solution containing R17, R17 with GAG binding motif mutated, or PBS, for the R17, mutated R17, and control group, respectively, with 8 mice in each group. R17-GAG mutants has a mutation in the GAG binding and can no longer bind epithelium. R17His is a wild type protein. The lungs were transplanted into respectively prepared recipient mice. Flow cytometry was conducted on cells taken from Brancheolar lavages 90 min post reperfusion following eight independent transplants. The cells were labeled with Ly6C and Ly6G. Ly6C was used as a marker of circulating monocytes. Ly6G was used as a marker for granulocytes and neutrophils. Ly6C and Ly6G decreased significantly in the group treated with wild type RE17, compared to the group treated with R17 with the mutated GAG or the control (FIG. 6). Indicating that R17 inhibits movement of these granulocytes into the lung, by sequestering the chemokines that would induce chemotaxis. Infusion of R17 into donor mouse lungs sharply inhibits IRI-mediated intrapulmonary neutrophil accumulation following transplantation. If the R17 GAG binding motif is mutated, intrapulmonary neutrophilia is restored suggesting that R17 may regulated neutrophil recruitment by modulating CC- and C-chemotaxis gradient near or around homeostatic barriers such as vascular endothelial and airway epithelium, both of which express GAGS (FIG. 7).

REFERENCES FOR EXAMPLES 1-8

1. Loh J, Zhao G, Nelson C A, Coder P, Droit L, Handley S A, Johnson L S, Vachharajani P, Guzman H, Tesh R B, Wang D, Fremont D H, Virgin H W. 2011. Identification and sequencing of a novel rodent gammaherpesvirus that establishes acute and latent infection in laboratory mice. J. Virol. 85:2642-2656. 10.1128/JVI.01661-10
2. Virgin H W, IV, Latreille P, Wamsley P, Hallsworth K, Weck K E, Dal Canto A J, Speck S H. 1997. Complete sequence and genomic analysis of murine gammaherpesvirus 68. J. Virol. 71:5894-5904
3. Russo J J, Bohenzky R A, Chien M C, Chen J, Yan M, Maddalena D, Parry J P, Peruzzi D, Edelman I S, Chang Y, Moore P S. 1996. Nucleotide sequence of the Kaposi sarcoma-associated herpesvirus (HHV8). Proc. Natl. Acad. Sci. U.S.A. 93:14862-14867. 10.1073/pnas.93.25.14862
4. Herr R A, Wang X, Loh J, Virgin H W, Hansen T H. 2012. Newly discovered viral E3 ligase pK3 induces endoplasmic reticulum-associated degradation of class I major histocompatibility proteins and their membrane-bound chaperones. J. Biol. Chem. 287:14467-14479. 10.1074/jbc.M111.325340
5. Alcami A, Koszinowski U H. 2000. Viral mechanisms of immune evasion. Immunol. Today 21:447-455. 10.1016/S0167-5699(00)01699-6
6. Seet B T, Johnston J B, Brunetti C R, Barrett J W, Everett H, Cameron C, Sypula J, Nazarian S H, Lucas A, McFadden G. 2003. Poxviruses and immune evasion. Annu. Rev. Immunol. 21:377-423. 10.1146/annurev.immunol.21.120601.141049
7. Murphy P M. 2001. Viral exploitation and subversion of the immune system through chemokine mimicry. Nat. Immunol. 2:116-122. 10.1038/84214
8. Epperson M L, Lee C A, Fremont D H. 2012. Subversion of cytokine networks by virally encoded decoy receptors. Immunol. Rev. 250:199-215. 10.1111/imr.12009

9. Alcami A, Lira S A. 2010. Modulation of chemokine activity by viruses. Curr. Opin. Immunol. 22:482-487. 10.1016/j.coi.2010.06.004
10. Alcami A, Smith G L. 1995. Vaccinia, cowpox, and camelpox viruses encode soluble gamma interferon receptors with novel broad species specificity. J. Virol. 69:4633-4639
11. Alcami A, Smith G L. 2002. The vaccinia virus soluble interferon-gamma receptor is a homodimer. J. Gen. Virol. 83:545-549
12. Strockbine L D, Cohen J I, Farrah T, Lyman S D, Wagener F, DuBose R F, Armitage R J, Spriggs M K. 1998. The Epstein-Barr virus BARF1 gene encodes a novel, soluble colony-stimulating factor-1 receptor. J. Virol. 72:4015-4021 [PMC free article] [PubMed]
13. Lau E K, Allen S, Hsu A R, Handel T M. 2004. Chemokine-receptor interactions: GPCRs, glycosaminoglycans and viral chemokine binding proteins. Adv. Protein Chem. 68:351-391. 10.1016/S0065-3233(04)68010-7
14. Alexander J M, Nelson C A, van Berkel V, Lau E K, Studts J M, Brett T J, Speck S H, Handel T M, Virgin H W, Fremont D H. 2002. Structural basis of chemokine sequestration by a herpesvirus decoy receptor. Cell 111: 343-356. 10.1016/S0092-8674(02)01007-3
15. Alexander-Brett J M, Fremont D H. 2007. Dual GPCR and GAG mimicry by the M3 chemokine decoy receptor. J. Exp. Med. 204:3157-3172. 10.1084/jem.20071677
16. Wang D, Bresnahan W, Shenk T. 2004. Human cytomegalovirus encodes a highly specific RANTES decoy receptor. Proc. Natl. Acad. Sci. U.S.A. 101:16642-16647. 10.1073/pnas.0407233101
17. Viejo-Borbolla A, Martinez-Martin N, Nel H J, Rueda P, Martin R, Blanco S, Arenzana-Seisdedos F, Thelen M, Fallon P G, Alcami A. 2012. Enhancement of chemokine function as an immunomodulatory strategy employed by human herpesviruses. PLoS Pathog. 8:e1002497. 10.1371/journal.ppat.1002497
18. Graham K A, Lalani A S, Macen J L, Ness T L, Barry M, Liu L Y, Lucas A, Clark-Lewis I, Moyer R W, McFadden G. 1997. The T1/35 kDa family of poxvirus-secreted proteins bind chemokines and modulate leukocyte influx into virus-infected tissues. Virology 229:12-24. 10.1006/viro.1996.8423
19. Alcami A, Symons J A, Collins P D, Williams T J, Smith G L. 1998. Blockade of chemokine activity by a soluble chemokine binding protein from vaccinia virus. J. Immunol. 160:624-633
20. Arnold P L, Fremont D H. 2006. Structural determinants of chemokine binding by an ectromelia virus-encoded decoy receptor. J. Virol. 80:7439-7449. 10.1128/JVI.00576-06
21. Lalani A S, Graham K, Mossman K, Rajarathnam K, Clark-Lewis I, Kelvin D, McFadden G. 1997. The purified myxoma virus gamma interferon receptor homolog M-T7 interacts with the heparin-binding domains of chemokines. J. Virol. 71:4356-4363
22. Bahar M W, Kenyon J C, Putz M M, Abrescia N G, Pease J E, Wise E L, Stuart D I, Smith G L, Grimes J M. 2008. Structure and function of A41, a vaccinia virus chemokine binding protein. PLoS Pathog. 4:e5. 10.1371/journal.ppat.0040005
23. Ruiz-Arguello M B, Smith V P, Campanella G S, Baleux F, Arenzana-Seisdedos F, Luster A D, Alcami A. 2008. An ectromelia virus protein that interacts with chemokines through their glycosaminoglycan binding domain. J. Virol. 82:917-926. 10.1128/JVI.02111-07
24. Alejo A, Ruiz-Arguello M B, Ho Y, Smith V P, Saraiva M, Alcami A. 2006. A chemokine-binding domain in the tumor necrosis factor receptor from variola (smallpox) virus. Proc. Natl. Acad. Sci. U.S.A. 103:5995-6000. 10.1073/pnas.0510462103
25. Lalani A S, Masters J, Graham K, Liu L, Lucas A, McFadden G. 1999. Role of the myxoma virus soluble CC-chemokine inhibitor glycoprotein, M-T1, during myxoma virus pathogenesis. Virology 256:233-245. 10.1006/viro.1999.9617 [PubMed] [Cross Ref]
26. Lateef Z, Baird M A, Wise L M, Mercer A A, Fleming S B. 2009. Orf virus-encoded chemokine-binding protein is a potent inhibitor of inflammatory monocyte recruitment in a mouse skin model. J. Gen. Virol. 90:1477-1482. 10.1099/vir.0.009589-0
27. Lateef Z, Baird M A, Wise L M, Young S, Mercer A A, Fleming S B. 2010. The chemokine-binding protein encoded by the poxvirus ORF virus inhibits recruitment of dendritic cells to sites of skin inflammation and migration to peripheral lymph nodes. Cell. Microbiol. 12:665-676. 10.1111/j.1462-5822.2009.01425.x
28. van Berkel V, Levine B, Kapadia S B, Goldman J E, Speck S H, Virgin H W., IV 2002. Critical role for a high-affinity chemokine-binding protein in gamma-herpesvirus-induced lethal meningitis. J. Clin. Invest. 109: 905-914. 10.1172/JCI14358
29. Hughes D J, Kipar A, Sample J T, Stewart J P. 2010. Pathogenesis of a model gammaherpesvirus in a natural host. J. Virol. 84:3949-3961. 10.1128/JVI.02085-09
30. Hughes D J, Kipar A, Leeming G H, Bennett E, Howarth D, Cummerson J A, Papoula-Pereira R, Flanagan B F, Sample J T, Stewart J P. 2011. Chemokine binding protein M3 of murine gammaherpesvirus 68 modulates the host response to infection in a natural host. PLoS Pathog. 7:e1001321. 10.1371/journal.ppat.1001321
31. Proudfoot A E, Borlat F. 2000. Purification of recombinant chemokines from E. coli. Methods Mol. Biol. 138: 75-87
32. Miley M J, Truscott S M, Yu Y Y, Gilfillan S, Fremont D H, Hansen T H, Lybarger L. 2003. Biochemical features of the MHC-related protein 1 consistent with an immunological function. J. Immunol. 170:6090-6098
33. Kelley L A, Sternberg M J. 2009. Protein structure prediction on the Web: a case study using the Phyre server. Nat. Protoc. 4:363-371. 10.1038/nprot.2009.2
34. Houser B. 2012. Bio-Rad's Bio-Plex® suspension array system, xMAP technology overview. Arch. Physiol. Biochem. 118:192-196. 10.3109/13813455.2012.705301
35. Cyster J G. 1999. Chemokines and cell migration in secondary lymphoid organs. Science 286:2098-2102. 10.1126/science.286.5447.2098
36. Moser B, Loetscher P. 2001. Lymphocyte traffic control by chemokines. Nat. Immunol. 2:123-128. 10.1038/84219
37. Jensen K K, Chen S C, Hipkin R W, Wiekowski M T, Schwarz M A, Chou C C, Simas J P, Alcami A, Lira S A. 2003. Disruption of CCL21-induced chemotaxis in vitro and in vivo by M3, a chemokine-binding protein encoded by murine gammaherpesvirus 68. J. Virol. 77:624-630. 10.1128/JVI.77.1.624-630.2003
38. Maghazachi A A. 2000. Intracellular signaling events at the leading edge of migrating cells. Int. J. Biochem. Cell Biol. 32:931-943. 10.1016/S1357-2725(00)00035-2
39. van Berkel V, Barrett J, Tiffany H L, Fremont D H, Murphy P M, McFadden G, Speck S H, Virgin H I. 2000. Identification of a gammaherpesvirus selective chemokine binding protein that inhibits chemokine action. J. Virol. 74:6741-6747. 10.1128/JVI.74.15.6741-6747.2000
40. Proudfoot A E, Handel T M, Johnson Z, Lau E K, LiWang P, Clark-Lewis I, Borlat F, Wells T N, Kosco-Vilbois M H. 2003. Glycosaminoglycan binding and oligomerization are essential for the in vivo activity of certain chemokines. Proc. Natl. Acad. Sci. U.S.A 100: 1885-1890. 10.1073/pnas.0334864100
41. Esko J D, Weinke J L, Taylor W H, Ekborg G, Roden L, Anantharamaiah G, Gawish A. 1987. Inhibition of chondroitin and heparan sulfate biosynthesis in Chinese hamster ovary cell mutants defective in galactosyltransferase I. J. Biol. Chem. 262:12189-12195
42. Cardin A D, Weintraub H J. 1989. Molecular modeling of protein-glycosaminoglycan interactions. Arteriosclerosis 9:21-32. 10.1161/01.ATV.9.1.21
43. Hileman R E, Fromm J R, Weiler J M, Linhardt R J. 1998. Glycosaminoglycan-protein interactions: definition of consensus sites in glycosaminoglycan binding proteins. Bioessays 20:156-167. 10.1002/(SICI)1521-1878(199802)20:2<156::AID-BIES8>3.0.CO;2-R
44. Lau E K, Paavola C D, Johnson Z, Gaudry J P, Geretti E, Borlat F, Kungl A J, Proudfoot A E, Handel T M. 2004. Identification of the glycosaminoglycan binding site of the CC chemokine, MCP-1: implications for structure and function in vivo. J. Biol. Chem. 279:22294-22305. 10.1074/jbc.M311224200
45. Seet B T, Barrett J, Robichaud J, Shilton B, Singh R, McFadden G. 2001. Glycosaminoglycan binding properties of the myxoma virus CC-chemokine inhibitor, M-T1. J. Biol. Chem. 276:30504-30513. 10.1074/jbc.M011401200 [PubMed] [Cross Ref]
46. Lucas A, McFadden G. 2004. Secreted immunomodulatory viral proteins as novel biotherapeutics. J. Immunol. 173:4765-4774
47. Dabbagh K, Xiao Y, Smith C, Stepick-Biek P, Kim S G, Lamm W J, Liggitt D H, Lewis D B. 2000. Local blockade of allergic airway hyperreactivity and inflammation by the poxvirus-derived pan-CC-chemokine inhibitor vCCI. J. Immunol. 165:3418-3422
48. Bursill C A, Cai S, Channon K M, Greaves D R. 2003. Adenoviral-mediated delivery of a viral chemokine binding protein blocks CC-chemokine activity in vitro and in vivo. Immunobiology 207:187-196. 10.1078/0171-2985-00228
49. Liu L, Dai E, Miller L, Seet B, Lalani A, Macauley C, Li X, Virgin H W, Bunce C, Turner P, Moyer R, McFadden G, Lucas A. 2004. Viral chemokine-binding proteins inhibit inflammatory responses and aortic allograft transplant vasculopathy in rat models. Transplantation 77:1652-1660. 10.1097/01.TP.0000131173.52424.84
50. Rice J, de Lima B, Stevenson F K, Stevenson P G. 2002. A gamma-herpesvirus immune evasion gene allows tumor cells in vivo to escape attack by cytotoxic T cells specific for a tumor epitope. Eur. J. Immunol. 32:3481-3487. 10.1002/1521-4141(200212)32:12<3481::AID-IMMU3481>3.0.CO;2-J
51. Pyo R, Jensen K K, Wiekowski M T, Manfra D, Alcami A, Taubman M B, Lira S A. 2004. Inhibition of intimal hyperplasia in transgenic mice conditionally expressing the chemokine-binding protein M3. Am. J. Pathol. 164: 2289-2297. 10.1016/S0002-9440(10)63785-6
52. Martin A P, Canasto-Chibuque C, Shang L, Rollins B J, Lira S A. 2006. The chemokine decoy receptor M3 blocks CC chemokine ligand 2 and CXC chemokine ligand 13 function in vivo. J. Immunol. 177:7296-7302.

Example 9: Administration of Chemokine Decoys to Prevent Myocardial Reperfusion Injury The upregulation of both CC and CXC chemokines is a hallmark of the inflammatory responses following myocardial infarction. In particular chemokine-driven adhesive interactions between endothelial cells and leukocytes mediate extravasation of immune cells into the infarct. CXC chemokines (such as interleukin-8) are bound to glycosaminoglycans on the endothelial surface and activate captured neutrophils, inducing expression of integrins. CC chemokines (such as monocyte chemoattractant protein (MCP)-1) mediate recruitment of proinflammatory and phagocytotic mononuclear cells into the infarct. Although there is extensive experimental evidence that the neutralization of chemokines can lead to reductions in infarct size, data from clinical trials show that current available blocking agents cannot adequately inhibit the many chemokine signals that regulate this type injury. Viral chemokine decoys such as R17, T17, or M3 given their modulatable specifities for large numbers of different CC and CXC chemokines represent a first in class immunotherapeutic approach to inhibit lesion development following myocardial infarction. Localization of R17 and T17 to GAG sites after injection could also prove to be therapeutically critical.

In Vivo I/R Protocol

Mice will be initially anaesthetized with 4% isoflurane and intubated. After starting mechanical ventilation by supplementation with 100% oxygen, anesthesia will be maintained with 2% isoflurane. A thoracotomy will be performed in the left third intercostal space and the pericardium will be removed. Ligature of the left anterior coronary artery at the inferior edge of the left atrium will be done using an 8-0 Prolene suture. A small piece of polyethylene tube will be used to secure the ligature without damaging the artery. After 5 minutes of ischemia, R17, T17, or M3 (1, 10 or 100 µg/mouse, recombinant compound prepared as previously described), combinations of these factors, or control vehicle (PBS) will be administered by intraperitoneal injection. After 30 min of ischemia, the occlusion of the left anterior coronary artery occlusion will be released and reperfusion occurred. Reperfusion will be confirmed by visible restoration of color to the ischemic tissue. Then, chest will be closed and the ventilator removed to restore normal respiration. Sham-operated animals were submitted to the same surgical protocol as described but without arterial occlusion. At different reperfusion time points, animals will be sacrificed for infarct size determination, immunohistochemical, and western blot or RNA analysis.

Ex Vivo I/R

The technique of Langendorff isolated buffer-perfused mouse heart preparation will be used (Entman M L, Smith C W, 1994). The heart will be rapidly excised and placed in ice-cold Krebs-Henseleit bicarbonate (KHB) buffer consisting of (in mmol/L): 118.5 NaCl, 25 NaHCO3, 4.7 KCl, 1.2 MgSO4, 1.2 KH2PO4, 2.5 CaCl2), 5 glucose and equilibrated with 95% 02, 5% CO2 (pH 7.4). The extraneous tissues (pericardium, lung, trachea, etc) will be removed. The aorta will be cannulated with an 18-G plastic cannula (1.5 cm length; 0.95 mm, inner diameter) for a Langendorff retrograde perfusion. After stabilization, ligature of the left anterior coronary artery at the inferior edge of the left atrium will be performed using an 8-0 Prolene suture. A small piece of polyethylene tubing will used to secure the ligature without damaging the artery and ventricle tissue. After 5 min ischemia, R17, T17, or M3 (5 µg/ml) or vehicle will be added within the circulating Langendorff system. On the basis of previous in vitro and in vivo experiments and the present in vivo I/R experiments. After 30 min ischemia, the polyethylene tube will be removed and reperfusion will be allowed for additional 2 hours.

Area at Risk (AAR) and Infarct Size (I) Assessment

To assess area at risk (AAR) and infarct size (I) in in vivo I/R protocol, mice will be anaesthetized with ketamine-xylazine and sacrificed after 2 h, 8 h and 24 h of reperfusion, as described (Birdsall H H, G et al., 1997).

Example 10: Administration of R17 to Mouse Lung Transplants

Donor lung procurement: Prior to R17 administration left lungs from donor mice are intubated with a 20 G angiocatheter via a tracheotomy and placed on a Harvard ventilator under anesthesia (Ketamine 0.1 mg/g body weight & Xylazine 0.01 mg/g body weight). Mice are ventilated with room air at a tidal volume of 0.5 mL and a respiratory rate of 120/min. Then a median laparosternotomy is performed and 100 units of heparin are administered intravenously. Heparin is then removed with three-2 mL flushes of cold (4° C.) low-potassium dextran glucose solution through the pulmonary artery. Upon completion of flushes heart-lung block is harvested with the lungs inflated at end-tidal volume and the left lung is isolated and prepared for placement of cuffs. The cuff for the pulmonary artery is fashioned from a 24 G Teflon catheter. Cuffs for both pulmonary veins and bronchus are prepared from a 20 G Teflon catheter. The pulmonary artery is passed through the cuff, the proximal end is everted over the cuff and then firmly fixed with a circumferential 10-0 nylon ligature. A cuff is placed on the pulmonary veins in analogous fashion.

R17 extracorporeal administration: Following placement of cuffs 2.5 mls of R17 (100 ug/ml) in 4° C. normal saline is administered through pulmonary artery at a rate of 0.5 ml/min using a Harvard syringe. R17 is also added at 10 ug/ml to low-potassium dextran glucose and then is stored in this solution at 4° C. for at least one hour prior to transplantation.

Lung engraftment into recipient: Lung engraftment is performed as described by Okazaki et al 2007 AJT. After induction of anesthesia recipient mice are intubated orotracheally with a 20 G angiocatheter. The recipients are additionally maintained under general anesthesia with a mixture of isoflurane and oxygen. A left thoracotomy is performed through the third intercostal space. A clamp is attached to the left lung and the lung is retracted laterally in order to expose the hilum. The hilum of the left lung is dissected, and the left main bronchus is clamped with a microvascular clamp. The pulmonary artery and pulmonary veins are occluded with a slip knot (10-0 silk suture). Slip knots are used because of the ease of their release after implantation. An incision is then made in each of these structures in preparation for the insertion of the cuffs. The donor lung is removed from R17 treated cold storage solution and flushed with 1.0 ml of normal saline and the bronchial cuff is attached. Similar to the pulmonary artery and pulmonary veins the end of the bronchus is passed through the 20 G Teflon cuff, the proximal end is folded over the cuff and then secured with a circumferential 10-0 nylon ligature. The lung is implanted by inserting donor pulmonary artery, pulmonary veins and bronchus into the respective recipient structures through the previously made incisions. The cuffs are secured with 10-0 nylon suture ligatures. The transplanted lung is reinflated and reperfused by releasing the microvascular clamp on the recipient bronchus and releasing the slip knots on the vascular structures. The thoracotomy is closed in two layers and the recipient mouse is extubated.

Example 11: Mutation of R17 Chemokine Binding Domain

Structure based mutations of R17 were created to modulate the binding of chemokines. Mutated residues were selected based on their location in the crystal structure of R17 in complex with CCL3 and introduced using Multi-Site Quick Change Mutagenesis Kit (Agilent Technologies) on the background of the wild type R17 C-terminal His construct and verified by DNA sequencing. R17 was either selectively mutated to remove the negative charge from $^{266}$DSGSE$^{270}$ (SEQ ID NO: 9) to $^{266}$NAGAQ$^{270}$ (SEQ ID NO: 10) or a core hydrophobic chemokine binding motif of R17 was mutated from $^{264}$LIDS$^{267}$ to $^{264}$GG$^G$DS$^{267}$ (SEQ ID NO: 11) where G superscript denotes Glycine insertion. Surface plasmon resonance (SPR) binding was used to directly measure the affinity and kinetics of chemokine binding by R17 and its chemokine binding variants. R17$^{wt}$, R17 $^{266}$NAGAQ$^{270}$ (SEQ ID NO: 10) and R17 $^{264}$GG$^G$DS$^{267}$ (SEQ ID NO: 11) were immobilized on a CM5 chip (GE Healthcare) using standard amine coupling chemistry (BIAcore Amine coupling kit) to a level of 1000 response units using a Biacore T-100 biosensor (GE Healthcare). A control flow cell was prepared by coupling a non-chemokine binding protein, neutroavidin, to the chip at similar level. Experiments were performed at 50 µl/min and 25° C. using HBS-EP (10 mM HEPES [pH 7.5], 150 mM NaCl, 3 mM EDTA, 0.005% Tween 20) as a running buffer. 300 ul of either CCL2 or CCL3 was injected over the experimental and control flow cells followed by a 10 min period to monitor dissociation before regeneration was achieved by injecting 100 µl of Glycine pH2.0. Each experiment was performed three times with eight different chemokine concentrations. The association ($k_a$) and the dissociation ($k_d$) values were determined simultaneously by globally fitting sensograms for an entire range of chemokine concentrations to a 1:1 mass transport model with BIAevaluation software. This global analysis was performed independently for each series of concentrations, the resulting values were averaged and the standard deviation was calculated to reflect the experimental error.

Example 12: Rodent Herpesvirus Texas (RHVT) Encodes a High Affinity Chemokine Decoy Receptor Recently, the genome of another rhadinovirus, rodent herpesvirus Texas (RHVT), became available. Like other gamma-herpesviruses, RHVT encodes proteins that are hypothesized to be involved in immune evasion. Of particular interest is the ORF located at the end of the RHVT genome encoding T17, a gene product that we determined shares low sequence similarity with R17, a known chemokine-binding protein from RHVP. As the ORF encoding T17 is located at the end of the RHVT genome and shares sequence similarity with R17, we hypothesize that it is also a chemokine-binding protein. These findings suggest that gamma-herpesviruses-encoded chemokine-binding proteins may share common structural features. Fold-threading algorithms (Phyre2) suggest that T17's GAG-binding site and some chemokine-binding residues are conserved between T17 and R17, but T17 is likely to have a different binding specificity as some key chemokine-binding residues from R17 are not conserved. This presents an opportunity to understand and examine the molecular determinants responsible for chemokine binding specificity.

Here we determine that T17 is indeed a chemokine-binding protein that broadly recognizes a subset of C, CC, and CXC chemokines and can interact directly with cell surfaces via GAGs. Much like R17, we show that T17 is a potent antagonist of chemokine signaling.

Materials and Methods

Cloning, Expression, and Purification of T17

The mature form of T17 was amplified from RHVT genomic DNA without its endogenous leader peptide and cloned into a mammalian expression vector (mammalian POE vector) in frame with a CD33 leader peptide in place of the endogenous leader sequence as a C-terminal His tag (6 histidine residues) fusion protein. In this vector, a CMV promoter controls the expression of T17. The vector also expresses the EBNA protein from EBV, which enhances DNA replication and thus gene expression. The construct encoding T17 was transfected into six 200 ml flasks of mammalian Expi293F cells, each at a concentration of $1 \times 10^6$ cells/ml, for expression. For each flask of cells, 250 µg of T17 DNA was transfected into Expi293F cells using Hype-5 (OZBiosciences) as the transfection reagent. Mammalian Expi293F cells were cultured in Expi293 expression medium (Thermo Fisher Scientific) and incubated at 37° C. at 5% $CO_2$. 24 hours post-transfection, 50 ml of Expi293 medium and 10 ml of 2% Hyclone Cell Boost (GE Healthcare) were added to cells. 50 ml Expi293 of medium and 20 ml of 2% Hyclone Cell Boost were added to cells 48 hours post-transfection, and 30 ml of 2% Hyclone Cell Boost was added to cells 72 hours following transfection. The culture supernatant was harvested four days after transfection to collect T17 that was secreted into the media, centrifuged at 1000 rpm for 10 minutes, and filtered. The supernatant was concentrated using a pre-soaked 30 kDa membrane filter. The supernatant was then buffer exchanged into phosphate buffered saline (PBS). Concentrated T17 was loaded onto a column with nickel-agarose beads (Qiagen) for purification. The column was washed with 10 mM imidizole and the protein eluted with 250 mM imidizole. The elution was concentrated using a 30 kDa spin column (Amicon-Ultra) and subsequently loaded onto HiLoad 16/600 Superdex S200 size exclusion column (GE Healthcare). SDS-PAGE gel and Western blots were used to confirm protein purity.

Biotinylation

Random biotinylation of T17 was carried out using EZ-Link N-Hydroxysulfosuccinimide (NHS)-polyethylene glycol 4 (PEG4)-biotin (Thermo FisherScientific) at a 2:1 molar ratio of biotin to protein per manufacturer's instructions. 9 mg of T17 was biotinylated. The biotinylation reaction was incubated at room temperature for 30 minutes. The biotinylation reaction was loaded onto a Thermo Scientific Zebra spin desalting column and was centrifuged at 1200 rpm for 2 minutes to remove free biotin.

Protein Expression and Purification from *E. coli*

Constructs for hCCL2 and M3 were cloned into a pET28A vector and transformed into BL21-CodonPlus (DE3)-RIL *E. coli* cells. Expression was carried out in LB medium supplemented with ampicillin and chloramphenicol. When the cell culture reached an optical density of 0.6, protein expression was induced with 1 mM IPTG. Cells were suspended in 100 ml of a solution buffer (50 mM Tris-HCl [pH=8.0], 1 mM EDTA [pH=8.0], 0.01% sodium azide, 1 mM DTT, and 25% sucrose) and sonicated on ice four times to lyse the cells (30 seconds each). 10 ml of lysozyme (at a concentration of 10 mg/ml), 10 ml of DNase I (at a concentration of 10 mg/ml), and 2.5 ml of a divalent cation solution (400 mM $MgCl_2$+400 mM $CaCl_2$) were added to the lysed cells, and stirred at room temperature for 20 minutes. 100 ml of lysis buffer (50 mM Tris-HCl [pH=8.0], 1 mM EDTA [pH=8.0], 0.01% sodium azide, 1 mM DTT, 200 mM NaCl, 1% sodium deoxycholate, and 1% Triton X-100) was added and the mixture was incubated on ice for 1 hour with constant stirring. The mixture was then sonicated three times (60 seconds each). 10 ml of 0.5M EDTA (pH=8.0) was added and the insoluble protein was pelleted by centrifugation (6000×g for 15 minutes). Inclusion bodies were washed three times with a wash buffer (50 mM Tris-HCl [pH=8.0], 1 mM EDTA [pH=8.0], 0.01% sodium azide, 1 mM DTT, 100 mM NaCl, and 0.5% Triton X-100). To remove the detergent, the inclusion bodies were washed with a wash buffer without Triton X-100 (50 mM Tris-HCl [pH=8.0], 1 mM EDTA [pH=8.0], 0.01% sodium azide, 1 mM DTT, and 100 mM NaCl).

Approximately 100 mg of inclusion body was used for refolding hCCL2, and 150 mg was used for refolding M3. 400 ml of refolding buffer was prepared for the refolding reaction (400 mM L-arginine, 100 mM Tris-HCl [pH=8.0], 2 mM EDTA [pH=8.0], 5 mM reduced glutathione, 0.5 mM oxidized glutathione, and 0.2 mM PMSF). For refolding M3, 400 mM NDSB 201 was used in place of L-arginine and 0.2 mM PMSF was not added to facilitate protein refolding. The refolding buffer was filtered through a 0.2 µm filter and refrigerated at 4° C. on a stir plate at a low stir speed. The reduced and oxidized glutathione, and PMSF (for refolding hCCL2) were added to the refolding buffer right before refolding. 5 ml of solubilization buffer was prepared for solubilizing inclusion bodies (6M guanidine-HCl, 20 mM β-mercaptoethanol, and 10 mM Tris-HCl [pH=8.0]). Inclusion bodies were dissolved in the solubilization buffer and incubated at room temperature for 10 minutes. Solubilization buffer was then distributed into 1 ml aliquots and centrifuged at 13,200 rpm for 5 minutes to remove insoluble contaminants. The stirring speed of the refolding buffer was intensified until a significant vortex formed. 1 ml of solubilized inclusion body was injected one drop at a time into the refolding buffer. The stirring speed was reduced until the stir bar is just spinning. Injections were repeated once every hour until all of the solubilized protein has been diluted into the refolding buffer. Following the last injection, the refolding reaction was allowed to continue overnight at 4° C. The refolding reaction was filtered through a 0.2 µm filter and concentrated using a pre-soaked 10 kDa membrane filter (for M3, a pre-soaked 30 kDa membrane filter was used instead) until approximately 10 ml of solution remained. Refolded hCCL2 was purified using HiLoad 16/600 Superdex S75 size exclusion column (GE Healthcare) followed by cleanup over HiTrap SP HP column (GE Healthcare). Refolded M3 was purified using HiLoad 16/600 Superdex S200 size exclusion column (GE Healthcare). SDS-PAGE confirmed purity of refolded proteins.

BLI Binding Assays

Bio-layer interferometry (BLI) binding assays were carried out using the Octet Red system (Forte Bio) to screen for binding of all commercially available chemokines and to determine the kinetics of CXC and C chemokine binding by T17. Streptavidin-coated biosensors were soaked in Octet buffer (10 mM HEPES [pH=7.5], 150 mM NaCl, 3 mM EDTA, 0.005% Tween 20, and 1% BSA) for 1 hour prior to experiments. Biotinylated T17 and chemokines were diluted with the Octet buffer to 50 µg/ml and to eight different concentrations ranging from 0 nM to 250 nM, respectively. A 96-well plate was loaded with the prepared chemokine dilutions and T17 30 minutes prior to carrying out binding experiments. A total of three chemokines (eight concentrations each) were loaded onto a 96-well plate at one time. All steps of the binding assays were carried out at room temperature with shaking at 1000 rpm. Streptavidin-coated biosensors were dipped into buffer for 60 seconds to establish a baseline. The biosensors were then allowed to associate T17 for 120 seconds and dissociate into buffer for 60 seconds to wash off unbound protein. The biosensors were submerged in wells containing increasing concentrations of a chemokine for 180 seconds and then washed in buffer for 200 seconds for the chemokines to dissociate. Each step was repeated for the remaining chemokines with new biosensors. Association values (IQ, dissociation (Ka) values, dissociation constants (KD, kin), and equilibrium dissociation constants (KD, eq) were determined by fitting the sensograms for the range of tested chemokine concentrations to a 1:1 mass transport model using BIAevalution software (GE Healthcare). Half-life values were calculated based on the following equation: $t\frac{1}{2}=\ln 2/kd$.

SPR Binding Analysis

Surface plasmon resonance (SPR) binding assays were carried out using a Biacore T-100 instrument (GE Healthcare). SPR was used to measure the affinity and to determine the kinetics of CC chemokine binding by T17. 500 to 1000 response units (RU) of T17 and R17 (negative control) were coupled to a CMS chip (GE Healthcare) using amine coupling chemistry (Biacore amine coupling kit). Flow rate for coupling was set at 5111/min. NeutrAvidin was coupled to a control flow cell at a level similar to those for T17 and R17. Binding experiments were performed at room temperature with a flow rate of 80111/min using a HBS-EP buffer as the running buffer (10 mM HEPES [pH 7.5], 150 mM NaCl, 3 mM EDTA, and 0.005% Tween 20). Titration curves for each chemokine was set up with at least eight different concentrations, ranging from 1.25 nM to 100 nM, followed by three buffer injections to assess the baseline. Each chemokine concentration was injected for 200 seconds into each flow cell. This was followed by a 300-second dissociation period. 20p1 of glycine (pH=2.0) was used for regeneration to remove chemokine that has accumulated on the surface of the flow cell after each injection. Association values (IQ, dissociation (Ka) values, dissociation constants (KD, kin), and equilibrium dissociation constants (KD, eq) were determined by globally fitting the sensograms for the range of tested chemokine concentrations to a 1:1 mass transport model using BIAevalution software (GE Healthcare).

Chemotaxis Assays

Jurkat T cells (human T lymphocytes derived from leukemia) and THP-1 cells (human undifferentiated monocytic cell line derived from acute monocytic leukemia) were cultured in R10 medium (RPMI 1640 medium, 10% fetal bovine serum [FBS], 1% penicillin streptomycin, 1% HEPES, and 1% L-glutamine). Cell cultures were kept at 37° C. with 5% CO2. Both cell lines are non-adherent cell types. THP-1 cells and Jurkat T cells were resuspended in RPMI 1640 medium supplemented with 1% bovine serum albumin (BSA) for these experiments. 96-well Transwell permeable support inserts with 5 µm pore size filters (Corning Costar) were used. To determine the concentration of commercially available hCXCL12 (PeproTech) and recombinant hCCL2 that results in the most cell migration, hCXC12 and hCCL2-mediated transmigration assays were carried out with Jurkat and THP-1 cells, respectively. After establishing an optimal chemokine concentration for observing transmigration (50 nM for CXCL12 and 2.5 nM for CCL2), chemotaxis assays that looked at inhibition of cell migration were carried out. For the CXCL12-mediated Jurkat transmigration assays, T17 and R17 (negative control) were added to the bottom compartment at concentrations ranging from 0 to 1 µM. hCXCL12 was added to the viral proteins in the bottom chamber at a final concentration of 50 nM. The concentration of hCXCL12 was kept constant. 50,000 to 150,000 Jurkat T cells were placed in the upper compartment, which is separated by the 5 µm pore size filter. For the CCL2-mediated THP-1 transmigration assays, T17, R17 (positive control), and M3 (positive control) were added to the bottom compartment with concentrations of each ranging from 0 to 80 nM. hCCL2 was added to the viral proteins in the bottom chamber at a final concentration of 2.5 nM. The concentration of hCCL2 was kept constant. 50,000 to 75,000 THP-1 cells were placed in the upper compartment separated by the 5 ptm pore size filter. Jurkat T cells and THP-1 cells were incubated for 2.5 hours at 37° C. with 5% CO2. Following incubation, cells in the lower compartment were centrifuged at 1200 rpm for 5 minutes and lysed using CyQuant dye (Life Technologies). Cell samples were transferred to a 96-well reading plate with clear bottoms (Corning) and the plate was read using a microplate reader (Synergy H1 Hybrid Reader; BioTek) with excitation at 485 nm and emission detection at 530 nm.

Cell Surface Binding Assays

Cell surface binding assays were carried out using wild type Chinese Hamster Ovary (CHO KI) and heparan sulfate-deficient CHO 745 cells (83). CHO K1 and CHO 745 cells were maintained in F12 medium supplemented with 10% fetal calf serum (FCS) with 100 units/ml of penicillin streptomycin, and kept at 37° C. with 5% CO2. On the day of the experiment, cells were detached using pre-warmed 0.05% trypsin-EDTA and incubated for 2 minutes. Cells were centrifuged at 1200 rpm for 2 minutes, the supernatant decanted, and the cells resuspended in PBS with 1% BSA. Biotinylated T17 and R17 (positive control) were added to CHO K1 and CHO 745 cells in the following concentrations: 45 nM, 227 nM, and 909 nM for T17, and 37 nM, 190 nM, and 750 nM for R17. Cells were incubated with proteins for 30 minutes on ice and washed three times with PBS+1% BSA before the addition of secondary antibody streptavidin PE (Life Technologies). Following a 40-minute incubation period on ice, cells were washed three times with PBS+1% BSA and detected using flow cytometry. Flow cytometry was performed using FACSCalibur and the obtained data were analyzed using FlowJo software.

Results

T17 Shares Sequence Similarities with R17

Figure 10:
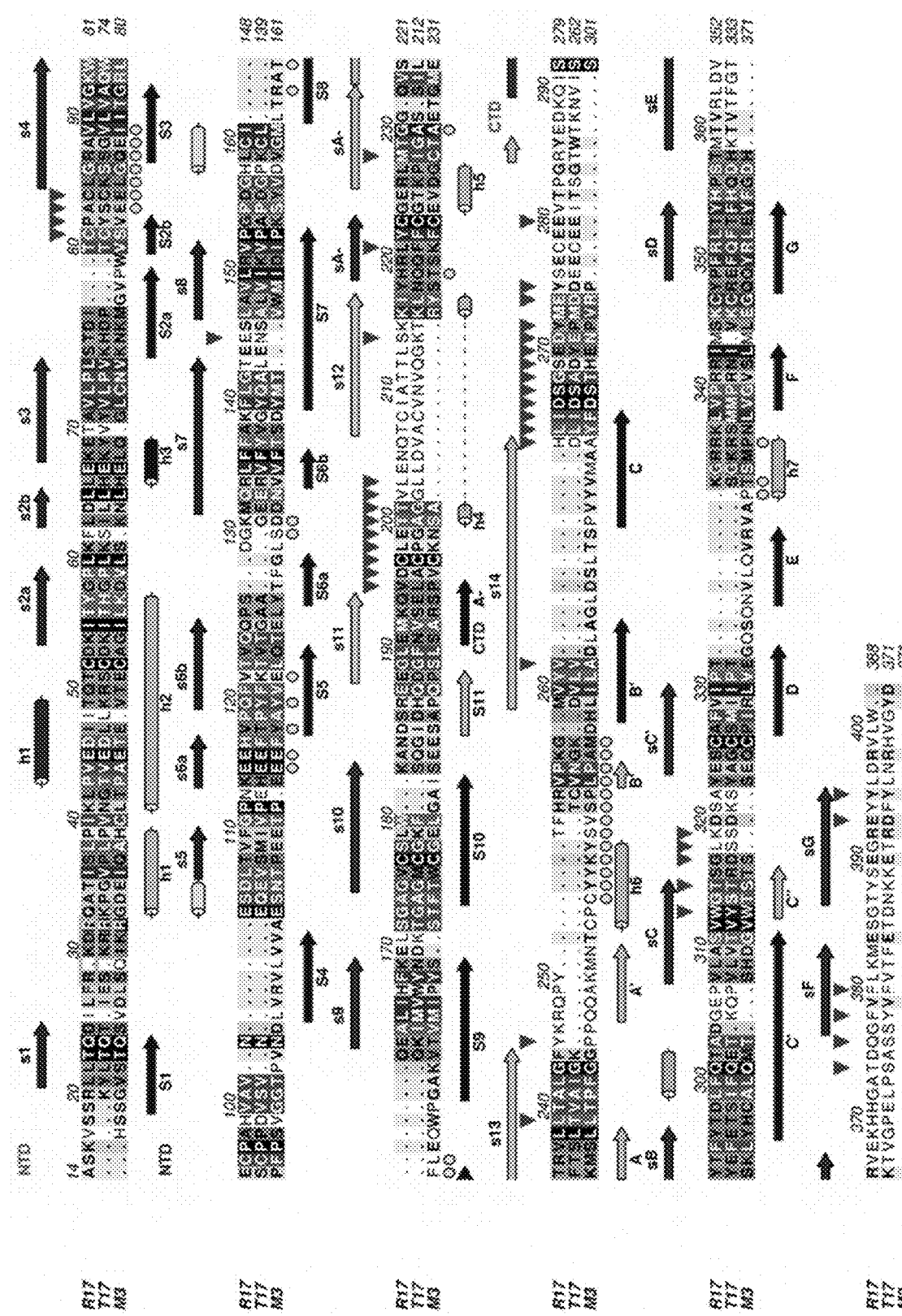
FIG. 10 shows the structure-based sequence alignment of T17, R17, and M3. The secondary structural elements of R17 are on top while those of M3 are on the bottom. Residues that are structurally similar are shown in gray while identical residues are shown in black. The yellow circles denote the chemokine-binding residues in M3 while the purple triangles indicate the chemokine-binding residues in R17. BBXB motifs are boxed in blue, and residues that are used to engage the invariant disulfide bonds in chemokines are boxed in green. (SEQ ID NOs: 1-3).
Figure 11:
FIG. 11 shows the construct of T17 includes a CD-33 signal peptide at the N-terminus and a His tag at the C-terminus. The mature form of T17 was amplified from RHVT genomic DNA and the Construct was cloned into a mammalian vector for protein expression.
Figure 12A:
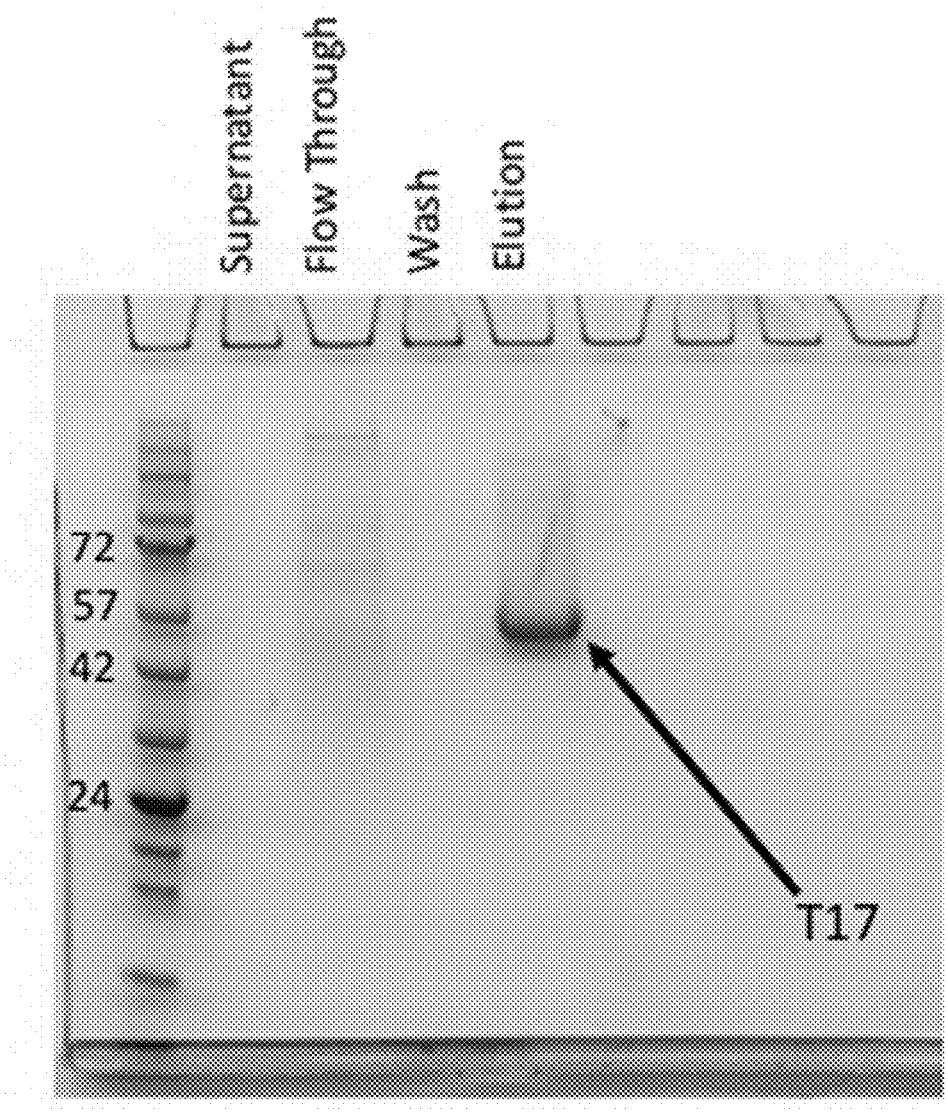
FIG. 12A, FIG. 12B and FIG. 12C show RHVT-encoded T17 was expressed in mammalian Expi293F cells.
Figure 12B:
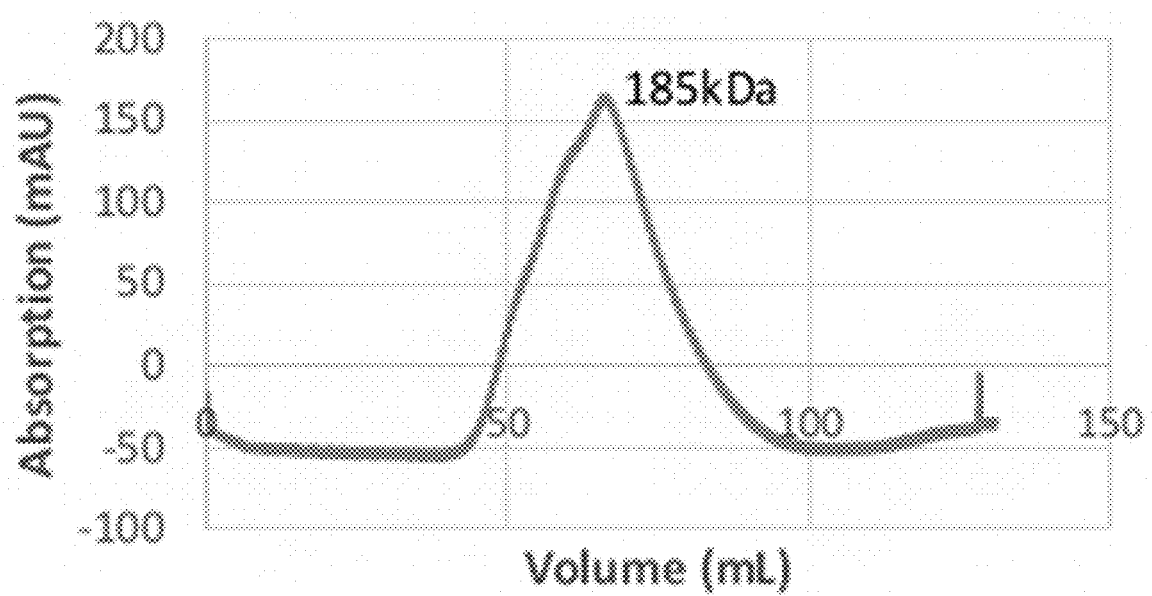
Figure 12C:
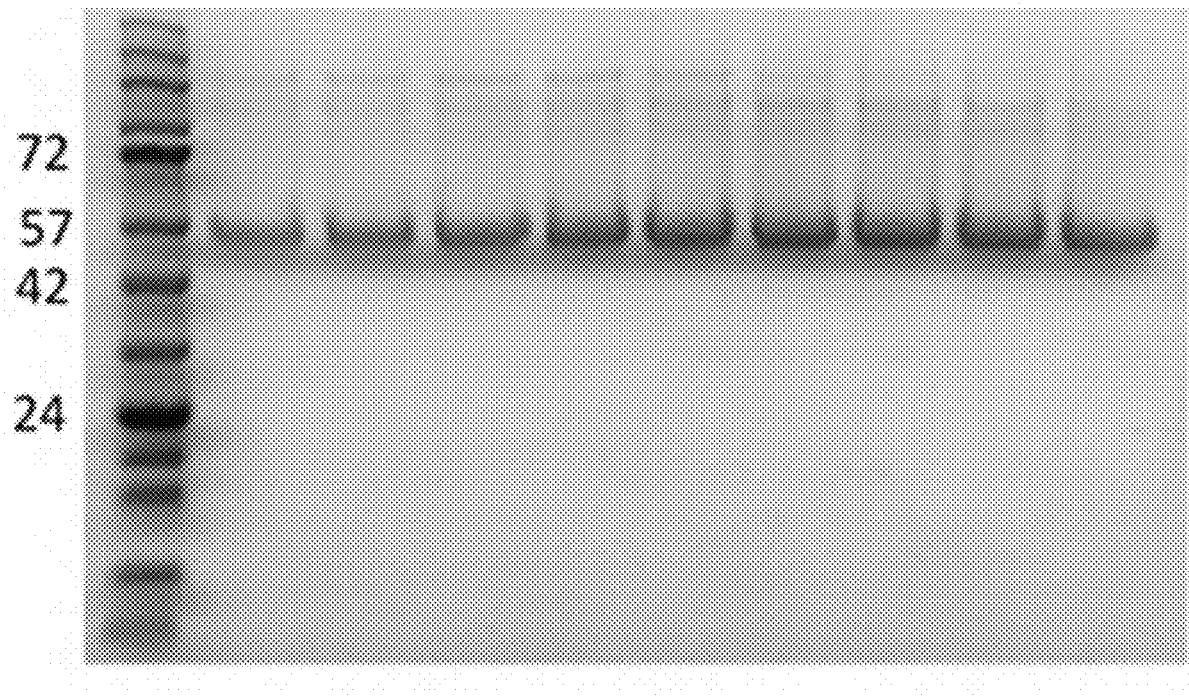
Figure 14A:
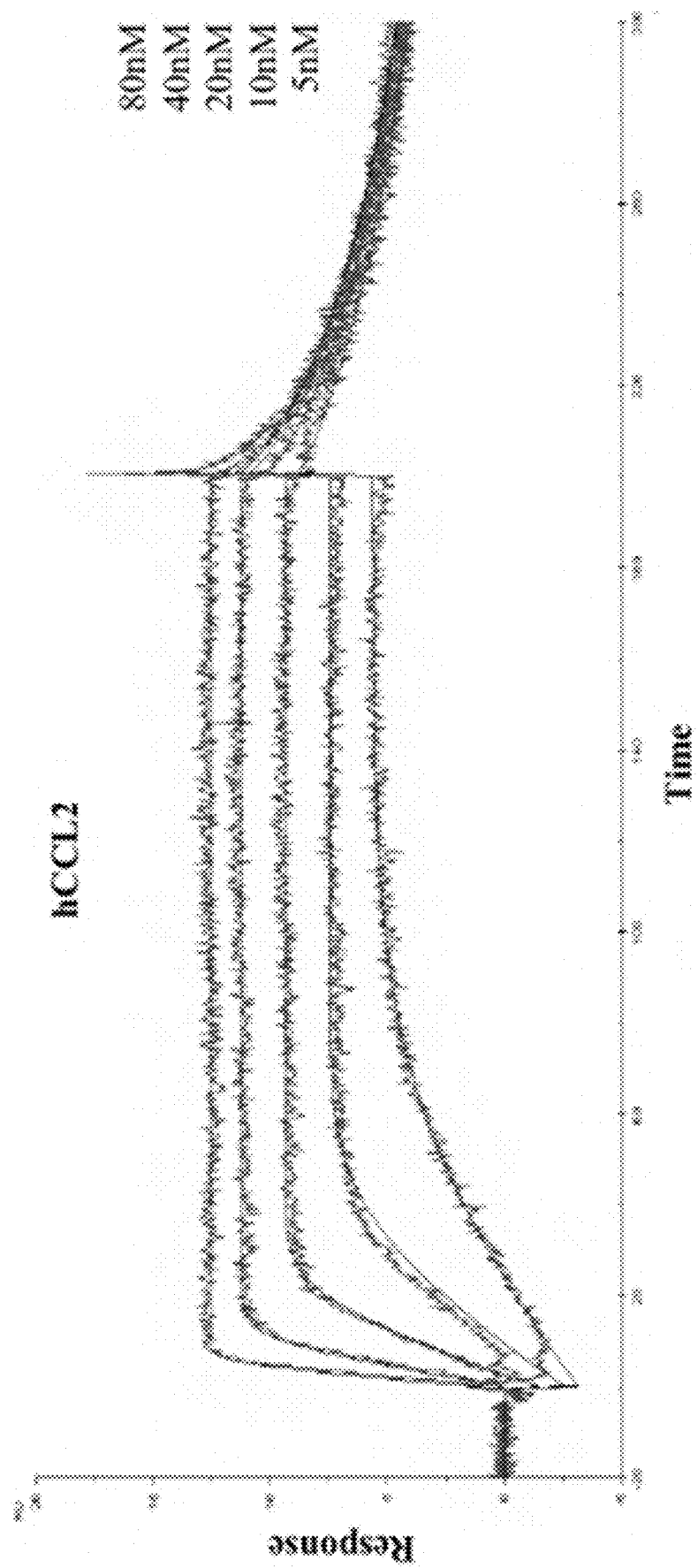
FIG. 14A, FIG. 14B and FIG. 14C show T17 binds to C, CC, and CXC chemokines with high affinity.
Figure 14B:
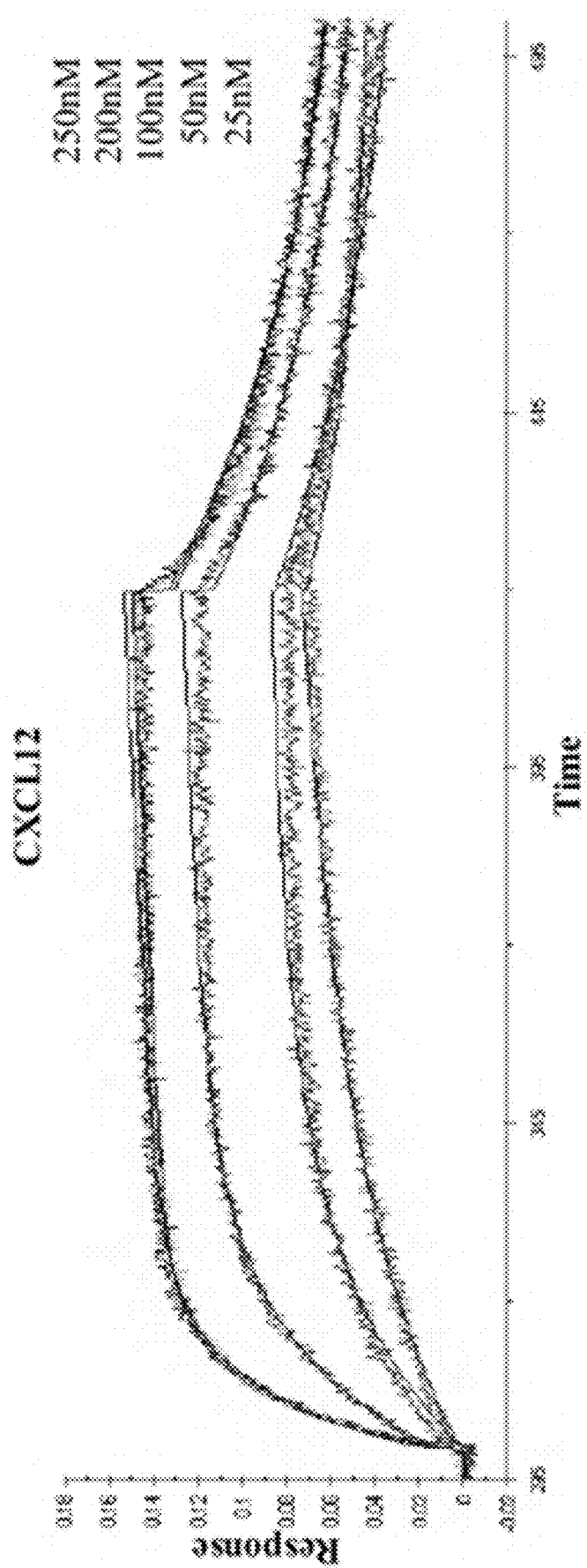
Figure 14C:
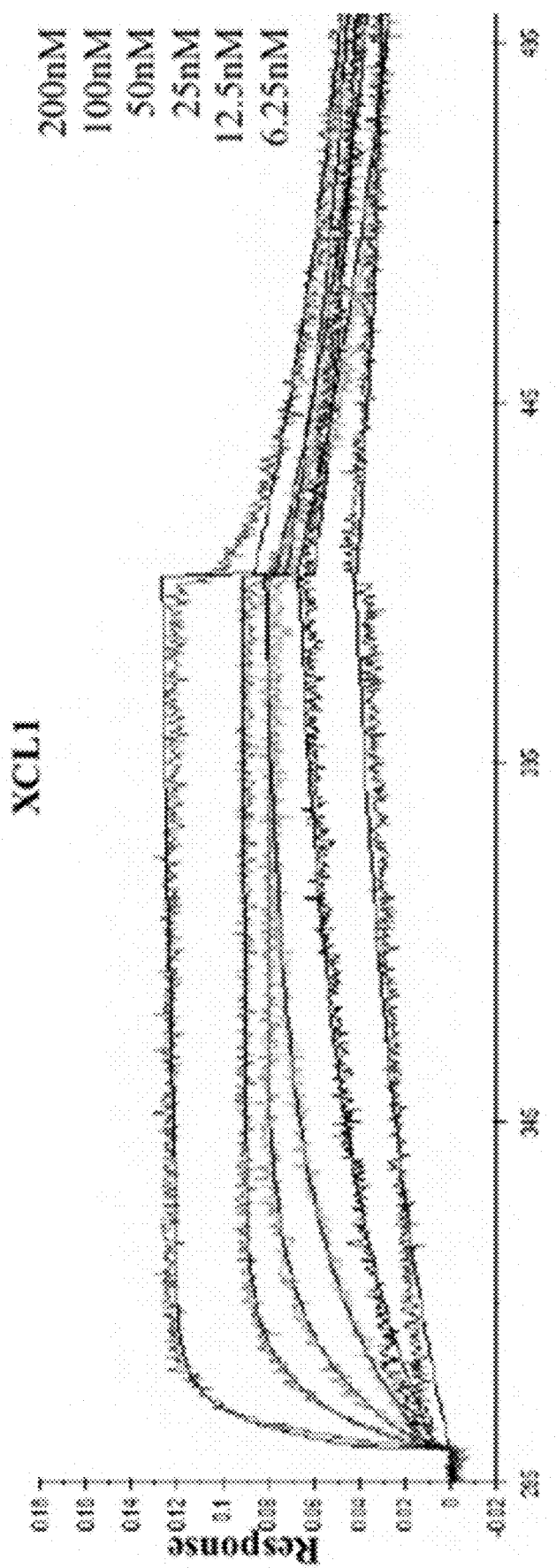
Figure 15A:
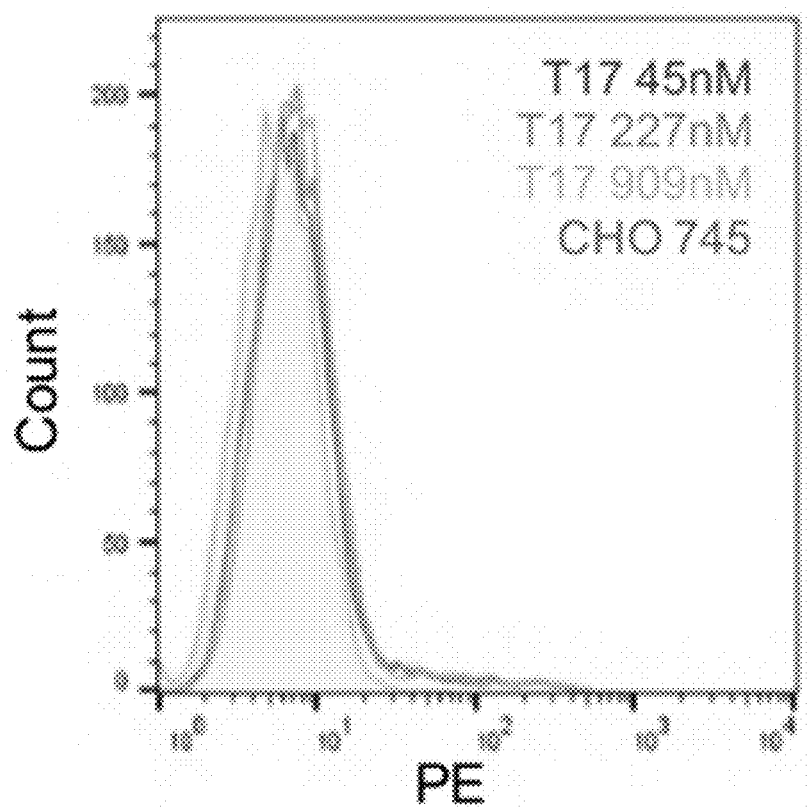
FIG. 15A and FIG. 15B show T17 binds to cell-surface GAGs. Flow cytometry analysis of (FIG. 15A) CHO745 (heparin sulfate-deficient) and (FIG. 15B) CHOK1 (wild type) cells stained with increasing concentrations of T17 demonstrate a concentration-dependent increase in GAG binding.
Figure 15B:
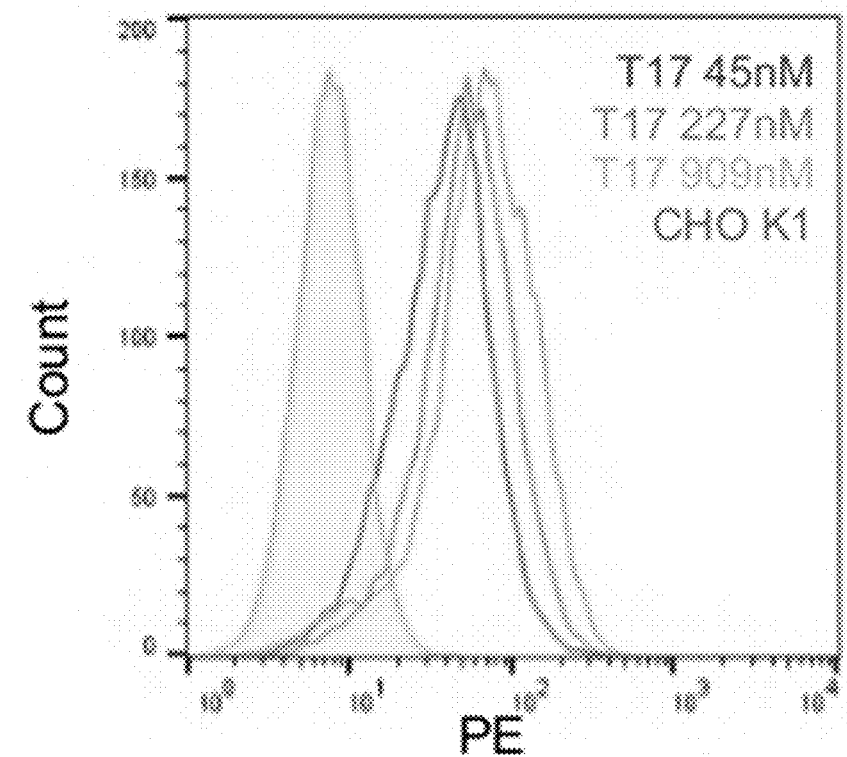

Given T17's sequence similarity to R17 and the alignment of its cysteine residues to those of R17, we used a one-on-one fold-threading algorithm on Phyre2 to model the chemokine-binding interface of T17 and compare with that of R17. Our Phyre results indicate that T17's GAG-binding motif and chemokine-binding interface align with one of R17's GAG-binding motifs and R17's chemokine-binding interface, respectively. Structure-based sequence alignment of T17, R17, and M3 reveal some important structural elements that are shared. Given that T17 shares sequence similarity with R17 and that its cysteine residues align with those of R17, T17 is more likely to adopt a similar fold to that of R17 than to that of M3. The structure-based sequence alignment shows that the residues that are responsible for engaging the invariant disulfide bonds of all four classes of chemokines in R17 are conserved in T17; as seen in FIG. 10, the residues boxed in green, signifying residues responsible for interacting with the invariant chemokine disulfide bond, are completely conserved between R17 and T17, suggesting that T17 is also a chemokine-binding protein. Moreover, the residues (V195, L198, L239, and L264) that R17 uses to engage Phe13 of CCL3, a residue critical for binding to CCL3 receptor, are partially conserved in T17. These residues are proposed to be important for the general recognition of chemokines, and the fact that they are partially conserved in T17 further suggests that T17 may be able to bind chemokines. RHVP-encoded R17 additionally encodes for an acidic pocket that serves to bury residues (Arg45 and Arg46) critical for CCL3's interaction with its receptor or cell-surface GAGs. The residues responsible for forming this pocket are not conserved in T17, suggesting that T17 may exhibit specificity for different chemokines. Given this, we hypothesized that T17 is also a viral chemokine decoy receptor, albeit with a different chemokine-binding profile.

Cloning, Expression, and Purification of RHVT-Encoded T17

The genomic DNA of mature T17 was cloned into a mammalian POE vector with the CD-33 signal peptide in place of the endogenous one as a C-terminal His-tag fusion protein (FIG. 11). The resulting construct was expressed in mammalian Expi293F cells and the secreted protein was purified using affinity chromatography followed by size exclusion chromatography (FIG. 12A and FIG. 12B). A Western blot (not shown) confirmed that T17 was successfully purified and a protein gel confirmed that the purity of T17 exceeds 90% (FIG. 12C). The final protein concentration was 4.533 mg/ml.

T17 Binds CC, CXC, and C Chemokines with High Affinity

To determine whether T17 is capable of interacting directly with chemokines, we screened both commercially available chemokines and chemokines that are produced recombinantly in the Fremont lab. Since T17 is encoded by a virus that was isolated from a rat, we preferentially selected for rat chemokines. When rat chemokines were commercially unavailable, we used mouse chemokines and human chemokines when neither rat nor mouse chemokines were available. Note, however, that there is some cross-reactivity between a given chemokine from different species. We used SPR and BLI to test T17's chemokine-binding ability and to quantify the kinetics of the binding interactions (FIG. 13). 22 chemokines were screened for binding to T17 using BLI because this technique is a high-throughput one that allows us to screen three chemokines at eight different concentrations at once. In contrast, SPR binding assays require regeneration following each injection, and thus are less ideal for high-throughput screens. Despite this, SPR is a much more sensitive method than BLI is. Consequently, all CC chemokines were tested using SPR, as the sensitivity of BLI was insufficient to accurately quantify the binding kinetics.

For the SPR experiments, we amine-coupled T17, NeutrAvidin, and R17 to a CM5 chip. We used NeutrAvidin as our negative control as it does not interact with chemokines. R17 served as our positive control for C and CC chemokine-binding since it binds to C and CC chemokines. From our SPR and BLI experiments, we determined that T17 is indeed a chemokine-binding protein that, like R17, is capable of interacting with C and CC chemokines, but displays additional specificity towards a subset of CXC chemokines (FIG. 14). T17, like R17, does not recognize the CX3C chemokine fractalkine. Of the twelve CC chemokines tested, we observed binding for all of them. Hence, T17 displays a similar binding profile as R17, but has the additional capability to bind mCCL21 which R17 did not. Of the seven CXC chemokines tested, we observed T17 to bind to only two: CXCL12 and CXCL10. The complex formed by T17's interaction with its chemokine ligand varies across all three chemokine classes that are recognized; its affinity for chemokines across C, CC, and CXC classes differs as seen by the varying KD, and the stability of the complex formed differs as evidenced by the varying half-lives (tin). Most complexes formed by T17 have a tin of less than a minute, which stands in stark contrast to those formed by R17. However, T17 appears to form rather stable complexes with mCCL5, mCCL2, and mCCL24 when R17 does not. Interestingly, T17 does not form a stable complex with mCCL3 as evidenced by its tin of approximately 90 seconds. This stands in contrast to the R17-CCL3 complex with a tin that is expected to exceed 10 minutes. The long-lived R17-CCL3 complex is presumably due to the salt bridge that one particular residue on R17 (Glu393) makes with Arg45 on the chemokine. This residue is located within an acidic pocket that enables R17 to sequester CCL3 from its receptor or from cell-surface GAGs. From the structure-based sequence alignment of R17 and T17 (FIG. 10), Glu393 in R17 is replaced by an aspartic acid in T17. This substitution in T17 could potentially explain the shorter tin observed for the T17-CCL3 complex. Though this amino acid substitution is conservative (i.e., both amino acids have similar chemical properties), aspartic acid has a side chain that is shorter by one carbon compared to glutamic acid. Consequently, it may not be able to establish a salt bridge with Arg45 on CCL3, resulting in the observed shorter-lived complex for T17.

T17 Interacts Directly with Cell-Surface GAGs

To properly establish a chemoattractant gradient, chemokines need to interact with cell-surface GAGs. It has been shown previously that R17, a chemokine decoy receptor encoded by RHVP, can interact with cell-surface GAGs via its two GAG-binding (BBXB) motifs that, when brought together in 3-dimensional space, generate a large positively charged patch that is capable of binding negatively charged cell-surface GAGs. Given that the sequence of T17 appears to contain a BBXB motif, we carried out cell surface binding assays to determine whether T17 can bind cell-surface GAGs. To do so, we biotinylated purified T17 and used it to stain both CHO K1 and CHO 745 cells. We observed that biotinylated T17 alone readily stained CHO K1 cells in a concentration-dependent manner, whereas cell surface binding assays showed only minimal background staining in the CHO 745 cells (FIG. 15). This demonstrates that T17, much like R17 (data not shown), can indeed interact directly with cell-surface GAGs.

T17 Inhibits Chemokine-Guided Cell Migration

Given that T17 can recognize and directly interact with chemokines, we next sought to understand the functional consequences of chemokine-binding. To address this, we carried out in vitro chemokine migration assays. A chemokine gradient is established by placing chemokines in the bottom compartment of a 96-well Transwell plate and by adding cells to the top compartment, which is separated by a 5 μm pore size filter. Over time, cells with receptors to the specific chemokines used will migrate towards the bottom compartment. We performed transmigration experiments with Jurkat T cells and THP-1 cells to observe the impact of chemokine-binding on cell migration in response to hCXCL12 and hCCL2, respectively. We chose Jurkat T-cells for CXCL12-mediated migration because Jurkat T-cells have been shown to express CXCR4, the receptor for

Figure 16A:
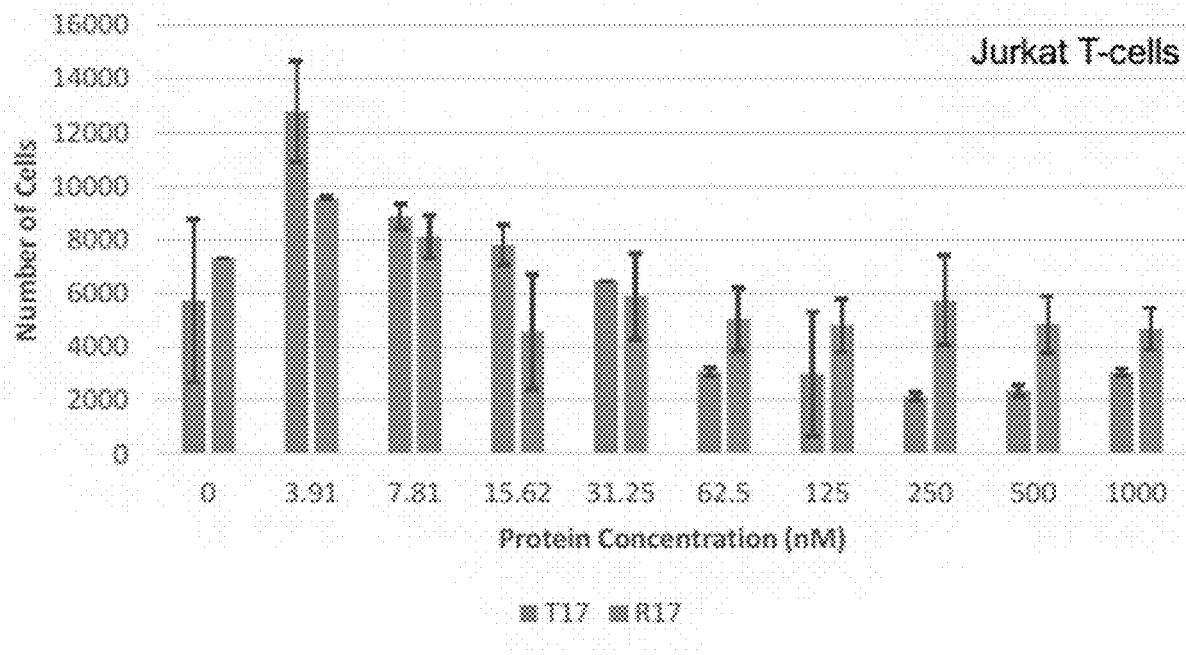
FIG. 16A and FIG. 16B show T17 blocks CXCL12-mediated and CCL2-mediated transmigration of Jurkat T cells and THP-1 cells, respectively.
Figure 16B:
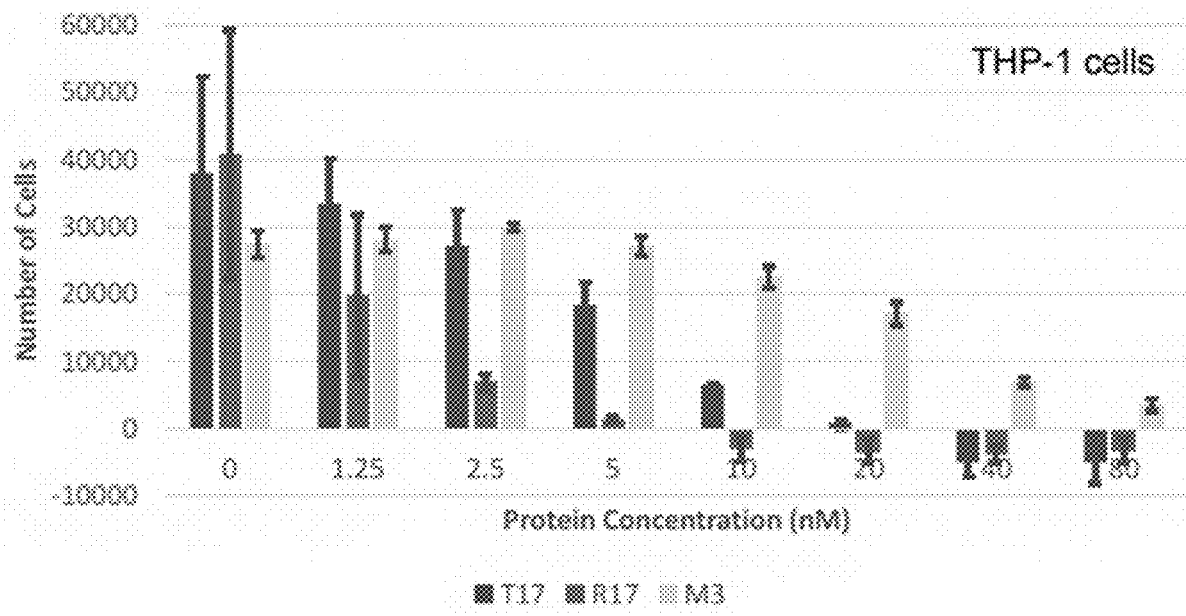

CXCL12, at high levels. THP-1 cells have been shown to express CCR2, the receptor for CCL2, on their surface. Based on our data, we discovered that T17 significantly inhibited CXCL12-mediated migration of Jurkat T cells when incubated in 5-fold molar excess of 50 nM CXCL12 (FIG. 16A). For the transmigration experiments with Jurkat T cells, we used RHVP-encoded R17, which cannot bind CXC chemokines, as our negative control, and observed no effect on CXCL12-mediated cell migration. Our data from hCCL2 transmigration experiments indicate that T17 is a potent inhibitor of CCL2-mediated cell migration, capable of significantly inhibiting cell migration when incubated in 16-fold molar excess of 2.5 nM CCL2 (FIG. 16B). THP-1 transmigratio experiments with a constant concentration of hCCL2 (2.5 nM) and varying concentrations of T17, R17, and M3 suggest that T17 is a more potent inhibitor of cell migration than M3, but weaker than R17. the bottom compartment of a 96-well Transwell plate and by adding cells to the top compartment, which is separated by a 5 µm pore size filter. Over time, cells with receptors to the specific chemokines used will migrate towards the bottom compartment. We performed transmigration experiments with Jurkat T cells and THP-1 cells to observe the impact of chemokine-binding on cell migration in response to hCXCL12 and hCCL2, respectively. We chose Jurkat T-cells for CXCL12-mediated migration because Jurkat T-cells have been shown to express CXCR4, the receptor for CXCL12, at high levels. THP-1 cells have been shown to express CCR2, the receptor for CCL2, on their surface. Based on our data, we discovered that T17 significantly inhibited CXCL12-mediated migration of Jurkat T cells when incubated in 5-fold molar excess of 50 nM CXCL12 (FIG. 16A). For the transmigration experiments with Jurkat T cells, we used RHVP-encoded R17, which cannot bind CXC chemokines, as our negative control, and observed no effect on CXCL12-mediated cell migration. Our data from hCCL2 transmigration experiments indicate that T17 is a potent inhibitor of CCL2-mediated cell migration, capable of significantly inhibiting cell migration when incubated in 16-fold molar excess of 2.5 nM CCL2 (FIG. 16B). THP-1 transmigration experiments with a constant concentration of hCCL2 (2.5 nM) and varying concentrations of T17, R17, and M3 suggest that T17 is a more potent inhibitor of cell migration than M3, but weaker than R17.

DISCUSSION

We describe here the identification and characterization of a novel soluble viral decoy receptor (chemokine-binding protein), RHVT-encoded T17. T17 displays some sequence similarity (approximately 32%) to R17 from RHVP. Previous characterization of R17 shows that this virally encoded protein is indeed a chemokine decoy receptor that recognizes certain CC and C chemokines. Our SPR and BLI binding assays demonstrate that T17 binds to C and certain CC chemokines, much like R17, but has the additional capacity to interact with a subset of CXC chemokines. T17 recognizes specific CC, C, and CXC chemokines at nanomolar affinities with rapid association kinetics and relatively short half-lives of less than a minute. However, T17 engages certain chemokines (mCCL5, mCCL2, and mCCL24) with longer half-lives that exceed a couple of minutes. Interestingly, T17 engages hCCL2 produced recombinantly in the lab with a much shorter half-life of 26 seconds compared to that of mCCL2 (225 seconds). This difference in dissociation rates observed for T17 is likely due to variations in amino acids that are critical for establishing a stable interaction, and the origin of the chemokine. Since RHVT's natural host is rats, it is perhaps not surprising that T17 is more capable of sequestering mouse chemokines for a longer duration than it is for human chemokines. In addition, the complex formed by T17 and mCCL3 has a much shorter half-life (90 seconds) than that formed by R17 and mCCL3 (greater than 10 minutes). Structural studies of R17 in complex with mCCL3 have shown that the stability of this complex is likely due to a salt bridge that forms between Glu393 on R17 and Arg45 in the 40 s loop of CCL3. When CCL2 was mutated so that its residues in the 40 s loop resembled those of CCL3, the half-life of the mutant CCL2-R17 complex was significantly longer and was of the same magnitude as that of the CCL3-R17 complex. From our structure-based sequence alignment of R17 and T17 (FIG. 10), Glu393 in R17 is replaced by an aspartic acid in T17. This substitution in T17 could explain the shorter half-life observed for the complex that T17 forms with CCL3. Though aspartic acid and glutamic acid have similar chemical properties, the carbon backbone of aspartic acid's side chain is shorter. This shorter side chain may prevent aspartic acid from properly establishing a salt bridge with Arg45 of CCL3.

Similar to M3 encoded by MHV68, RHVT-encoded T17 is a viral decoy receptor capable of binding chemokines, albeit with a more limited specificity. M3 broadly recognizes all four chemokines classes, whereas T17 recognizes only C, CC, and CXC chemokines. The fact that T17 shares sequence similarity with R17 and is more likely to adopt a similar fold to that of R17 than to that of M3 due to the alignment of cysteine residues in R17 and T17 may lend support to the different chemokine-binding profile observed for T17.

All three herpesvirus-encoded decoy receptors appear to bind chemokines to block the host chemokine signaling network, and thus chemokine-mediated cell migration. Chemotaxis assays have demonstrated that R17 potently blocks CCL2 and CCL3-mediated transmigration. Calcium release assays have shown that, functionally, M3's interaction with chemokines inhibits the release of calcium, a key event in the chemokine signaling pathway. Additionally, chemotaxis assays with M3 demonstrate that M3 can block CC chemokine-mediated transmigration.

However, only R17 and T17 appear to interact directly with cell surfaces through GAGs. T17's BBXB motif aligns with one of R17's two BBXB motifs. R17's BBXB motifs, though far apart in primary structure, come together in the protein's tertiary structure to form a positively charged patch that can interact with negatively charged cell-surface GAGs. R17 has been shown to be able to bind GAGs and chemokines simultaneously, presumably allowing it to sequester chemokines locally at the site of infection. Our cell surface binding assays with CHO K1 and CHO 745 cells indicate that, much like R17, T17 can interact directly with cell surfaces via GAGs.

We demonstrate that T17 encoded by RHVT is a chemokine-binding protein capable of recognizing subsets of CC, C, and CXC chemokines, and cell-surface GAGs. The differences observed in the chemokine-binding profile of T17 and R17 will be clearer once the structures of T17 alone and in complex with a CXC and CC chemokine are solved. These structural studies will allow us to pinpoint the specific residues responsible for T17's ability to recognize CXC and CC chemokines. Further chemotaxis assays with Jurkat T cells and THP-1 cells will help elucidate the functional consequences of T17's interactions with CXCL12 and CCL2, respectively. To better understand T17's role in RHVT pathogenesis, in vivo experiments can be performed. In vivo studies of T17 will also allow us to evaluate its therapeutic potential given its ability to sequester chemokines to disrupt host chemokine signaling network and chemokine-mediated cell migration.

T17 is the first gamma-herpesvirus chemokine-binding protein identified that shares sequence and structural similarities with known herpesvirus-encoded chemokine-binding proteins. Since herpesviruses-encoded immune evasion proteins are not known to share structural nor sequence similarities, the identification and characterization of RHVT-encoded T17 suggest that herpesvirus-encoded chemokine-binding proteins may share common structural features, a trend similar to that observed for PIE domains in poxviruses. This would allow us to be able to better identify other herpesvirus-encoded immune evasion proteins through sequence or structural similarities to T17 and enhance our understanding of herpesviruses. proteins. Since herpesviruses-encoded immune evasion proteins are not known to share structural nor sequence similarities, the identification and characterization of RHVT-encoded T17 suggest that herpesvirus-encoded chemokine-binding proteins may share common structural features, a trend similar to that observed for PIE domains in poxviruses. This would allow us to be able to better identify other herpesvirus-encoded immune evasion proteins through sequence or structural similarities to T17 and enhance our understanding of herpesviruses.

What is claimed is:

1. A method of preventing ischemia reperfusion injury in an organ transplanted into a subject, the method comprising perfusing the organ with an effective amount of a composition comprising T17 (SEQ ID NO: 2) alone or in combination with R17 (SEQ ID NO: 1) and/or M3 (SEQ ID NO: 3) before transplanting the organ into the subject.

2. The method of claim 1, wherein perfusing the organ is with an effective amount of a composition comprising a combination of R17 (SEQ ID NO: 1), M3 (SEQ ID NO: 3), and T17 (SEQ ID NO: 2).

3. The method of claim 1, wherein prevention of ischemia reperfusion injury prevents acute or chronic organ rejection.

4. The method of claim 1, wherein accumulation of at least one subset of leukocytes is prevented, wherein the subset is selected from the group consisting of neutrophils, macrophages, dendritic cells, T cells, and NK cells.

5. A method of preventing an inflammatory condition associated with an organ transplant, tissue transplant, stem cell transplant or embryonic stem cell transplant, the method comprising: contacting the transplant organ, tissue, stem cells or embryonic stem cells with an effective amount of a composition comprising T17 (SEQ ID NO: 2) alone or in combination with R17 (SEQ ID NO: 1) and/or M3 (SEQ ID NO: 3).

6. The method of claim 5, wherein the composition sequesters chemokines that are involved in recruitment and migration of inflammatory cells, so that the inflammatory condition associated with the transplantation is prevented.

7. The method of claim 5, wherein contacting the transplant organ, tissue, stem cells, or embryonic stem cells is with a composition comprising a combination of R17 (SEQ ID NO: 1), M3 (SEQ ID NO: 3), and T17 (SEQ ID NO: 2).

8. The method of claim 5, wherein prevention of the inflammatory condition prevents acute or chronic transplant rejection.

9. A method of treating or preventing ischemic heart disease in a subject, the method comprising, administering to the subject a composition comprising a therapeutically effect amount of a composition comprising T17 (SEQ ID NO: 2) alone or in combination with R17 (SEQ ID NO: 1) and/or M3 (SEQ ID NO: 3).

10. The method of claim 9, wherein the composition sequesters chemokines that are involved in recruitment and migration of inflammatory cells, so that symptoms associated with ischemic heart disease are treated or prevented.

\* \* \* \* \*

```
                        SEQUENCE LISTING

<160> NUMBER OF SEQ ID NOS: 12

<210> SEQ ID NO 1
<211> LENGTH: 412
<212> TYPE: PRT
<213> ORGANISM: Artificial Sequence
<220> FEATURE:
<223> OTHER INFORMATION: SYNTHESIZED

<400> SEQUENCE: 1

Gly Pro Val Gly Glu Pro Val Ala Ser Glu Ile Asn Glu Ala Ser Lys
1               5                   10                  15

Val Ser Ser Arg Leu Leu Thr Gln Asp Ile Leu Phe Arg Lys Asp Arg
            20                  25                  30

Gln Ala Thr Ile Ser Leu Pro Ile Lys Leu Pro Val Glu Asp Ile Ile
        35                  40                  45

Thr Gln Thr Cys Asp Lys Ile Thr Tyr Gly Pro Leu Lys Phe Leu Asp
    50                  55                  60

Leu Leu Glu Lys Glu Thr Ala Val Leu Pro Leu Ser Thr Asp Ile Thr
65                  70                  75                  80

Cys Pro Ala Cys Leu Gly Arg Ala Val Leu Val Gly Lys Trp Glu Cys
                85                  90                  95

Pro Ala His Val Ala Val Asn Glu Ser Asp Leu Thr Val Phe Gly Pro
            100                 105                 110

Asn Lys Glu Glu His Val Pro Gln Phe Val Thr Val Gln Gln Pro Ser
        115                 120                 125

Asp Gly Lys Met Gln Arg Leu Phe Phe Ala Lys Phe Leu Gly Thr Glu
    130                 135                 140

Glu Ser Leu Ala Val Leu Arg Val Pro Gly Pro Asp Gly His Leu Cys
145                 150                 155                 160

Ile Gln Glu Ala Leu Ile His Phe Lys Glu Leu Ser Gly Ala Gly Val
                165                 170                 175

Cys Ser Leu Trp Lys Ala Asn Asp Ser Arg Glu Glu Gly Leu Glu Met
            180                 185                 190

Lys Gln Val Asp Cys Leu Glu Thr Thr Val Leu Glu Asn Gln Thr Cys
        195                 200                 205

Ile Ala Thr Thr Leu Ser Lys Lys Ile Tyr His Arg Leu Tyr Cys Gly
    210                 215                 220

Glu Arg Leu Met Thr Gly Gly Gln Val Ser Thr Arg Val Leu Leu Thr
225                 230                 235                 240

Ala Leu Gly Phe Tyr Lys Arg Gln Pro Tyr Thr Phe His Arg Val Pro
                245                 250                 255

Lys Gly Met Val Tyr Val His Leu Ile Asp Ser Gly Ser Glu Asp Tyr
```

```
                260                 265                 270
Met Glu Tyr Ser Glu Cys Glu Val Thr Pro Gly Arg Tyr Glu Asp
            275                 280                 285
Lys Gln Ile Ser Tyr Thr Phe Tyr Thr Asp Leu Phe Gln Thr Ala Asp
290                 295                 300
Gly Glu Pro Val Leu Ala Ser Val Trp Gly Thr Ser Gly Leu Lys Asp
305                 310                 315                 320
Ser Ala Tyr Glu Ser Cys Ala Phe Val Ile Pro Thr Lys Gly Arg Arg
            325                 330                 335
Lys Leu Val Pro Arg Arg Ile Met Ser Lys Cys Tyr Pro Phe Arg Leu
            340                 345                 350
Thr Tyr His Pro Ser Thr Met Thr Val Arg Leu Asp Val Arg Val Glu
            355                 360                 365
Lys His His Gly Ala Thr Asp Gln Gly Phe Val Phe Leu Lys Met Glu
            370                 375                 380
Ser Gly Thr Tyr Ser Glu Gly Arg Glu Tyr Tyr Leu Asp Arg Val Leu
385                 390                 395                 400
Trp Gly Glu Asp Ser Ser Thr Asn Asn Val Leu Gln
            405                 410

<210> SEQ ID NO 2
<211> LENGTH: 297
<212> TYPE: PRT
<213> ORGANISM: Artificial Sequence
<220> FEATURE:
<223> OTHER INFORMATION: SYNTHESIZED

<400> SEQUENCE: 2

Ala Glu Lys Glu Val Thr Asn Ser Lys Leu Asp Thr Leu Asp Gly Lys
1               5                   10                  15
Tyr Leu Thr Gln Thr Ile Glu Ser Lys Arg Arg Lys Pro Gly Val Pro
            20                  25                  30
Leu Pro Val Asn Gly Thr Val Glu Asp Leu Leu Lys Arg Ser Cys Asp
            35                  40                  45
Lys Ile Thr His Gly Pro Leu Lys Ser Ile Leu Leu His Glu Lys Tyr
50                  55                  60
Val Tyr Val Leu Pro Val Lys His Asp Pro Thr Cys Tyr Ser Cys Lys
65                  70                  75                  80
Ser Ser Gly Val Leu Val Ala Gln Trp Ser Cys Pro Pro Asp Val Ser
            85                  90                  95
Val Asn Glu Gln Glu Val Ser Met Ile Val Pro Glu His Glu Glu Phe
            100                 105                 110
Thr Pro Tyr Phe Lys Thr Val Thr Gly Ala Ala Gly Glu Glu Arg Val
            115                 120                 125
Phe Tyr Val Gly Tyr Gln Ala Leu Glu Asn Ser Ala Leu Val Ile Lys
            130                 135                 140
Val Pro Ala Pro Asp Gly Pro Lys Cys Leu Gln Lys Ile Met Val Trp
145                 150                 155                 160
Tyr Asn Asp Lys Thr Gly Ala Gly Met Cys Gly Lys Phe Ser Gln Gly
            165                 170                 175
Ile Asp His Gln Asp Gly Phe Asn Val Ser Glu Leu Ala Cys Pro Gly
            180                 185                 190
Ala Gly Gly Leu Leu Asp Val Ala Cys Val Asn Val Gln Gly Lys Thr
            195                 200                 205
Lys Leu Asn Gln Gln Phe Phe Cys Gly Thr Lys Pro Ile Gly Ala Ser
```

```
              210                 215                 220
Ser Ile Leu Phe Thr Ser Leu Thr Val Ala Ile Gly Lys Thr Cys Val
225                 230                 235                 240

Asn Gly Lys Asp Val Leu Val Asp Leu Ile Asp Ser Ala Asp Tyr Glu
                245                 250                 255

Pro Met Asp Asp Glu Glu Cys Glu Glu Ile Thr Ser Gly Thr Trp Thr
                260                 265                 270

Lys Asn Val Ile Ser Tyr Glu Phe Glu Thr Ser Ile Phe Gln Glu Thr
                275                 280                 285

Lys Gln Pro Val Leu Val Thr Val Tyr
                290                 295

<210> SEQ ID NO 3
<211> LENGTH: 382
<212> TYPE: PRT
<213> ORGANISM: Artificial Sequence
<220> FEATURE:
<223> OTHER INFORMATION: SYNTHESIZED

<400> SEQUENCE: 3

Leu Thr Leu Gly Leu Ala Pro Ala Leu Ser Thr His Ser Ser Gly Val
1               5                   10                  15

Ser Thr Gln Ser Val Asp Leu Ser Gln Ile Lys Arg Gly Asp Glu Ile
                20                  25                  30

Gln Ala His Cys Leu Thr Pro Ala Glu Thr Glu Val Thr Glu Cys Ala
                35                  40                  45

Gly Ile Leu Lys Asp Val Leu Ser Lys Asn Leu His Glu Leu Gln Gly
        50                  55                  60

Leu Cys Asn Val Lys Asn Lys Met Gly Val Pro Trp Val Ser Val Glu
65                  70                  75                  80

Glu Leu Gly Gln Glu Ile Ile Thr Gly Arg Leu Pro Phe Pro Ser Val
                85                  90                  95

Gly Gly Thr Pro Val Asn Asp Leu Val Arg Val Leu Val Val Ala Glu
                100                 105                 110

Ser Asn Thr Pro Glu Glu Thr Pro Glu Glu Glu Phe Tyr Ala Tyr Val
                115                 120                 125

Glu Leu Gln Thr Glu Leu Tyr Thr Phe Gly Leu Ser Asp Asp Asn Val
        130                 135                 140

Val Phe Thr Ser Asp Tyr Met Thr Val Trp Met Ile Asp Ile Pro Lys
145                 150                 155                 160

Ser Tyr Val Asp Val Gly Met Leu Thr Arg Ala Thr Phe Leu Glu Gln
                165                 170                 175

Trp Pro Gly Ala Lys Val Thr Val Met Ile Pro Tyr Ser Ser Thr Phe
                180                 185                 190

Thr Trp Cys Gly Glu Leu Gly Ala Ile Ser Glu Glu Ser Ala Pro Gln
                195                 200                 205

Pro Ser Leu Ser Ala Arg Ser Pro Val Cys Lys Asn Ser Ala Arg Tyr
        210                 215                 220

Ser Thr Ser Lys Phe Cys Glu Val Asp Gly Cys Thr Ala Glu Thr Gly
225                 230                 235                 240

Met Glu Lys Met Ser Leu Leu Thr Pro Phe Gly Gly Pro Gln Gln
                245                 250                 255

Ala Lys Met Asn Thr Cys Pro Cys Tyr Tyr Lys Tyr Ser Val Ser Pro
                260                 265                 270

Leu Pro Ala Met Asp His Leu Ile Leu Ala Asp Leu Ala Gly Leu Asp
```

```
                275                 280                 285
Ser Leu Thr Ser Pro Val Tyr Val Met Ala Ala Tyr Phe Asp Ser Thr
    290                 295                 300

His Glu Asn Pro Val Arg Pro Ser Ser Lys Leu Tyr His Cys Ala Leu
305                 310                 315                 320

Gln Met Thr Ser His Asp Gly Val Trp Thr Ser Thr Ser Ser Glu Gln
                325                 330                 335

Cys Pro Ile Arg Leu Val Glu Gly Gln Ser Gln Asn Val Leu Gln Val
            340                 345                 350

Arg Val Ala Pro Thr Ser Met Pro Asn Leu Val Gly Val Ser Leu Met
        355                 360                 365

Leu Glu Gly Gln Gln Tyr Arg Leu Glu Tyr Phe Gly Asp His
    370                 375                 380

<210> SEQ ID NO 4
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 4

Asn Ala Gly Ala Gln
1               5

<210> SEQ ID NO 5
<211> LENGTH: 4
<212> TYPE: PRT
<213> ORGANISM: Artificial Sequence
<220> FEATURE:
<223> OTHER INFORMATION: SYNTHESIZED

<400> SEQUENCE: 5

Leu Ile Asp Ser
1

<210> SEQ ID NO 6
<211> LENGTH: 13
<212> TYPE: PRT
<213> ORGANISM: Artificial Sequence
<220> FEATURE:
<223> OTHER INFORMATION: Synthesized

<400> SEQUENCE: 6

Met Pro Leu Leu Leu Leu Leu Pro Leu Leu Trp Ala Gly
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthesized

<400> SEQUENCE: 7

His His His His His His His His
1               5

<210> SEQ ID NO 8
<211> LENGTH: 5
<212> TYPE: PRT
<213> ORGANISM: Artificial Sequence
<220> FEATURE:
<223> OTHER INFORMATION: Synthesized
```

```
<400> SEQUENCE: 8

Lys Gly Arg Arg Lys
1               5

<210> SEQ ID NO 9
<211> LENGTH: 5
<212> TYPE: PRT
<213> ORGANISM: Artificial Sequence
<220> FEATURE:
<223> OTHER INFORMATION: Synthesized

<400> SEQUENCE: 9

Asp Gly Glu Glu Asp
1               5

<210> SEQ ID NO 10
<211> LENGTH: 5
<212> TYPE: PRT
<213> ORGANISM: Artificial Sequence
<220> FEATURE:
<223> OTHER INFORMATION: Synthesized

<400> SEQUENCE: 10

Asp Ser Gly Ser Glu
1               5

<210> SEQ ID NO 11
<211> LENGTH: 5
<212> TYPE: PRT
<213> ORGANISM: Artificial Sequence
<220> FEATURE:
<223> OTHER INFORMATION: Synthesized

<400> SEQUENCE: 11

Asn Ala Gly Ala Gln
1               5

<210> SEQ ID NO 12
<211> LENGTH: 5
<212> TYPE: PRT
<213> ORGANISM: Artificial Sequence
<220> FEATURE:
<223> OTHER INFORMATION: Synthesized

<400> SEQUENCE: 12

Gly Gly Gly Asp Ser
1               5
```